United States Patent
Elemento et al.

(10) Patent No.: US 11,462,303 B2
(45) Date of Patent: Oct. 4, 2022

(54) COMPUTATIONAL SYSTEMS AND METHODS FOR IMPROVING THE ACCURACY OF DRUG TOXICITY PREDICTIONS

(71) Applicant: Cornell University, Ithaca, NY (US)

(72) Inventors: Olivier Elemento, New York, NY (US); Kaitlyn Gayvert, New York, NY (US); Neel Madhukar, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 784 days.

(21) Appl. No.: 16/332,769

(22) PCT Filed: Sep. 12, 2017

(86) PCT No.: PCT/US2017/051106
§ 371 (c)(1),
(2) Date: Mar. 12, 2019

(87) PCT Pub. No.: WO2018/049376
PCT Pub. Date: Mar. 15, 2018

(65) Prior Publication Data
US 2019/0252036 A1    Aug. 15, 2019

Related U.S. Application Data

(60) Provisional application No. 62/393,481, filed on Sep. 12, 2016.

(51) Int. Cl.
| | | |
|---|---|---|
| *G01N 31/00* | (2006.01) |
| *G16C 20/30* | (2019.01) |
| *G16B 40/00* | (2019.01) |
| *G16B 15/00* | (2019.01) |
| *G16C 20/00* | (2019.01) |
| *G16B 5/20* | (2019.01) |
| *G16C 20/70* | (2019.01) |

(52) U.S. Cl.
CPC .............. *G16C 20/30* (2019.02); *G16B 5/20* (2019.02); *G16B 15/00* (2019.02); *G16B 40/00* (2019.02); *G16C 20/00* (2019.02); *G16C 20/70* (2019.02)

(58) Field of Classification Search
None
See application file for complete search history.

(56) References Cited

U.S. PATENT DOCUMENTS

| | | |
|---|---|---|
| 2007/0294068 A1 | 12/2007 | Jones et al. |
| 2009/0024547 A1 | 1/2009 | Lu et al. |
| 2013/0144584 A1 | 6/2013 | Chen et al. |
| 2013/0173503 A1 | 7/2013 | Segall et al. |
| 2014/0257773 A1* | 9/2014 | Lee .................. G16C 20/30 703/2 |
| 2014/0278130 A1 | 9/2014 | Bowles et al. |
| 2014/0297199 A1* | 10/2014 | Osten .............. G01N 33/5014 702/19 |

FOREIGN PATENT DOCUMENTS

WO    WO-2015/028597 A1    3/2015

OTHER PUBLICATIONS

Mayr, Andreas, et al. "DeepTox: toxicity prediction using deep learning." Frontiers in Environmental Science 3 (2016): 80.*
Hizukuri et al., "Predicting target proteins for drug candidate compounds based on a drug-induced gene expression data in a chemical structure-independent manner," BMC Medical Genomics, 8:82, 10 pages (2015).
International Search Report and Written Opinion, PCT/US2017/051106 (dated Dec. 4, 2017).
Noh et al., "Inferring gene targets of drugs and chemical compounds from gene expression profiles," Bioinformatics, 32(14), pp. 2120-2127 (Mar. 18, 2016).
Extended European Search Report in EP Patent No. 17849757.4 dated Apr. 22, 2020.
Gayvert, et al., Abstract 3916: A "moneyball" approach to predicting clinical trial toxicity events, Cancer Research, Jul. 2016, vol. 76, Issue 14 Supplement, 4 pages, retrieved from the Internet on Apr. 4, 2020: URL: https://cancerres.aacrjournals.org/content/76/14_Supplement/3916.
Huang, et al., "Predicting adverse drug reaction profiles by integrating protein interaction networks with drug structures", Protemics, 2013, vol. 13, pp. 313-324.
Wang, et al., "Drug-induced adverse events prediction with the LINCS L1000 data," Bioinformatics | Oxford Academic, Bioinformatics, Apr. 1, 2016, vol. 32, Issue 15, pp. 2338-2345, retrieved from the Internet on Apr. 8, 2020: URL: https://academic.oup.com/bioinformatics/article/32/15/2338/1744048.

\* cited by examiner

*Primary Examiner* — Anna Skibinsky
(74) *Attorney, Agent, or Firm* — Foley & Lardner LLP

(57) ABSTRACT

In some implementations, the present solution can determine a first structural vector of a first chemical based on a chemical structure of the first chemical. The system can also determine first target vector of the first chemical based on at least one gene target for the first chemical. The system can use the structural vector and the target vector to generate a toxicity predictor score for the first chemical.

20 Claims, 31 Drawing Sheets

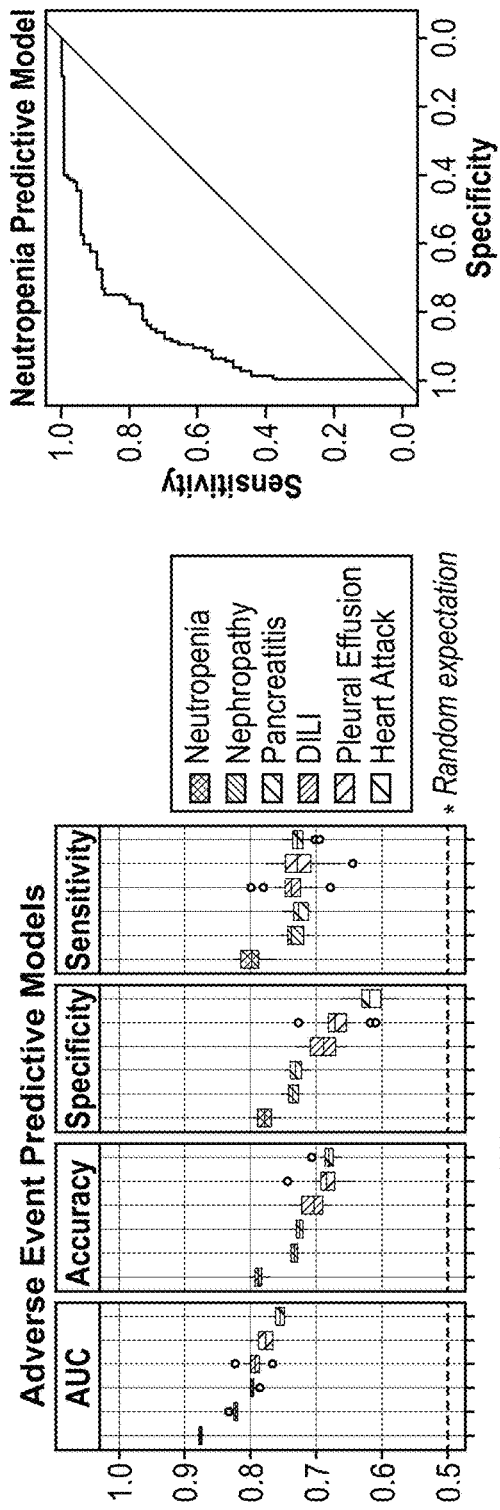
FIG. 14A
FIG. 14B
FIG. 14C
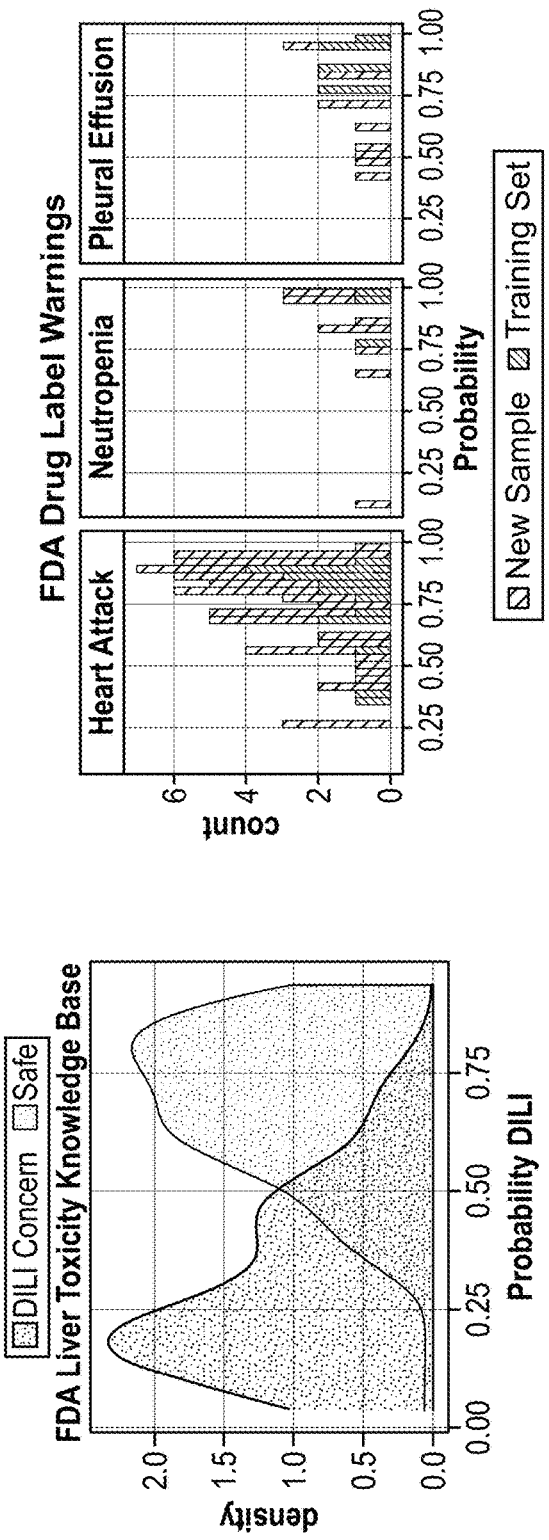
FIG. 14D

| Chemical 1 | Chemical Efficacy 410 | Post-Treatment Transciptional Responses 415 | Chemical Structure 420 | Reported Adverse Effects 425 | Bioassay Results 430 | Chemogenomic Fitness Score 435 | Known Binding Targets 440 |

Vinblastine-
Depolymerizing (Control)

NSC406042 - Depolymerizing

COMPUTATIONAL SYSTEMS AND METHODS FOR IMPROVING THE ACCURACY OF DRUG TOXICITY PREDICTIONS

CROSS-REFERENCE TO RELATED APPLICATION

This application is a National Stage Application of PCT/US2017/051106, filed Sep. 12, 2017, which claims the benefit of priority under 35 U.S.C. § 119 to U.S. Provisional Patent Application No. 62/393,481, filed Sep. 12, 2016, which is herein incorporated by reference in its entirety.

BACKGROUND OF THE DISCLOSURE

Over the past decade, the rate of drug attrition due to clinical trial failures has risen substantially. Failures in all phases of clinical trials have skyrocketed over the past three decades, with a substantial portion occurring for safety reasons. This is occurring despite improvements in all stages of the drug development pipeline. Unfortunately, it is difficult to identify chemicals that have unfavorable toxicity properties before conducting clinical trials.

SUMMARY OF THE DISCLOSURE

The present disclosure discusses a new data-driven system that can predict the likelihood of toxicity in clinical trials and whether the drug would pass the toxicity requirements of a clinical trial. The system can integrate properties of a chemical's gene targets and chemical (or molecular) structure to provide a toxicity predictor score. The present solution can provide a data-driven, broadly applicable strategy to identify drugs likely to possess manageable toxicity in clinical trials and can help drive the design of therapeutic agents with less toxicity.

According to one aspect of the disclosure, a system to improve the accuracy of drug toxicity predictions can include a data processing system. The data processing system can include one or more processors that are coupled to a memory. The data processing system can be configured to determine a first structural vector of a first chemical based on a chemical structure of the first chemical. The first structural vector can include values corresponding to one or more features derived from the chemical structure of the first chemical. The data processing system can determine a first target vector of the first chemical based on at least one gene target for the first chemical. The first target vector can include values corresponding to one or more features derived from the at least one gene target and the first chemical. The data processing system can generate, using a machine learning classifier, a toxicity predictor score for the first chemical.

The machine learning classifier can be trained using a first plurality of reference chemicals and a second plurality of reference chemicals. Each reference chemical of the first plurality of reference chemicals can be identified as belonging to a first class known to demonstrate adverse effects below an adverse effects threshold. Each of the reference chemicals can have a respective structural vector that can include values corresponding to one or more features derived from the chemical structure of the respective reference chemical. The references chemicals can each have a respective target vector that can include values corresponding to one or more features derived from one or more gene targets and the respective reference chemical.

Each second reference chemical of the second plurality of reference chemicals can be identified as belonging to a second class known to demonstrate adverse effects above the adverse effects threshold. Each of the reference chemicals in the second plurality of reference chemicals can have a respective structural vector that can include values corresponding to one or more features derived from the chemical structure of the respective second reference chemical. Each of the reference chemicals in the second plurality of reference chemicals can have a respective target vector that can include values corresponding to one or more features derived from one or more gene targets and the respective second reference chemical. The data processing system can compare the toxicity predictor score for the first chemical to the adverse effects threshold. The data processing system can provide, responsive to determining that the toxicity predictor score for the first chemical is below the adverse effects threshold, a prediction that the first chemical will demonstrate adverse effects below the adverse effects threshold.

In some implementations, the structural vector can be based on at least one chemical property feature and at least one drug-likeness feature. The at least one chemical property feature can include a polar surface area, a molecular weight, a hydrogen bond donor count, a hydrogen bond acceptor count, a charge number, or a number of rotatable bonds. The at least one drug-likeness feature includes a quantitative estimate of drug-likeness (QED), a rule of five measure, a Veber rule measure, or a Ghose rule measure.

In some implementations, the target vector can be based on at least one of a gene expression feature or a target feature. The gene expression feature can indicate a level of gene expression in a target tissue based on an exposure to the first chemical. The target tissue can be at least one of liver tissue, heart tissue, kidney tissue, or brain tissue.

In some implementations, the target feature can include at least one of a network connectivity feature, a network betweeness feature, a network degree feature, or a loss of function mutation frequency feature.

In some implementations, the machine learning classifier is a random forest classifier. The random forest classifier can include between about 25 and 5000 decision trees. The random forest classifier can include between about 50 and 1000 decision trees. The random forest classifier can include between about 50 and 500 decision trees.

In some implementations, the data processing system is configured to provide a random portion of a first plurality of values from the first structural vector to a first portion of the decision trees. The data processing system can be configured to provide a random portion of a second plurality of values from the first target vector to a second portion of the decision trees.

In some implementations, the data processing system can determine, for each of the decision trees, a score indicating a relationship to the adverse effects threshold. The data processing system can generate the toxicity predictor score based on the score from each of the decision trees.

The first plurality of reference chemicals can include a plurality of drugs that passed clinical trials and the second plurality of reference chemicals includes a plurality of drugs that failed clinical trials.

The data processing system can be configured to determine the at least one gene target for the first chemical based on the chemical structure of the first chemical.

According to another aspect of the disclosure, a method to improve the accuracy of drug toxicity predictions can include determining a first structural vector of a first chemical based on a chemical structure of the first chemical. The first structural vector can include values corresponding to one or more features derived from the chemical structure of the first chemical. The method can include determining a first target vector of the first chemical based on at least one gene target for the first chemical. The first target vector can include values corresponding to one or more features derived from the at least one gene target and the first chemical. The method can include generating, using a machine learning classifier, a toxicity predictor score for the first chemical.

The machine learning classifier can be trained using a first plurality of reference chemicals and a second plurality of reference chemicals. Each first reference chemical of the first plurality of reference chemicals can be identified as belonging to a first class known to demonstrate adverse effects below an adverse effects threshold and having a respective structural vector including values corresponding to one or more features derived from the chemical structure of the respective first reference chemical and a respective target vector including values corresponding to one or more features derived from one or more gene targets and the respective first reference chemical. Each second reference chemical of the second plurality of reference chemicals identified as belonging to a second class known to demonstrate adverse effects above the adverse effects threshold and having a respective structural vector including values corresponding to one or more features derived from the chemical structure of the respective second reference chemical and a respective target vector including values corresponding to one or more features derived from one or more gene targets and the respective second reference chemical.

The method can include comparing the toxicity predictor score for the first chemical to the adverse effects threshold. The method can include providing, responsive to determining that the toxicity predictor score for the first chemical is below the adverse effects threshold, a prediction that the first chemical will demonstrate adverse effects below the adverse effects threshold.

In some implementations, the structural vector can include at least one chemical property feature and at least one drug-likeness feature. The at least chemical property feature can include a polar surface area, a molecular weight, a hydrogen bond donor count, a hydrogen bond acceptor count, a charge number, or a number of rotatable bonds. The at least one drug-likeness feature can include a quantitative estimate of drug-likeness (QED), a rule of five measure, a Veber rule measure, or a Ghose rule measure.

The target vector can include at least one of a tissue expression feature or a target feature. The tissue expression feature can indicate a level of gene expression in a gene target tissue based on an exposure to the first chemical. The gene target tissue can be at least one of liver tissue, heart tissue, kidney tissue, or brain tissue. The target feature can include at least one of a network connectivity feature, a network betweeness feature, a network degree feature, or a loss of function mutation frequency feature.

The method can include generating the toxicity predictor score with a random forest classifier. The random forest classifier can include between about 25 and 5000 decision trees, between about 50 and 1000 decision trees, or between about 50 and 500 decision trees.

In some implementations, the method can include providing a random portion of a first plurality of values from the first structural vector to a first portion of the decision trees. The method can include providing a random portion of a second plurality of values from the first target vector to a second portion of the decision trees.

In some implementations, the method can include determining, for each of the decision trees, a score indicating a relationship to the adverse effects threshold. The method can include generating the toxicity predictor score based on the score from each of the decision trees.

In some implementations, the first plurality of reference chemicals can include a plurality of drugs that passed clinical trials and the second plurality of reference chemicals includes a plurality of drugs that failed clinical trials. The method can include determining the at least one gene target for the first chemical based on the chemical structure of the first chemical.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 14A-14D illustrate different performance metrics of the system.

FIG. 20 is an example representation of a data structure for chemical data that can be used in the system of FIG. 19.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein.

Section B describes embodiments of systems and methods to improve the accuracy of drug toxicity predictions.

Section C describes embodiments of systems and methods to predict tissue specific drug reactions.

Section D describes embodiments of systems and methods for computational analysis to predict binding targets of chemicals.

A. Computing and Network Environment

Figure 1A:
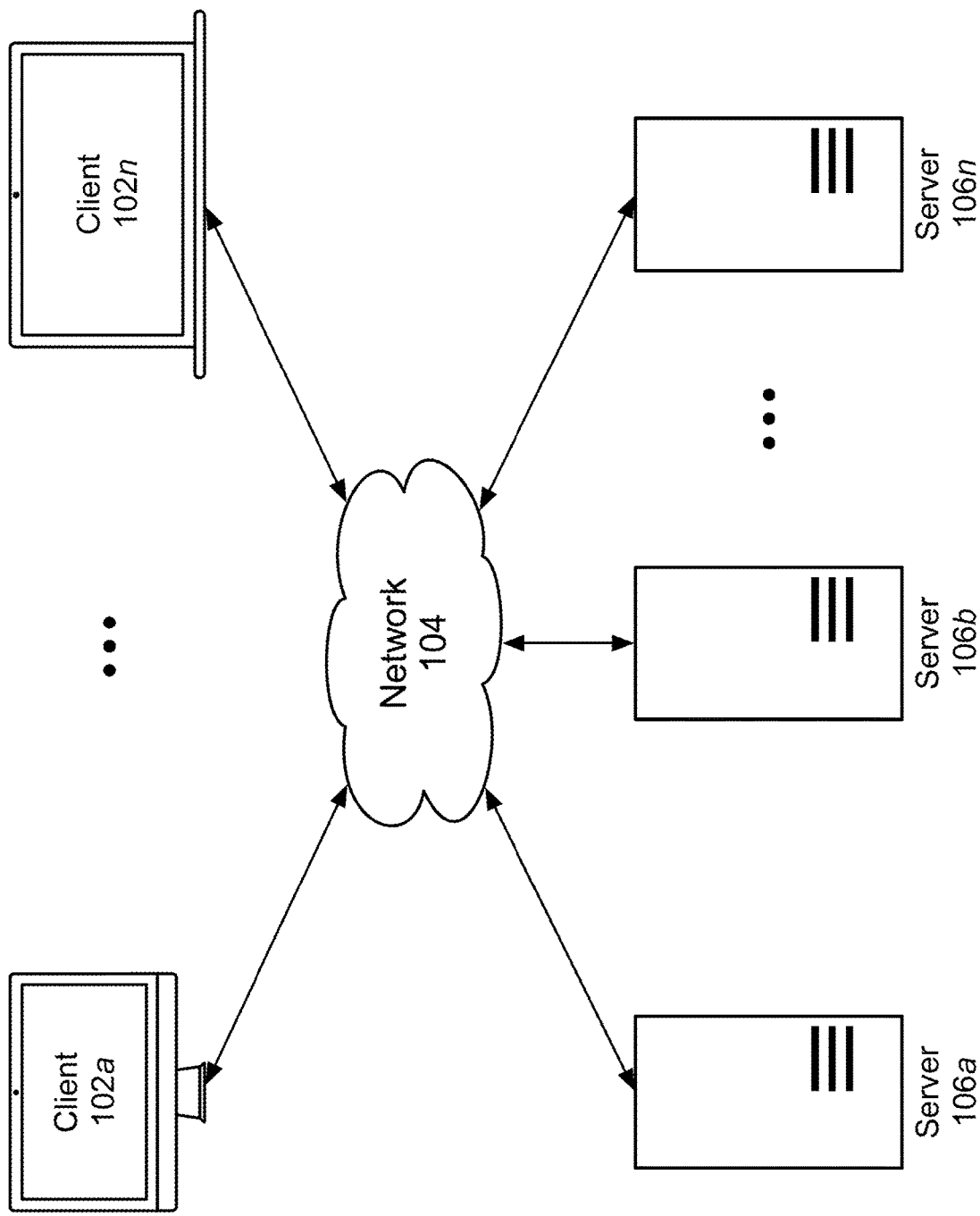
FIG. 1A is a block diagram depicting an embodiment of a network environment comprising a client device in communication with a server device.

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although, FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 (not shown) or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high-performance storage systems on localized high-performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
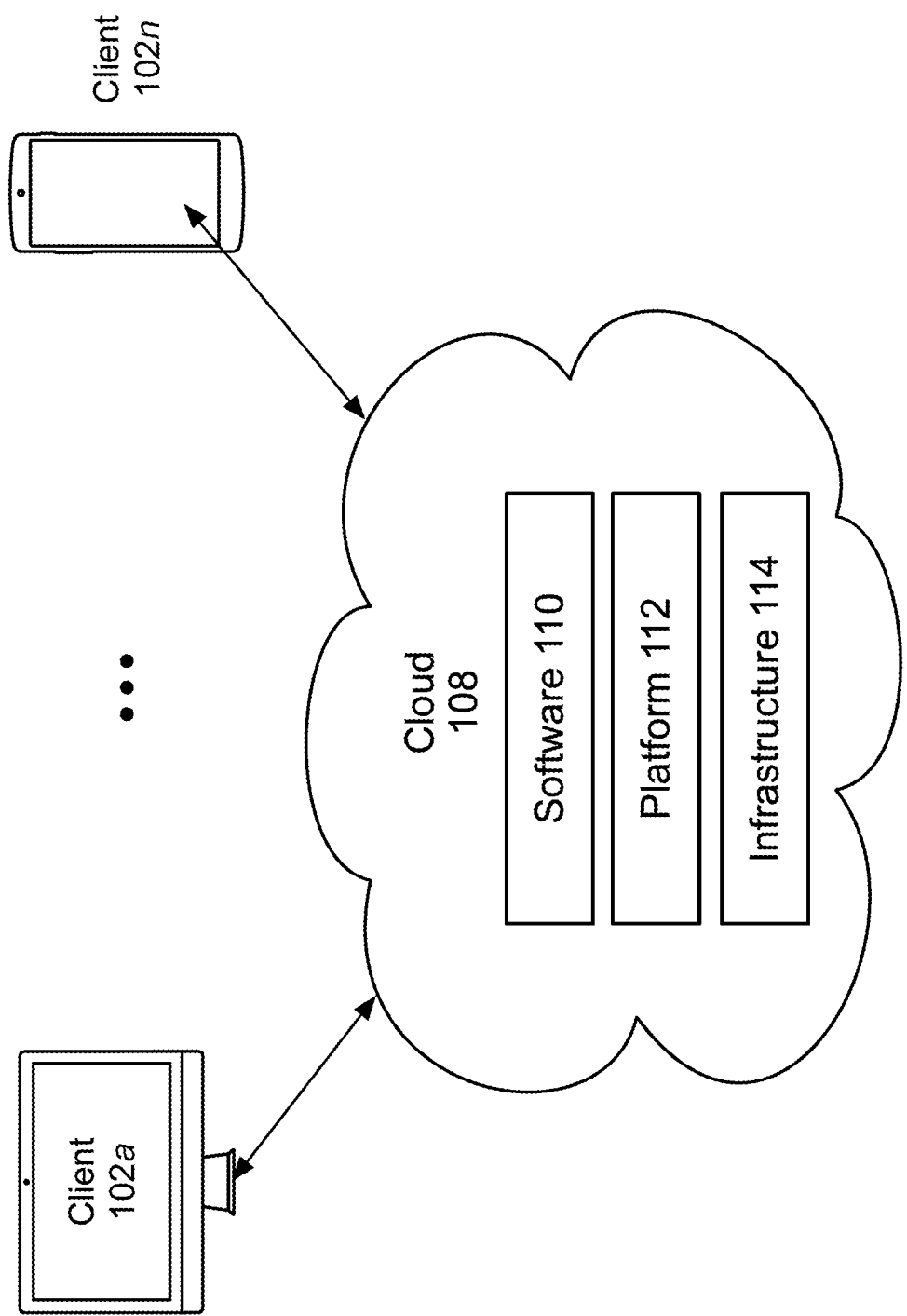
FIG. 1B is a block diagram depicting a cloud computing environment comprising a client device in communication with cloud service providers.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
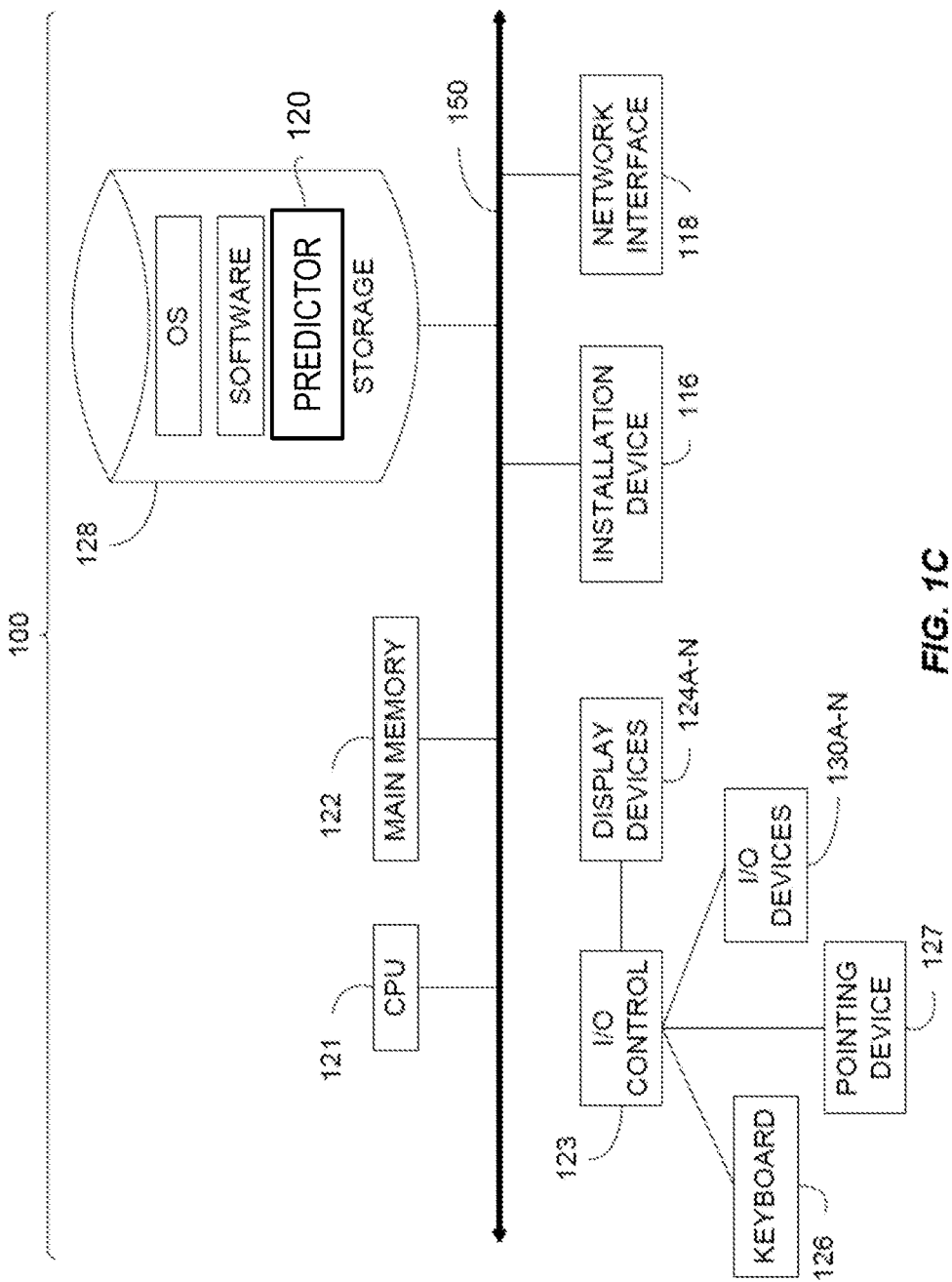
FIGS. 1C and 1D are block diagrams depicting embodiments of computing devices useful in connection with the methods and systems described herein.
Figure 1D:
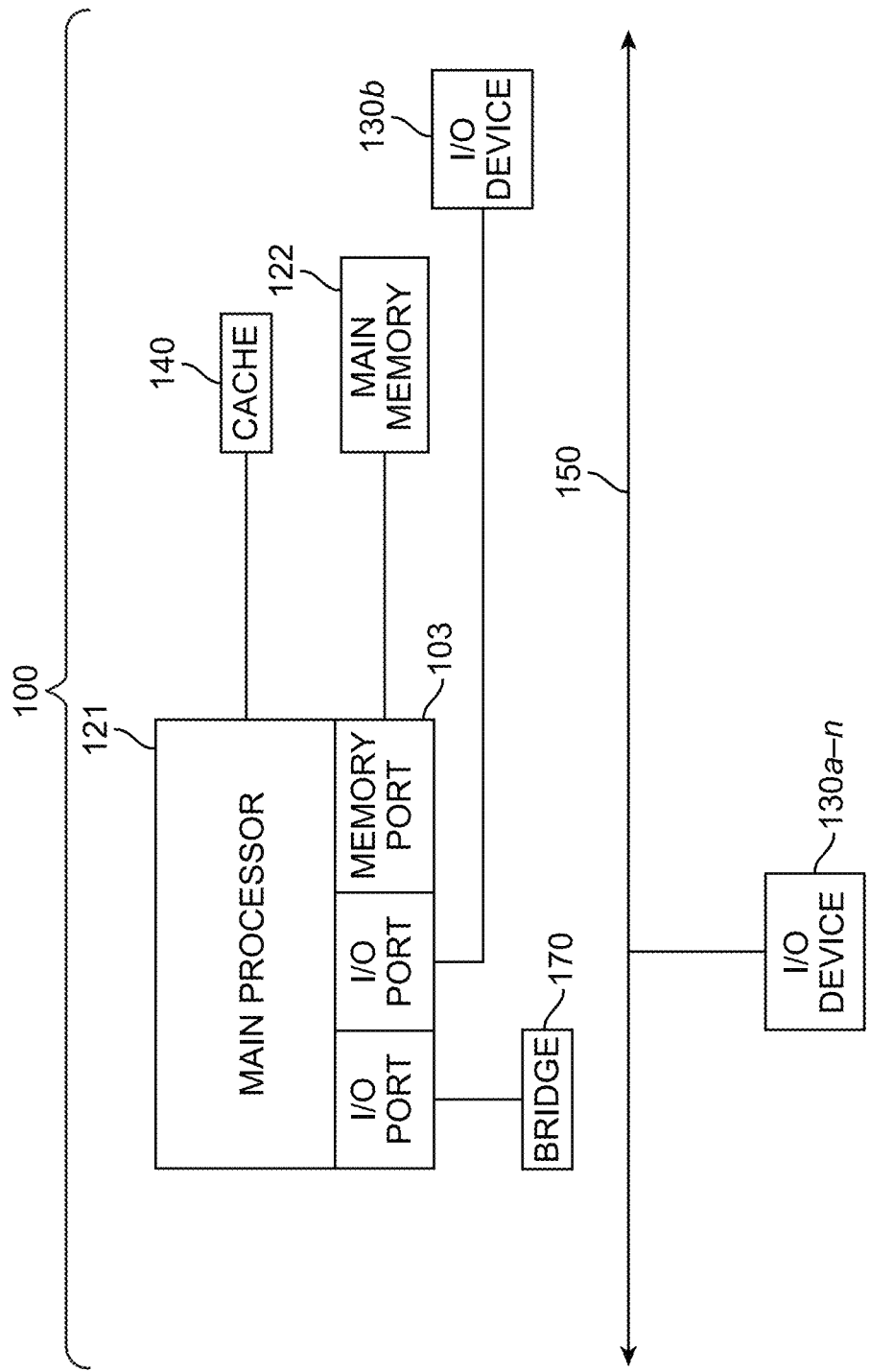

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of blur detector 120 and saliency detector 414. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random-access memory (DRAM) or any variants, including static random-access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAIVI), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touch-screen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopic. Display devices 124a-124n may also be a head-mounted display (HIVID). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the drug toxicity predictor 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections).

In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2002, WINDOWS CE, WINDOWS Phone, WINDOWS XP, WINDOWS VISTA, WINDOWS 7, WINDOWS RT, WINDOWS 8 and WINDOWS 10, all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is an eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Systems and Methods to Improve the Accuracy of Drug Toxicity Predictors

In some implementations, the present solution can generate toxicity profiles for test chemicals based on the results from past clinical trials. For example, the system can compare the test chemical with a first group of drugs that have failed clinical trials and a second group of drugs that have passed clinical trials (e.g., drugs that received Food and Drug Administration (FDA) approval) to determine similarities between the test chemical and the first and second groups. The system can retrieve data, such as from The Database for Aggregate Analysis from ClinicalTrials.gov (AACT), and extract the names of the drugs associated with clinical trials of any phase that were annotated as having failed for toxicity reasons.

The system can generate predictions that can outperform existing methods in their ability to distinguish approved drugs from those that failed for toxicity in trials (FTT drugs). For example, most FDA approved drugs pass Lipinski's Rule of Five (80.6%) and Ghose's (64.9%) rules, but so do most of the FTT drugs (73% Lipinski, 54% Ghose). In contrast, Veber's rule appears to be a far too conservative measure, with 75.2% of approved and 92% of FTT drugs being predicted to fail. Finally, the QED approach, which calculates a continuous score, is also unable to significantly distinguish the two classes (p=0.1069, D=0.10703, Kolmogorov-Smirnov Test).

The present solution can include overlooked features related to the results of a drug's performance to provide impactful results about clinical safety.

The present solution can integrate informative chemical features of the drugs with target-based features to produce a classifier that is able to distinguish FDA approved drugs from FTT drugs. The system can include a random forest, a decision tree based machine learning model, to address the classification problem of clinical trial drug toxicity. The system can integrate chemical properties features, drug-likeness features, and target-based features of a molecule into a random forest model to predict whether the drug is likely to fail clinical trials for toxicity reasons.

Figure 2:
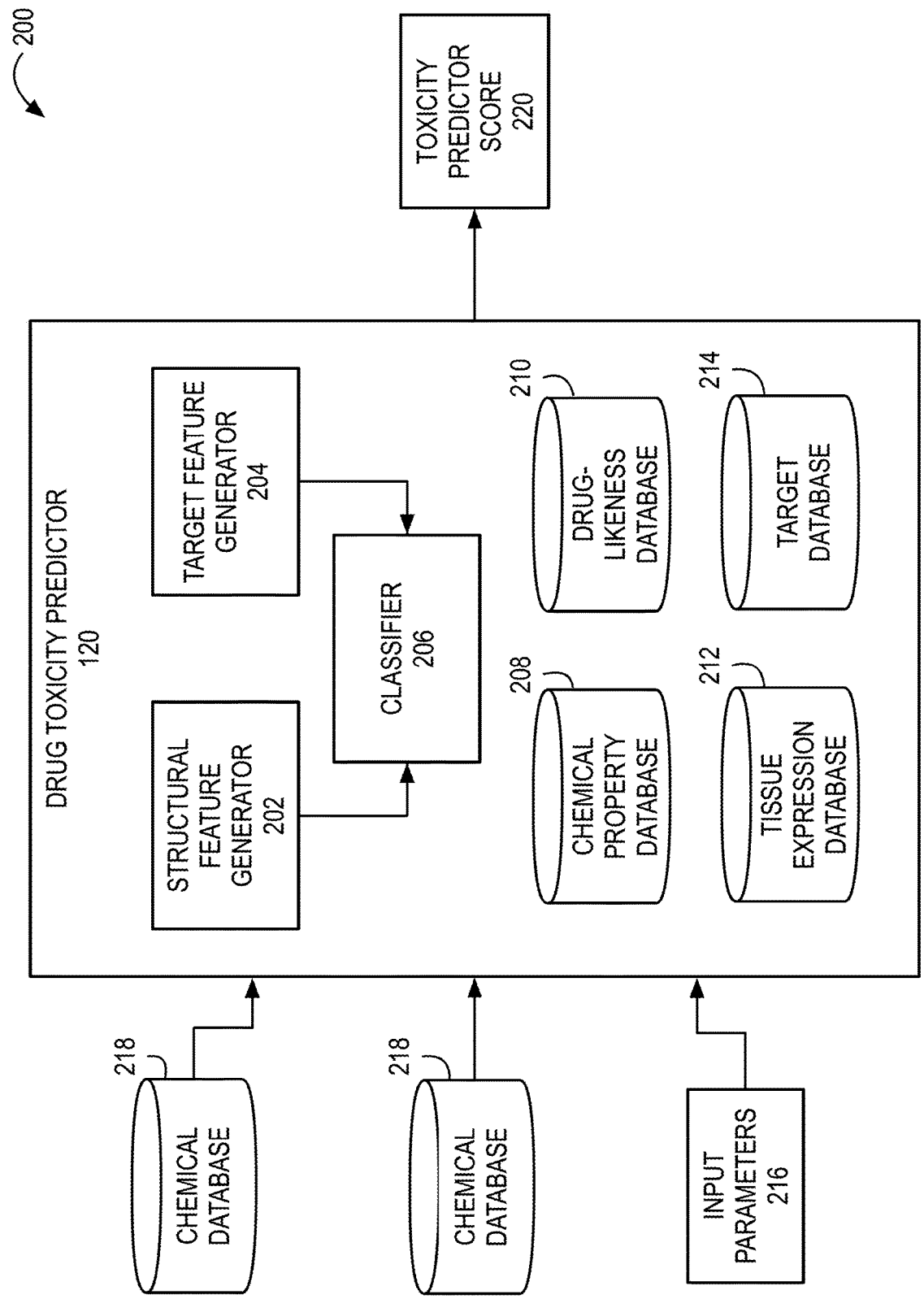
FIG. 2 illustrates a block diagram of an example system to increase the accuracy of drug toxicity predictors.

FIG. 2 illustrates a block diagram of an example system 200 to improve the accuracy of drug toxicity predictions. The system 200 includes a drug toxicity predictor 120. The drug toxicity predictor 120 includes a structural feature generator 202 and a target feature generator 204 that supply input vectors to a classifier 206. The drug toxicity predictor 120 can also include a chemical property database 208, a drug-likeness database 210, a tissue expression database 212, and a target database 214. The drug toxicity predictor 120 can receive input parameters 216 and additional inputs from one or more chemical databases 218. The drug toxicity predictor 120 can output a toxicity predictor score 220.

The structural feature generator 202 and the target feature generator 204 can calculate structural vectors and target vectors, respectively, for input and reference chemicals or drugs. Each of the structural vectors and target vectors can include values that are derived from one or more categories of features. The structural feature generator 202 can calculate values for the structural vector based on chemical properties and drug-likeness features of the input test chemicals. The target feature generator 204 can calculate values for the target vector based on gene expression features for one or more specific tissues and other target-based features.

The structural feature generator 202 and the target feature generator 204 can generate a structural vector and target vector for the input test chemical based on inputs received as input parameters 216, data retrieved from external chemical databases 218, other databases (e.g., the chemical property database 208, drug-likeness database 210, tissue expression database 212, or target database 214). The chemical property database 208, drug-likeness database 210, tissue expression database 212, and target database 214 can be stored local to the drug toxicity predictor 120 or can be coupled with the drug toxicity predictor 120 via a network or other remote connection. The chemical databases 218 can be remote databases that the drug toxicity predictor 120 can access via a network. Example chemical databases 218 can include the DrugBank database, the Genotype-Tissue (GTEx) project database, and the Exome Aggregation Consortium (ExAC) database.

The drug toxicity predictor 120 can receive input parameters 216. The input parameters 216 can include the name of a chemical, the chemical structure of the chemical, an image of the chemical's structure, or any combination thereof. The input parameters 216 can also include indications of known chemical targets, drug-likeness features, expression data, or any combination thereof. In some implementations, the drug toxicity predictor 120 can retrieve data from the chemical databases 218 and calculate toxicity predictor scores and target vectors that the drug toxicity predictor 120 can store into one of the chemical property database 208, drug-likeness database 210, tissue expression database 212, or target database 214. The target vector and structural vector can be calculated responsive the drug toxicity predictor 120 receiving the input parameters 216. In some implementations, the drug toxicity predictor 120 can pre-calculate one or more of the target vector and structural vector prior to receipt of the input parameter 216. For example, the drug toxicity predictor 120 can calculate the features for each of the chemicals listed in the chemical databases 218.

The structural feature generator 202 can calculate or determine chemical property features of the input chemical and store the features in the chemical property database 208. The structural feature generator 202 can calculate drug-likeness features and store the features in the drug-likeness database 210. The target feature generator 204 can calculate tissue expression features and store the features in the tissue expression database 212. The target feature generator 204 can calculate target features and store the features in the target database 214.

For example, the target feature generator 204 can annotate a drug's known targets from the DrugBank dataset (an example chemical database 218), and the target feature generator 204 can derive a set of target-based features from the drug's known targets. The target feature generator 204 can generate target-based features for a plurality of different target tissues. For example, the target feature generator 204 can calculate a median expression of the gene targets in 30 different tissues. The tissues can include the liver tissue, heart tissue, kidney tissue, lung tissue, pancreas tissue, blood, or brain tissue. The target feature generator 204 can calculate tissue expression features based on data retrieved from the Genotype-Tissue Expression (GTEx).

The structural feature generator 202 can retrieve the chemical's structure (e.g., in a sdf format) from the DrugBank. Based on the structure, the structural feature generator 202 can determine the molecular weight, polar surface area, hydrogen bond donor and acceptor counts, formal charge, and number of rotatable bounds for the chemical. These features can be used as values in the structural vector or the values of the structural vector can be based on the features. In some implementations, the structural feature generator 202 can retrieve the information from a secondary chemical database 218, such as PubChem. In some implementations, the structural feature generator 202 can computationally estimate one or more of the chemical property features using ChemmineR in R.

The structural feature generator 202 can use the chemical property features as inputs into calculating one or more of the drug-likeness features. For example, the Lipinski's Rule of Five feature (a drug-likeness feature) can be calculated based on chemical properties, such as, the number of hydrogen bond donors, the number of hydrogen bond acceptors, a molecular mass of the chemical, and an octanol-water partition coefficient of the chemical. One or more of these features can be included as values in the structural vector. Or, one or more of the values in the structural vector can be based on the features.

In some implementations, the target feature generator 204 can calculate other target-based features such as, but not limited to, a network connectivity of the target, a gene degree feature, a betweenness feature, or a feature that represents the loss of function mutation frequency in the target gene. In some implementations, the target feature generator 204 can calculate the loss of function mutation frequency feature with data retrieved from the Exome Aggregation Consortium (ExAC) database. The values of the target vector can be derived from (or can be) the target-based features.

In some implementations, additional features that the classifier 206 can use to determine the toxicity predictor score 220 are discussed in Section D, below, such as known drug indications, known drug interactions, drug dosing information, mass spectrometry images, fluorescence/microscopy images, electronic health record data, gene expression and efficacy data in cells following genetic perturbation, and drug binding efficiencies.

The drug toxicity predictor 120 can include a classifier 206 that can make a prediction of whether the input chemical is toxic or non-toxic. The classifier 206 can generate a toxicity predictor score 220 for the input chemical that can indicate whether the input chemical is likely to cause adverse events above or below a predetermined adverse effects threshold. For an input chemical, the structural feature generator 202 and the target feature generator 204 can provide a structural vector and a target vector, respectively, to the classifier 206 or the classifier 206 can retrieve the structural vector and the target vector from the databases 208-214.

In some implementations, the classifier 206 can use both structural vectors and target vectors in the classification of the input chemical. The structural vectors and the target vectors can each be a composite of different structural features and target features, respectively. For example, a structural vector can include (or be based on) values, such as the molecular weight, polar surface area, and formal charge. In this example, each of the different structural features can be indicated as one or more values in the structural vector.

The classifier 206 can be trained using different reference chemicals. The drug toxicity predictor 120 can receive data about the reference chemicals from the chemical databases 218. In some implementations, a first group of the reference chemicals can belong to a class of drugs known to demonstrate adverse effects below an adverse effects threshold. For example, the drugs can cause side effects that are acceptable to a patient given the benefits the drugs provide to the patient. For example, the first class can include drugs that passed clinical trials. In on example, a drug that cures or treats a life-threatening disease can have a higher relative adverse effects threshold than a drug that treats a non-life threatening disease because a patient with a life threatening disease will accept a higher level of side effects when treating their disease. The reference chemicals can include a second group of reference chemicals that belong to a class of drugs that are known to demonstrate adverse effects above an adverse effects threshold or that have failed clinical trials.

For each of the reference chemicals, the structural feature generator 202 can calculate structural vectors that can include values corresponding to one or more features derived from the chemical structure of the respective reference chemical. The target feature generator 204 can calculate a respective target vector for each of the reference chemicals that can include values corresponding to one or more features derived from one or more gene targets of the respective reference chemical. In some implementations, the structural vectors and the target vector are concatenated into a single input vector.

In some implementations, both the chemical and target-based features can contribute to the performance of the classifier 206. In some implementations, the structural vector can include a first expression principle component, QED metric, polar surface area, and the drug target's network connectivity. In some implementations, the classifier 206 can select to use features that are uncorrelated with one another.

Figure 3B:
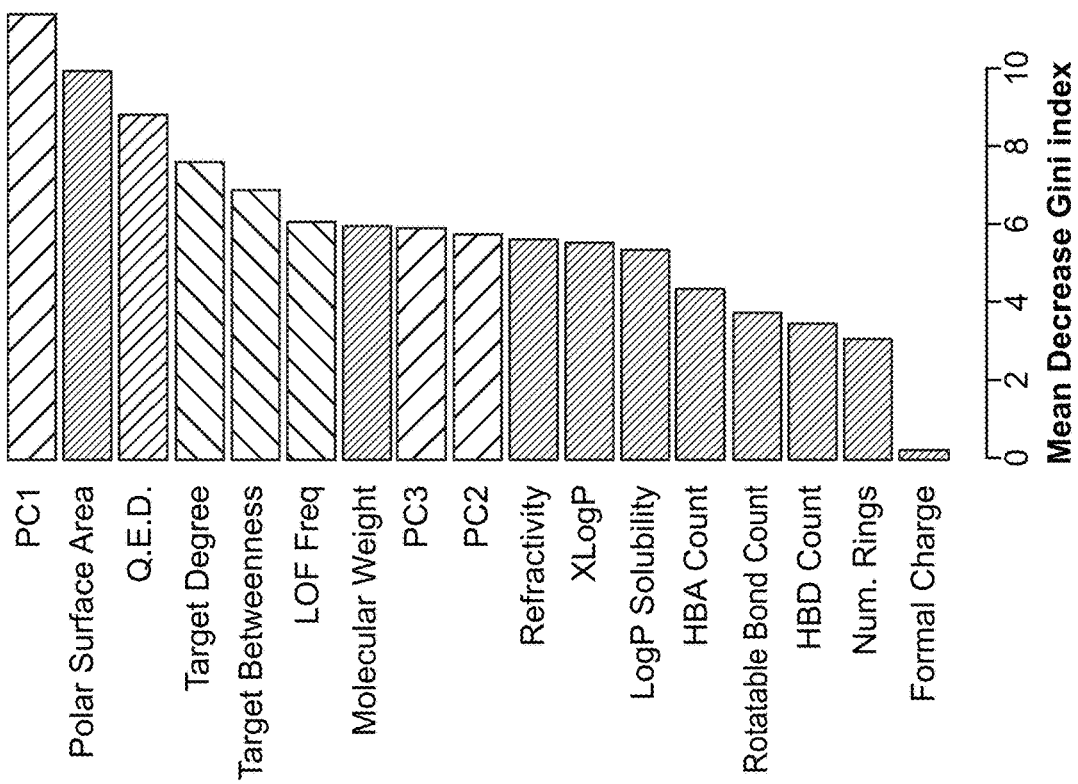
FIGS. 3A and 3B illustrate a ranking of each of the feature impact on calculating accurate toxicity scores.
Figure 3A:
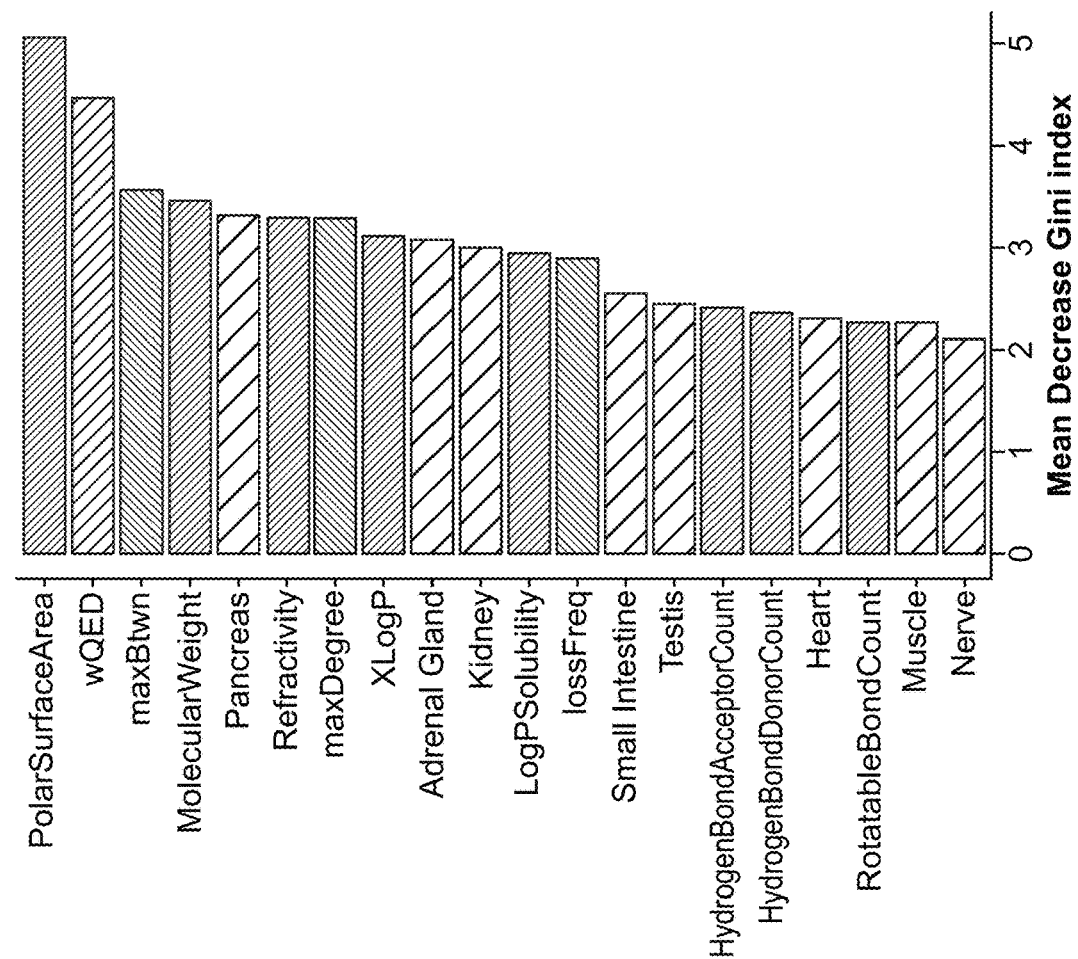

FIGS. 3A and 3B illustrate a ranking of each of the feature impact on calculating accurate toxicity scores 220. The FIGS. 3A and 3B illustrate the importance of including both chemical and target-based features when calculating the toxicity predictor score 220. For example, using target-based features alone, the drug toxicity predictor 120 achieved a significant predictive performance (ACC=0.7115). The drug toxicity predictor 120 can use existent annotation of drug targets to calculate these features. However, this information is often not available during the drug development stage. The drug toxicity predictor can be robust to removal of targets, as illustrated in FIG. 3B, and can maintain a high predictive performance (ACC=0.6708) in absence of known target information.

In some implementations, certain combinations of uncorrelated features provided greater discriminative power. For example, the QED approach can outperform other drug-likeness methods when the threshold was set at 0.35. However, when high testis expression was added into consideration, 88.5% of FTT drugs were accurately classified. Additionally, tissue selectivity can be a useful consideration in determining potential toxic effects. This may be due to some tissue-specific toxicity events being associated with the drug target's expression in normal tissue. The drug toxicity predictor 120 found that 84% (38/45) of drugs with high molecular weight (e.g., above 500) but low general tissue expression (e.g., a PC1 below −2) were FDA approved. Thus, if a gene appears to be a promising target for mechanistic reasons while appearing ill-suited due to high global expression profiles, it still may remain a viable candidate given that certain molecular properties are satisfied.

The classifier 206 can include a random forest classifier. The random forest classifier can include between about 25 and about 5000 decision trees, between about 50 and about 1000 decision trees, or between about 50 and about 500 decision trees. Once trained, each of the decision trees can make output a binary prediction of whether the input chemical is toxic or non-toxic (or above or below an adverse effects threshold). The classifier 206 can generate different random subsets of values from the structural and target features. The different random subsets of values can be input to each of the different decision trees.

The classifier 206 can generate a toxicity predictor score 220. The classifier 206 can include a plurality of decision trees that can each generate binary (toxic or non-toxic) classifications for the input chemical. In some implementations, the toxicity predictor score 220 can be a binary result (e.g., toxic or non-toxic). The classifier 206 can determine a binary result for the toxicity predictor score 220 by determining if there are a greater number of toxic or non-toxic results from the decision trees. For example, if a majority of the decision trees return a result that the chemical is non-toxic, the classifier 206 can generate a toxicity predictor score 220 for the chemical that the chemical is non-toxic.

In some implementations, the toxicity predictor score 220 can be a numerical score. For example, a toxicity predictor score 220 expressing the $\log_2$ (odds of approval) can be calculated taking the $\log_2$ of the ratio of the non-toxic to toxic decisions by the decision trees.

In one example, the structural feature generator 202 and the target feature generator 204 can calculate a set of 48 features (e.g., an input vector generated by concatenating a structural vector and a target vector includes 48 values). The structural feature generator 202 and the target feature generator 204 can provide the 48 features to the classifier 206.

Figure 3C:
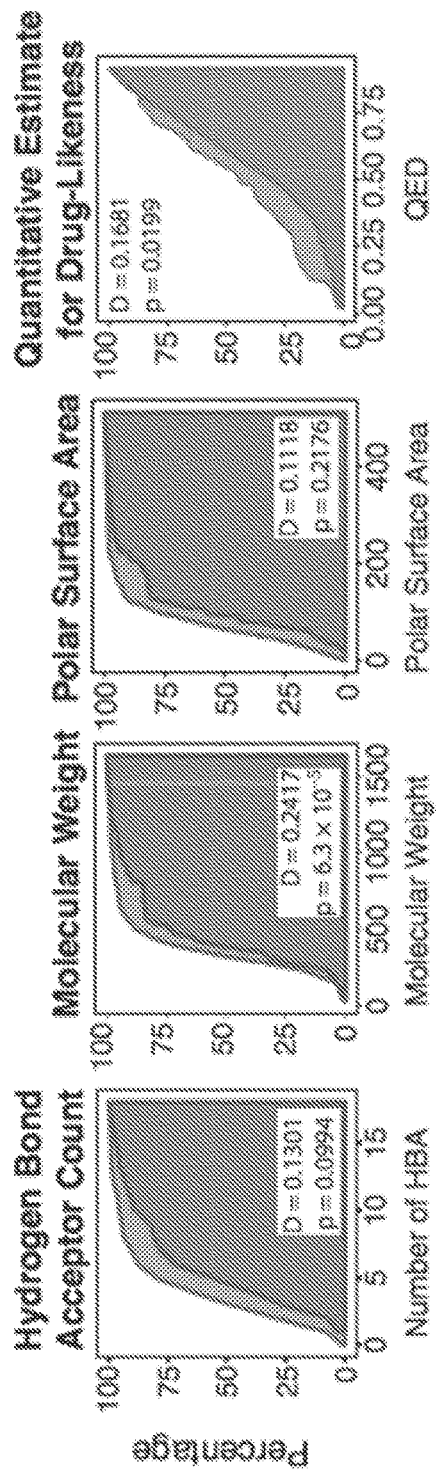
FIG. 3C illustrates distributions of select chemical features.
Figure 3D:
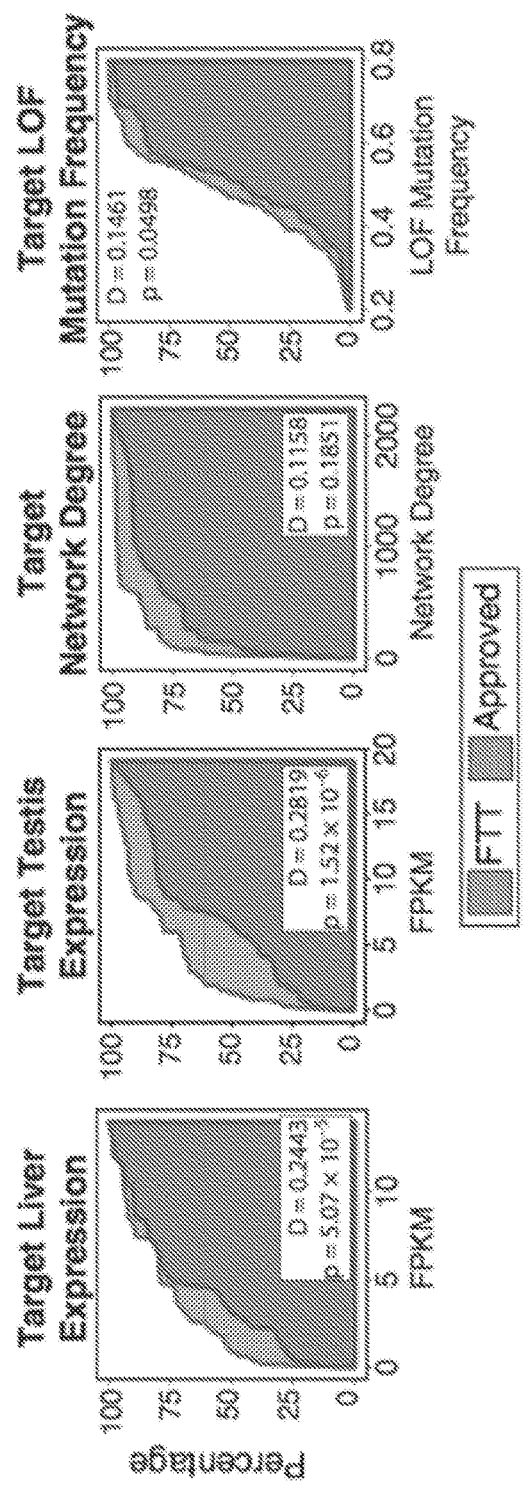
FIG. 3D illustrates target-based model features.

The 48 features can include 10 chemical features, 34 target-based features, and 4 drug-likeness rule features. FIG. 3C illustrates distributions of four chemical features. FIG. 3D illustrates four target-based features. The Kolmogorov-Smirnov D statistic and p-value are shown for the comparison of FTT drugs and FDA approved drugs. FIG. 3C illustrates that some features had slight but significant power to discriminate between FDA approved drugs and FTT drugs. Additional features represent the compatibility of the chemicals with the drug-likeness approaches. Each drug's known targets were annotated from the DrugBank dataset and used to derive an additional set of target-based properties. The system can consider the median expression of the gene targets in 30 different tissues, such as the liver and the brain, calculated from the Genotype-Tissue Expression (GTEx) project.

Other target-based features represent the network connectivity of the target, with gene degree and betweenness features, computed using an aggregated gene-gene interaction network, and a feature that represents the loss of function mutation frequency in the target gene, extracted from the Exome Aggregation Consortium (ExAC) database. FIG. 3D illustrates that like the chemical properties, some of these target-based features can also discriminate between FDA approved drugs and FTT drugs. Many of the features within the target-based or the chemical category were highly correlated with each other. For example, the target expression values can be highly correlated. In some implementations, the drug toxicity predictor 120 can perform a principle component analysis to all target expression values to reduce the feature dimensionality. In place of the raw expression feature values, the target feature generator 204 can use the first three principle components. In some implementations, the target-based features can add information independent of the chemical features.

In one example, the drug toxicity predictor 120 was tested by performing a 10-fold cross validation on a set of 784 FDA approved drugs with known targets and a second set of 100 FTT drugs that had at least one annotated target and known chemical structure. FIGS. 4A-4F illustrate bench marking of the drug toxicity predictor's performance.

Figure 4A:
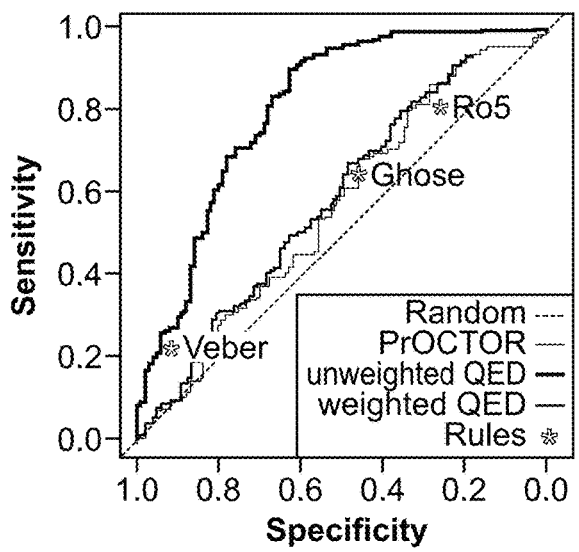
FIG. 4A illustrates receiver operating characteristic (ROC) curves for the system, three drug-likeness rules, and both the weighted and unweighted QED metrics.

FIG. 4A illustrates operating characteristic (ROC) curves for the drug toxicity predictor 120 using three drug-likeness rules (the rule of five (Ro5), Veber, Ghose), a weighted QED metric, and an unweighted QED metric. FIG. 4A illustrates the predictive performance of the drug toxicity predictor 120. The area under the receiver operator curve (AUC) is 0.8263. At the optimal point on the curve, the drug toxicity predictor 120 achieved an accuracy (ACC) of 0.7529. The drug toxicity predictor 120 had both a high sensitivity (true positive rate (TPR) of 0.7544) and a high specificity (true negative rate (TNR) of 0.7410). By comparison, on this same dataset the Ro5 and Ghose rules had a TPR of 0.8030 and 0.6468, respectively, and a TNR of 0.27 and 0.46, respectively. Application of the Veber method achieved a TPR of 0.2465 and a TNR of 0.92. The ROC curve of both the unweighted and weighted versions of the QED method fell significantly below that of drug toxicity predictor's ROC curve, indicating that the drug toxicity predictor 120 is able to better distinguish the FTT and approved drug classes. Furthermore, the drug toxicity predictor's approval probability allows for the separation of the drugs of the FTT and FDA approved classes on a continuous scale.

Figure 4B:
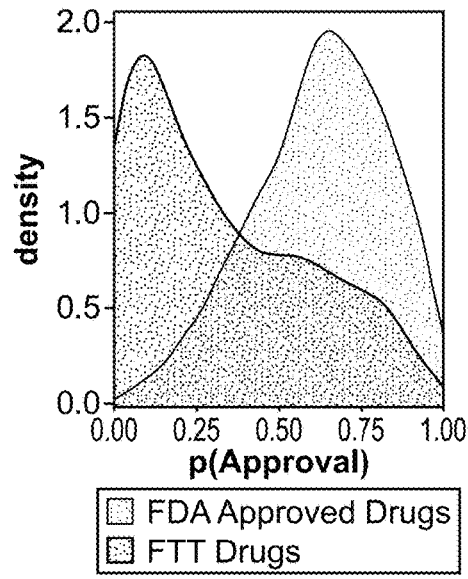
FIG. 4B illustrates scores and the QED metric for approved and failed toxic clinical trial (FTT) drugs.
Figure 4C:
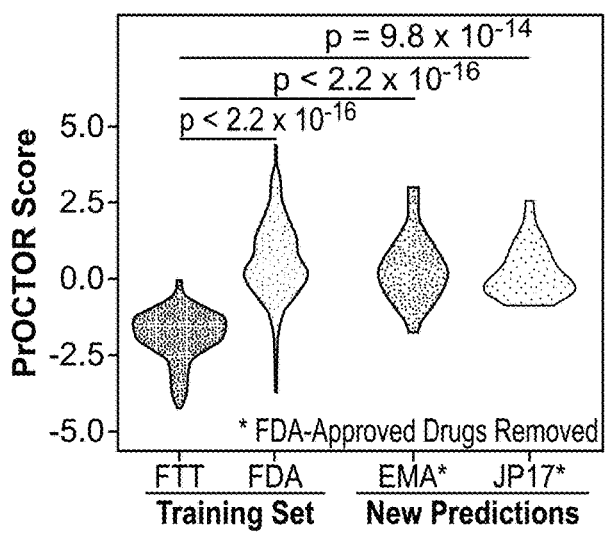
FIG. 4C illustrates scores for the FDA approved and FTT drugs in the training set, as well as EMA-Approved and Japanese-Approved (JP17) drugs after removal of FDA approved drugs. Statistical significance was assessed for FDA, EMA, and JP17 vs. FTT drugs using the Mann-Whitney U Test.
Figure 4D:
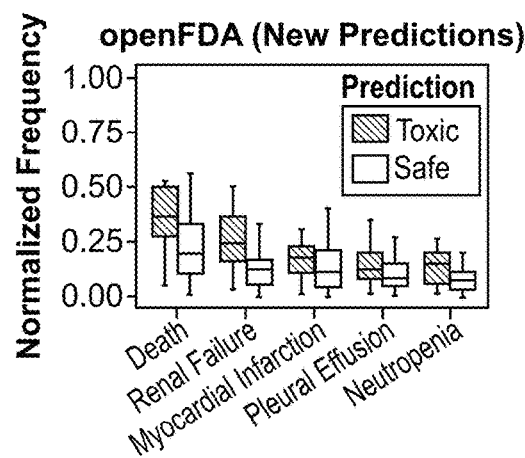
FIG. 4D illustrates reported frequencies, normalized to the most frequently reported adverse event, in the openFDA database for predicted toxic (red, score<−1) and predicted safe drugs from the DrugBank dataset.

FIG. 4B illustrates the system's scores and the QED metric for FDA approved and FTT drugs. FIG. 4C illustrates scores for the FDA approved and FTT drugs in the training set, as well as EMA-Approved and Japanese-Approved (JP17) drugs after removal of FDA approved drugs. FIG. 4D illustrates reported frequencies, normalized to the most frequently reported adverse event, in the openFDA database for predicted toxic and predicted safe drugs from the DrugBank dataset.

FIG. 4C illustrates the results from applying the system to drugs that are approved in Europe (EMA-Approved) or in Japan (JP17) but not annotated as being FDA approved in our dataset. The system compared to the FTT drugs in the training set, and provided that EMA-Approved (p=2.2e-16, Mann-Whitney U Test) and JP17 drugs (p=9.84e-14, Mann-Whitney U Test) were predicted to be significantly safer and had a similar distribution of systems scores to the class of FDA Approved Drugs.

FIG. 4D illustrates additional example results calculated by the drug toxicity predictor 120. In this example, 3,236 drugs that were in the DrugBank database and not in the training set were provided to the drug toxicity predictor 120. The drug toxicity predictor 120 found that the predicted toxic drugs had significantly more frequent reports of serious adverse events, such as death and renal failure, than predicted safe drugs in the openFDA database of drug adverse events. The drug toxicity predictor 120 determined that safe predictions were enriched for classes of drugs that are known to be relatively safe, such as antidepressants, stimulants, and serotonin-related drugs. In comparison, toxic predictions were enriched for known toxic classes of drugs, such as immunosuppressive agents and antineoplastic agents.

In another example illustrating that the drug toxicity predictor 120 can be generalized beyond the training drugs, the drug toxicity predictor 120 made predictions on 137 drugs annotated by the FDA as possibly causing a Drug-Induced liver injury (DILI) and 65 drugs annotated by the FDA as not having a DILI. The drug toxicity predictor 120 found that the DILI-annotated drugs had 1.5-fold higher odds of being classified as toxic the non-DILI-annotated drugs.

Figure 4E:
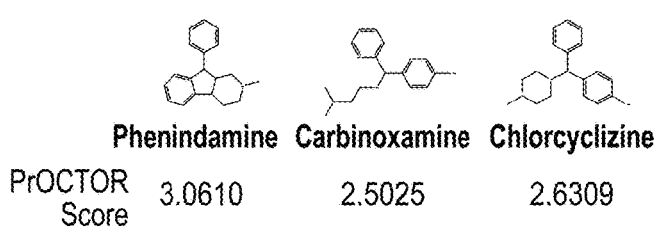
FIG. 4E illustrates the top three molecules predicted by the system as most likely to be FDA approved: phenindamine, carbinoxamine, and chlorcyclizine.
Figure 4F:
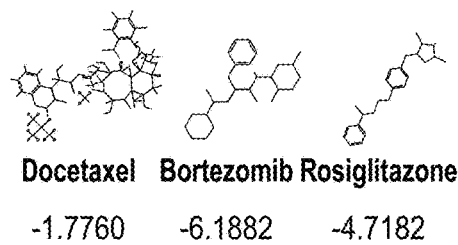
FIG. 4F illustrates the three molecules predicted by the system as most likely to fail clinical trials for toxicity reasons: docetaxel, bortezomib, and rosiglitazone.

FIG. 4E illustrates the chemical structure of the top three molecules predicted by the drug toxicity predictor 120 as most likely to be FDA approved. The molecules include phenindamine, carbinoxamine, and chlorcyclizine. FIG. 4F illustrates the chemical structure of the three molecules predicted by the system as most likely to fail clinical trials for toxicity reasons. The molecules most likely to fail the clinical trials are docetaxel, bortezomib, and rosiglitazone.

The three molecules identified by the system as most likely to receive FDA approval were phenindamine, carbinoxamine, and chlorcyclizine. All three of these drugs are FDA approved antihistamines with highly tolerable side effects. These results also illustrate that drug toxicity predictor 120 can more accurately screen drugs that standard screening procedures. For example, phenindamine, carbinoxamine, and chlorcyclizine can each pass the Ro5 but have relatively low QED values (0.311, 0.242, and 0.499 respectively).

The three molecules with the lowest toxicity predictor score 220 and thus predicted as the most likely to fail clinical trials for toxicity reasons were docetaxel, bortezomib, and rosiglitazone. Each of these drugs are FDA approved drugs that have been associated with serious toxicity events. Docetaxel is a chemotherapy agent used to treat a number of cancers. The most frequent adverse event associated with docetaxel is neutropenia, a potentially life threatening event that often results in delay of treatment. Bortezomib is a proteasome inhibitor used for treatment of relapse multiple myeloma that has a moderate QED value of 0.476, but passes the Ro5. While it was FDA approved due to its significant antitumor activity, it has been associated with frequent adverse events, such as peripheral neuropathy. These adverse events can be due, in part, to nonproteasomal targets. Rosiglitazone is an antidiabetic drug that also passes the Ro5 and has a high QED value of 0.825. However, it has been linked with an elevated risk of heart attack and consequently was withdrawn from the market in Europe in 2010. This suggests that existing methods were not necessarily able to foresee the adverse events associated with these latter two chemicals.

Figure 5B:
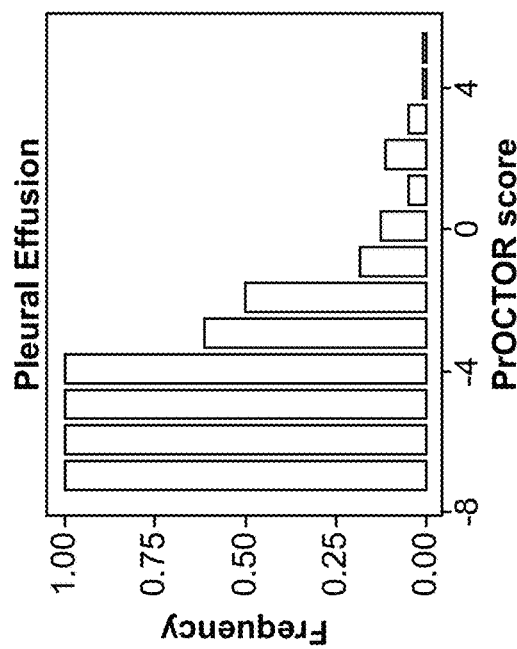
FIG. 5B illustrates the binned frequency of pleural effusion across score bins.
Figure 5C:
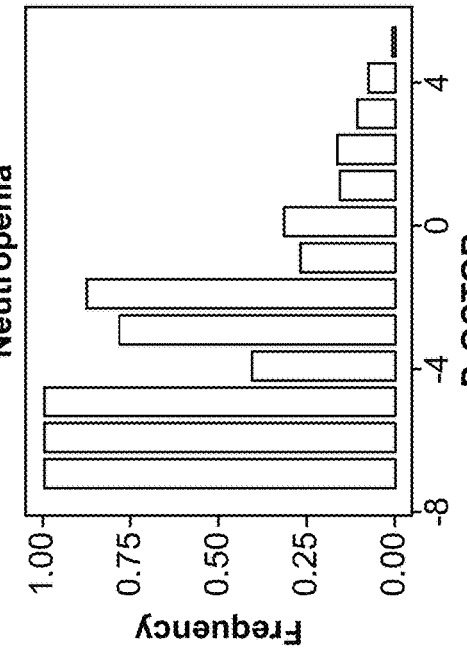
FIG. 5C illustrates the binned frequency of neutropenia across score bins.
Figure 5A:
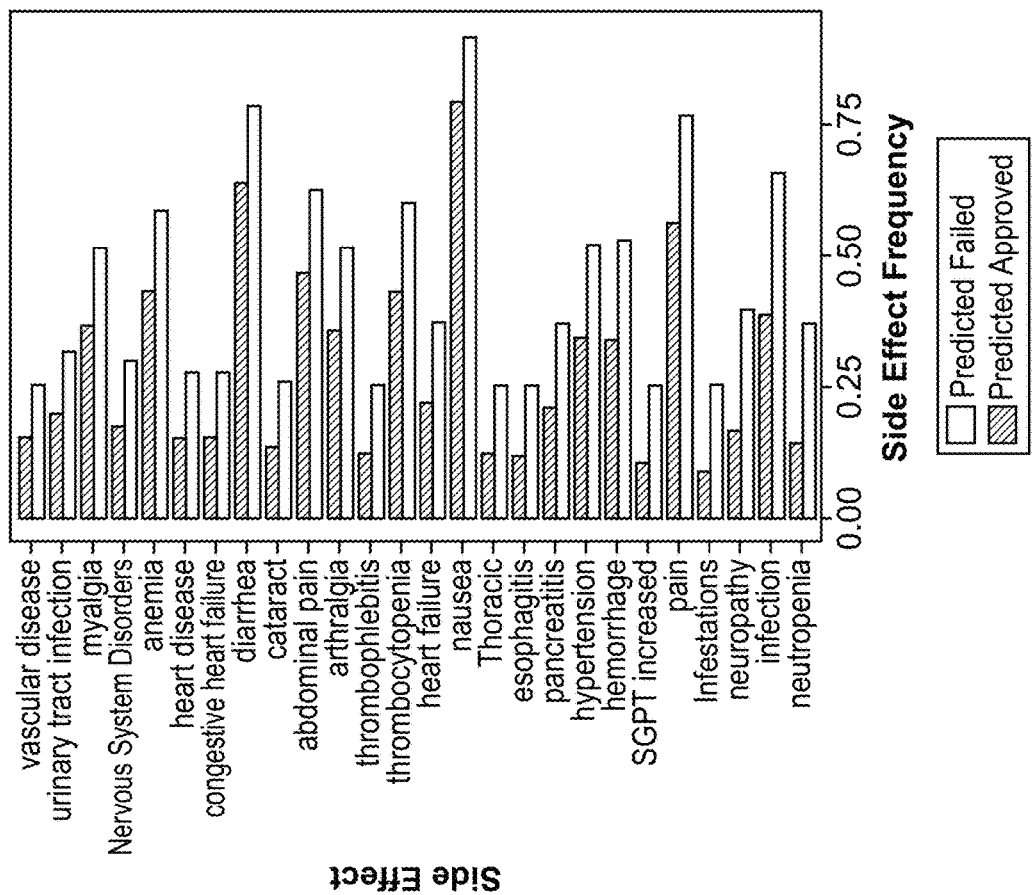
FIG. 5A illustrates adverse events that occur more frequently in predicted failed toxic clinical trial (FTT) drugs compared to predicted approved drugs.

In some implementations, drugs with a better toxicity predictor score 220 would have less frequent severe side effects reported due to their more tolerable toxicity profiles. The drug toxicity predictor 120 compared all drugs predicted to be approved by the classifier 206, including those misclassified, to those predicted to be of the toxic class. FIG. 5A illustrates that the predicted toxic drugs had significantly more frequent severe side effects, such as neutropenia (37.3% vs 14.3%, $p=1.78\times10^{-7}$, Fisher-Exact test). When comparing the drugs with the top 10% best toxicity predictor score 220 to those within the bottom 10% toxicity predictor score 220, this distinction was even greater with severe toxic events, such as neutropenia (54.8% vs 13.4%, $p=1.72\times10^{-6}$, Fisher-Exact test) and pleural effusion (47.6% vs 5.2%, $p=2.59\times10^{-7}$, Fisher-Exact test), occurring far more frequently in the predicted FTT class.

Furthermore, the drug toxicity predictor 120 can determine that these severe side effects can be negatively correlated with the toxicity predictor score 220. For example, FIGS. 5B and 5C illustrate that the spearman's correlation coefficient of the binned pleural effusion frequency against the toxicity predictor score 220 was $p=-0.9792$ (FIG. 5B) and for neutropenia the spearman's correlation coefficient against the toxicity predictor score 220 was $p=-0.9613$ (FIG. 5C). In comparison, the frequent side effect of dizziness still occurred more frequently in the predicted toxic drugs but had a much weaker correlation of $p-=0.5070$. FIGS. 5B and 5C illustrate that the calculated toxicity scores 220 are consistent with reported adverse events.

Figure 6:
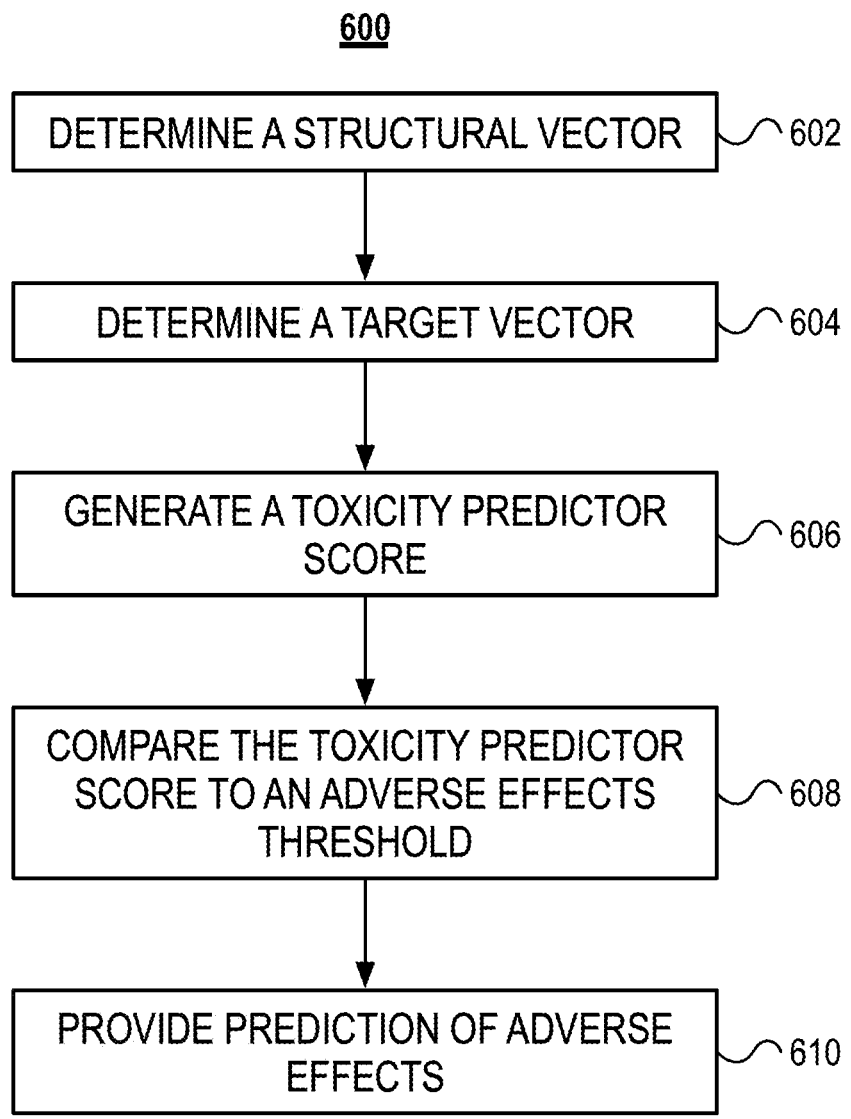
FIG. 6 illustrates a block diagram of an example method to improve the accuracy of a drug toxicity predictor.

FIG. 6 illustrates a block diagram of an example method 600 to improve the accuracy of drug toxicity predictions. The method 600 can include determining a structural vector (BLOCK 602). The method 600 can include determining a target vector (BLOCK 604). The method 600 can include generating a toxicity predictor score (BLOCK 606). The method 600 can include comparing the toxicity predictor score to an adverse effects threshold (BLOCK 608). The method 600 can include providing a prediction of adverse effects (BLOCK 610).

As set forth above, the method 600 can include determining a structural vector (BLOCK 602). The structural vector can be based on the chemical structure of an input chemical. The structural vector can include a plurality of values. Each of the values can correspond to features that are derived by the drug toxicity predictor's structural feature generator based on the chemical structure of the input chemical.

The structural vector can include values from different categories of structural features. For example, the structural vector can include at least one chemical property feature and at least one drug-likeness feature. The chemical property features can include a polar surface area, a molecular weight, a hydrogen bond donor count, a hydrogen bond acceptor count, a charge number, or a number of rotatable bonds. The drug-likeness features can include a quantitative estimate of drug-likeness (QED), a rule of five measure, a Veber rule measure, or a Ghose rule measure.

The method 600 can include determining a target vector (BLOCK 604). The drug toxicity predictor's target feature generator can calculate the target vector based on at least one gene target feature of the input chemical. The target vector can include values that are based on features derived from an interaction between the input chemical and at least one gene target.

The target vector can include values from different categories of gene target features. For example, the target vector can include at least one tissue expression feature and at least one target feature. The tissue expression feature can indicate a level of gene expression in a gene target tissue based on an exposure to the input chemical. The gene target tissue can be at least one of liver tissue, heart tissue, kidney tissue, or brain tissue. The target feature can include at least one of a network connectivity feature, a network betweeness feature, a network degree feature, or a loss of function mutation frequency feature.

The method 600 can include generating a toxicity predictor score (BLOCK 606). The drug toxicity predictor's classifier can determine or otherwise calculate the toxicity predictor score. The classifier can be a machine learning classifier. The classifier can receive or retrieve the structural vector and the target vector. The classifier can use the structural vector and the target vector to determine the toxicity predictor score.

As described above, the classifier can be a random forest classifier. The classifier can include a plurality of decision trees. Each of the decision trees generate a score indicating whether the input will cause adverse events above or below an adverse events threshold. In some implementations, the classifier can use a random selection of values from the target vector and the structural vector as inputs to each of the different decision trees.

In some implementations, the score generated by each of the decision trees can be a binary score indicating whether the input chemical is likely to cause adverse events above or below the adverse events threshold. The classifier can combine the scores from each of the decision trees to generate the toxicity predictor score. In some implementations, the classifier can determine whether there are more scores from the decision trees above the adverse events threshold or more scores below the adverse events threshold.

The method 600 can include comparing the toxicity predictor score to the adverse effects threshold (BLOCK 608). The adverse effects threshold can indicate a relative toxicity of the input chemical. A score above the adverse effects threshold can indicate that the input chemical can have a toxicity that can cause adverse effects. A score below the adverse effects threshold can indicate that the input chemical can have a toxicity that is not likely to cause adverse effects. In some implementations, the adverse effects threshold can be relative to the severity of the disease that the input chemical is provided to treat. For example, for more severe diseases, higher levels of toxicity and greater (or more severe) side effects can be deemed acceptable to the patient.

The method 600 can include providing a prediction of adverse effects (BLOCK 610). The prediction can be responsive to the comparison of the toxicity predictor score to the adverse effects threshold. The prediction can indicate whether the input chemical will demonstrate adverse effects below the adverse effects threshold. For example, if the toxicity predictor score is below the adverse effects threshold, the drug toxicity predictor can provide an output prediction that the input chemical is likely to have a low toxicity that is likely to not cause severe side effects. In some implementations, the prediction can be a prediction of whether the input chemical is likely to pass the toxicity requirements of a clinical trial.

EXAMPLES

As discussed above, the structural vector and the target vector can each include a plurality of values that are derived from features that are based on the chemical's structure or gene target, respectively. Some of the features can be correlated. In some implementations, the classifier can select features to generate the target vector and structural vector that are uncorrelated (or less correlated) with one another.

Figure 7:
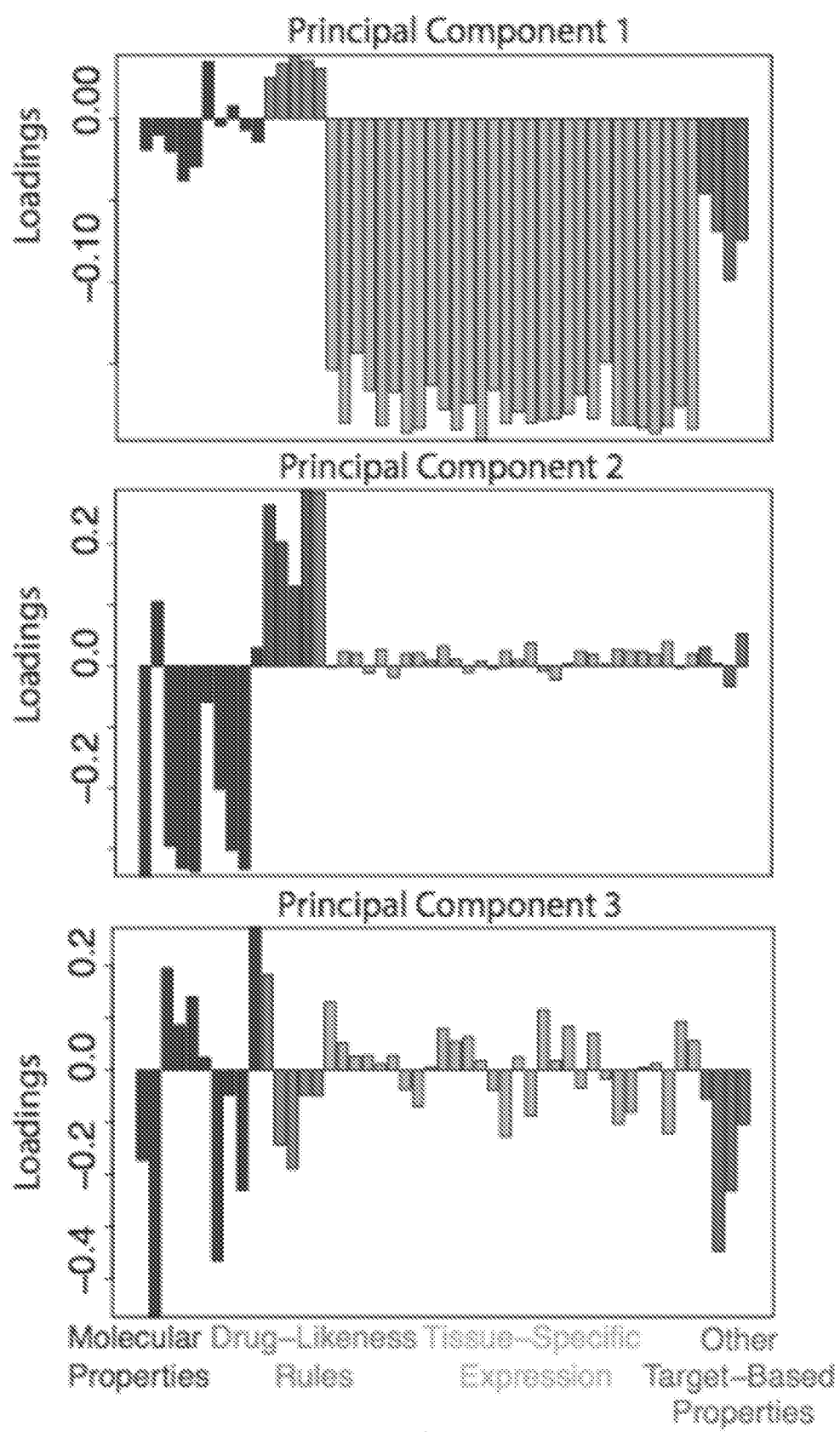
FIG. 7 illustrates plots of the feature correlations between the different categories of features.

The drug toxicity predictor 120 can perform feature correlations using principal component analysis to determine correlation between features. FIG. 7 illustrates plots of the feature correlations between the different categories of features: molecular (or chemical) properties, drug-likeness features, tissue expression features, and other target-based features. The plots illustrate that the expression features are highly correlated. In some implementations, when the values are highly correlated, principle component analysis can be applied to the values to reduce the feature dimensionality. In place of the raw values, the first three principle components can be used.

Figure 8:
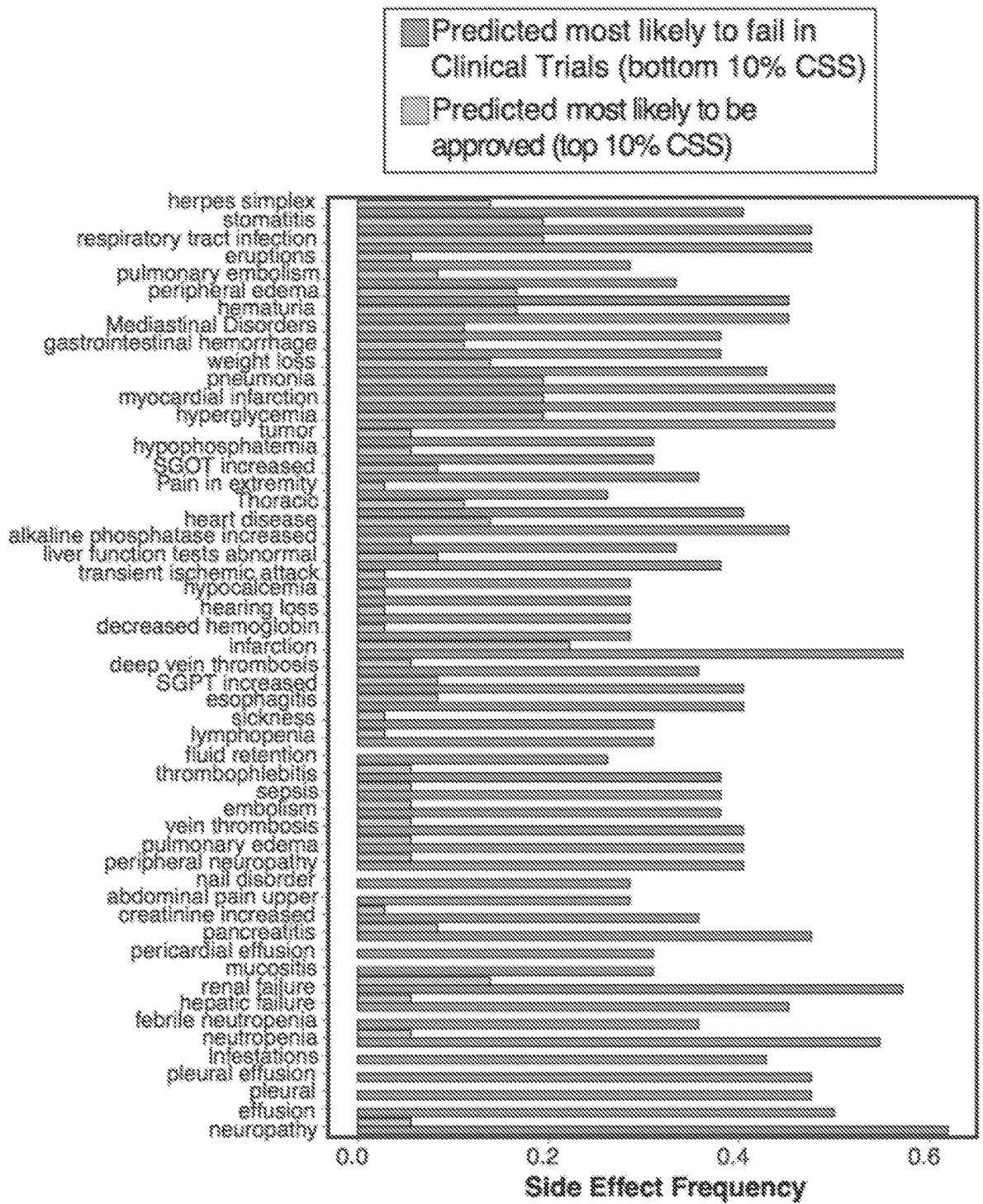
FIG. 8 illustrates a plot of side effect frequency for a test dataset that included input drugs predicted to pass and fail in clinical trials.

FIG. 8 illustrates a plot of side effect frequency for a test dataset that included input drugs predicted to fail in clinical trials (e.g., having a toxicity predictor score above the adverse effect threshold) and input drugs predicted to pass clinical trials (e.g., having a toxicity predictor score below the adverse effect threshold). The plot in FIG. 8 illustrates that side effects happen far more often in the input drugs predicted to fail clinical trials.

Figure 9:
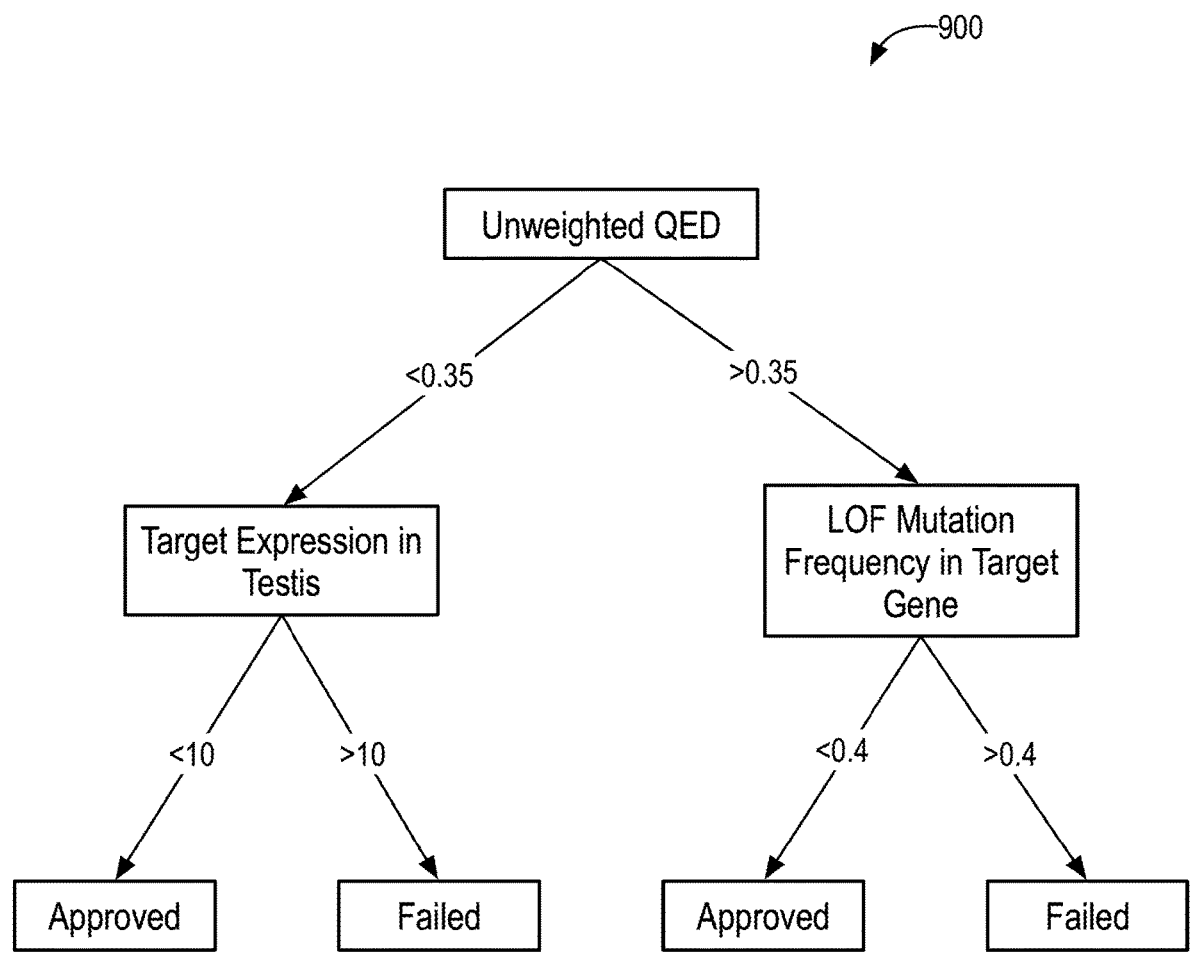
FIG. 9 illustrates an example, simplified decision tree for use by the classifier.
Figure 10:
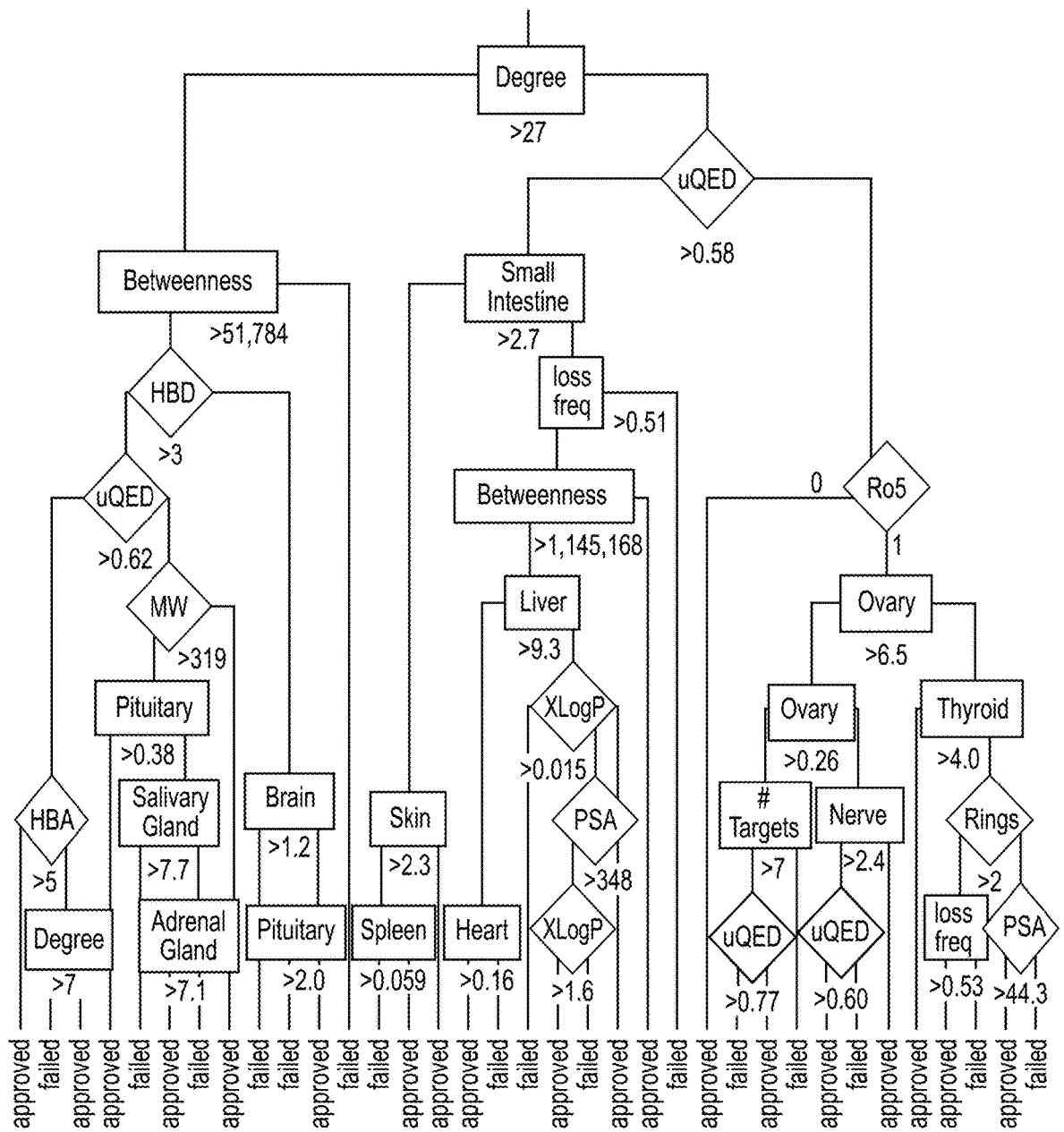
FIG. 10 illustrates an example consensus decision tree that can be used by the classifier.

FIG. 9 illustrates an example, simplified decision tree 900 for use by the classifier. The decision tree 900 takes an unweighted QED value as an input. The first decision is whether the unweighted QED value is above or below 0.35. If the unweighted QED value is below 0.35, the target expression values are analyzed to determine whether the input chemical should be given a passing or failing score. If, originally, the unweighted QED value is above 0.35, the LOF mutation frequency of the target gene are used to determine if input chemical is given a passing or failing score. FIG. 10 illustrates an example consensus decision tree that can be used by the classifier.

C. Systems and Methods to Predict Tissue Specific Drug Reactions

In addition to generating predictions as to the general toxicity of input chemicals, the system described above can also generate toxicity predictor scores for specific tissues and generate side effect predictions. The system can provide a data-driven machine learning approach that integrates information on a chemical's structure, targets, and phenotypic effects with tissue-wide genomic profiling to predict the probability of a chemical presenting with different types of tissue-specific adverse events. Additionally, the system's prediction scores can flag chemicals that were approved, but may be later withdrawn due to unknown adverse events. The system can also identify toxic targets for each tissue type.

Figure 11:
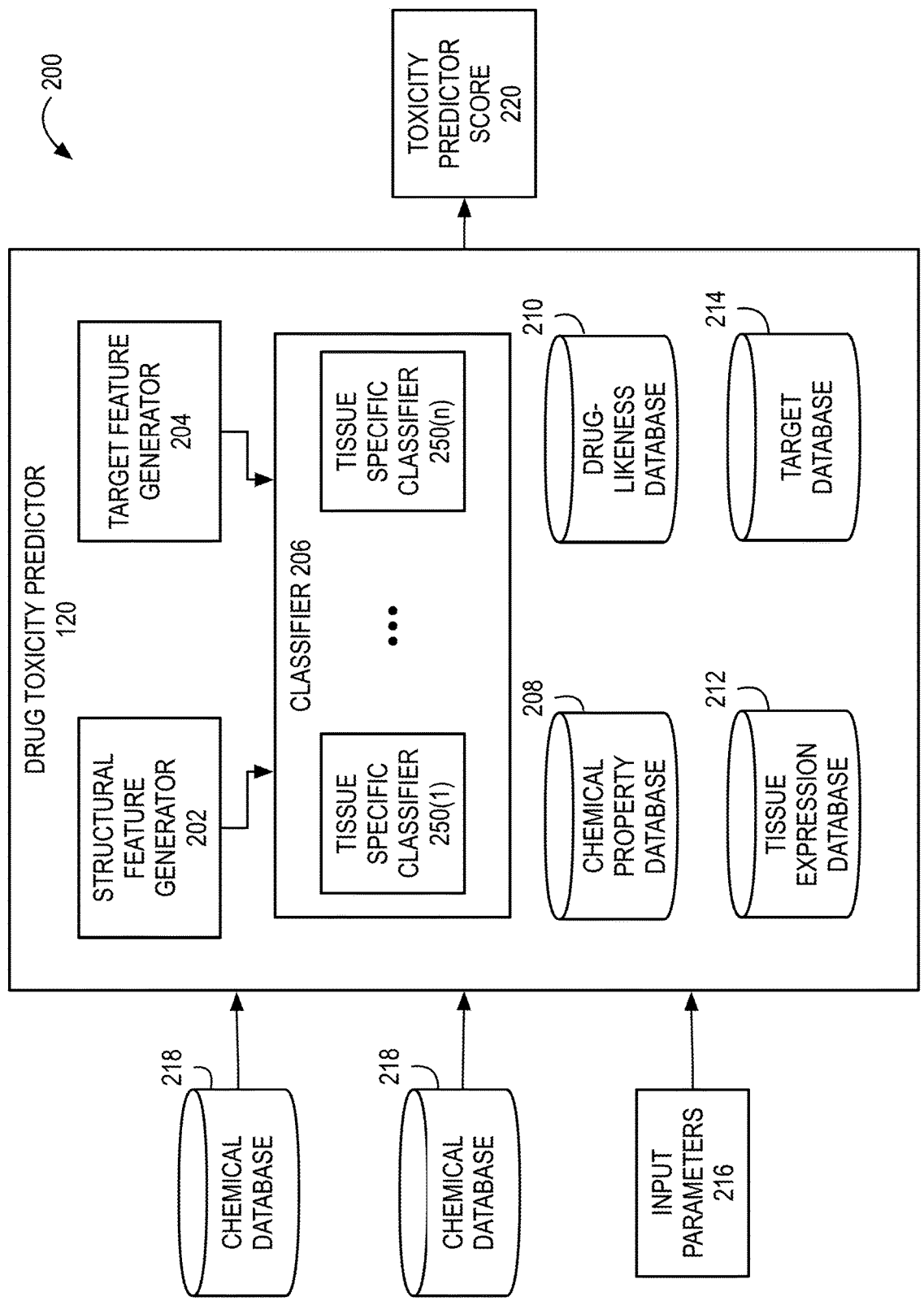
FIG. 11 illustrates a drug toxicity predictor similar to the drug toxicity predictor.

FIG. 11 illustrates a drug toxicity predictor 120 similar to the drug toxicity predictor 120 described above. The drug toxicity predictor 120 illustrated in FIG. 11 can include a classifier 206 that includes a plurality of tissue specific classifiers 250(1)-250(n). For example, the classifier 206 can include a tissue specific classifier 250 for liver tissue, kidney tissue, blood, heart tissue, lung tissue, and pancreas tissue. The tissue specific classifiers 250 can generate toxicity prediction scores 220 that indicate the likelihood that a specific drug is toxic to individual tissues. As discussed above, the structural feature generator 202 and the target feature generator 204 can generate a structural vector and a target vector that is supplied to classifier 206 (and each of the tissue specific classifiers 250). In some implementations, the structural feature generator 202 and the target feature generator 204 can generate a different structural vector and target vector for each of the different tissue specific classifiers 250.

The classifier 206, and each of the tissue specific classifiers 250, can be trained using reference chemicals that cause known toxicity to specific tissues. For example, the chemical database 218 can be the SIDER database that contains information on marketed medicines and their recorded adverse drug reactions. In one example, the drug toxicity predictor 120 can identify each drug in the SIDER database that is associated with liver toxicity. As described above structural vectors and target vectors can be generated for each of the reference chemicals. The structural feature generator 202 and the target feature generator 204 can also generate structural vectors and target vectors for a second set of reference chemicals that do not cause tissue specific toxicities. In some implementations, for each reference chemical, the structural feature generator 202 and the target feature generator 204 can generate a target vector and a structural vector for each of the different tissue specific classifiers 250.

In some implementations, the target feature generator 204 and the structural feature generator 202 can generate target vectors and structural vectors for 30 or more tissue types. For each gene target, the target feature generator 204 can calculate a number of features, such as those described above, such as tissue-specific expression, network properties (betweenness and degree), loss of function (LoF) mutation frequency, and essentiality status. The drug toxicity predictor 120 can use the Consensus PathDB framework to measure for GO term enrichment and observed that for toxic gene sets the most commonly enriched terms had to do with cell death, receptor signaling, and apoptotic processes.

In some implementations, additional features that the classifier 206 can use to determine the toxicity predictor score 220 are discussed in Section D, below, such as known drug indications, known drug interactions, drug dosing information, mass spectrometry images, fluorescence/microscopy images, electronic health record data, gene expression and efficacy data in cells following genetic perturbation, and drug binding efficiencies.

For the reference chemicals, the tissue specific classifiers 250 can determine how similarities between the reference chemicals identified as safe and reference identified as toxic. FIGS. 12A-12D illustrate a plot comparing all toxic drugs pairs, safe drug pairs, and all combinations of toxic and safe drugs for drug structures similarities (FIG. 12A), similarities in gene expression changes (FIG. 12B), similarities in growth efficacies (FIG. 12C), and similarities between bioassays (FIG. 12D). The P values were calculated using a Wilcoxon Rank Sum test.

Figure 12A:
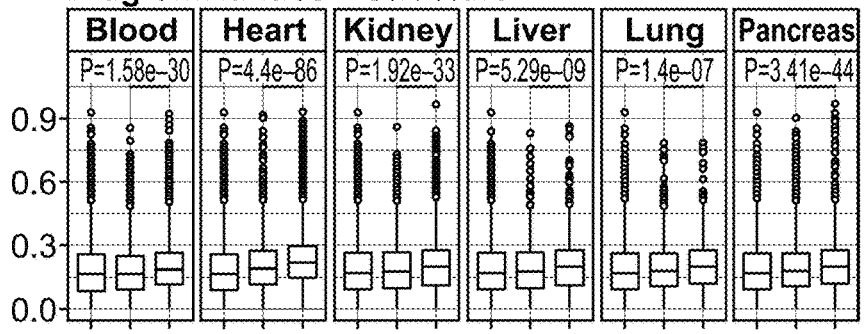
FIGS. 12A-12D illustrates a plot comparing toxic drugs pairs, safe drug pairs, and all combinations of toxic and safe drugs for different types of similarities.
Figure 12B:
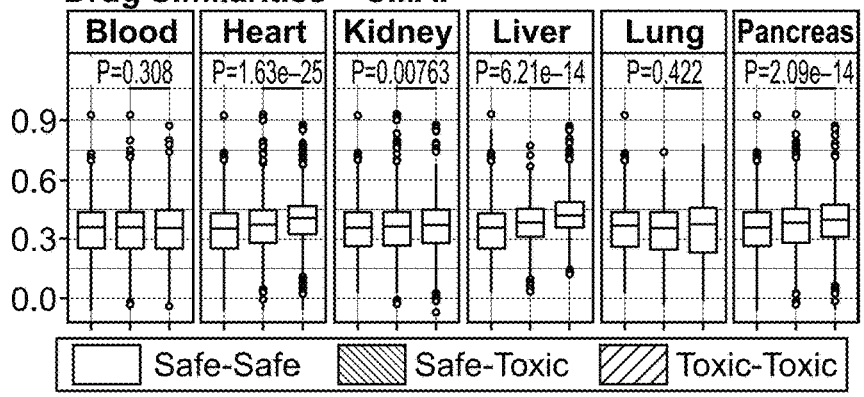
Figure 12C:
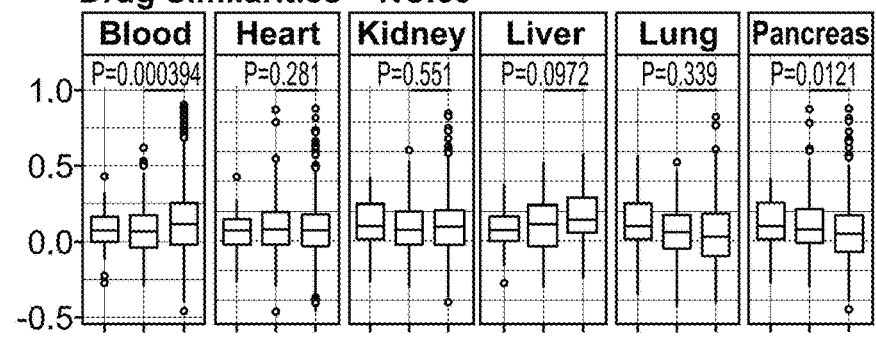
Figure 12D:
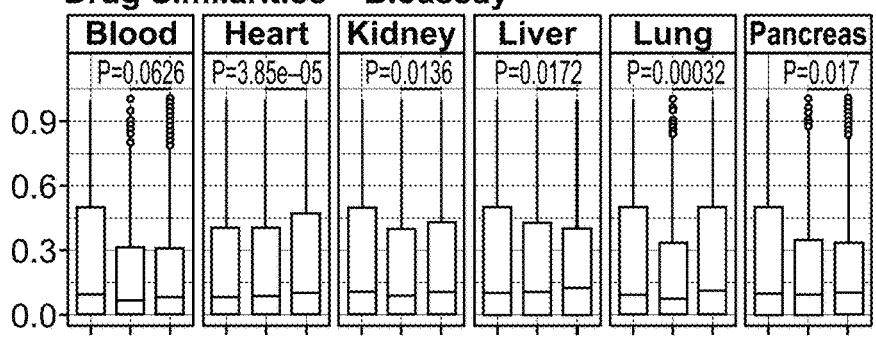

As illustrated in FIGS. 12A-12D, the tissue-specific toxic drugs were most structurally similar to each other (FIG. 12A). Additionally, toxic drugs tended to also be most similar to other toxic drugs in terms of differential gene expression profiles (FIG. 12B), growth inhibition screens (FIG. 12C), and bioassays (FIG. 12D). The tissue specific classifiers 250 also identified patterns across the different tissue types—for instance, growth inhibition was best able to separate out drugs with blood specific adverse events, whereas gene expression changes had the greatest utility in the liver. These patterns can be used for adverse event prediction as they highlight the diversity across drugs with a given side effect. For example, high structural similarity between a new chemical and chemicals known to be toxic in the heart could indicate potential cardiac toxicity for that new chemical. Additionally, high similarity between the chemical-induced expression changes of a new chemical with expression changes of chemicals with known liver toxicity could suggest liver toxicity for the new chemical.

As also discussed above, the tissue specific classifiers 250 can also use target vectors to determine the toxicity prediction scores 220. For example, tissue-specific expression data can be retrieved by the target feature generator 204 from the GTEX database (an example chemical database 218). For each toxic or safe drug in a given tissue set, the target feature generator 204 quantified the expression of all of that drug's targets in each of the specific tissues.

FIGS. 13A-13E illustrate plots of distributions of target expression in a specific tissue for drugs with and without any tissue specific adverse events. As illustrated in FIGS. 13A-13E, drugs with adverse events in a specific tissue tended to have higher target expression in that tissue than their safe drug counterparts. This information can illustrate that considering target based features and tissue-specific expression when predicting adverse events improves the accuracy of toxicity prediction scores 220. The plots also illustrate that high expression of a drug's target in a given tissue can help predict toxicity in that tissue.

Figure 13C:
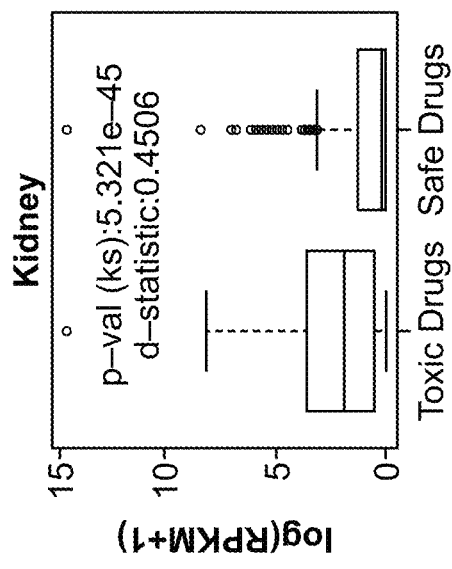
FIGS. 13A-13E illustrate plots of distributions of target expression in a specific tissue for drugs with and without any tissue specific adverse events.
Figure 13B:
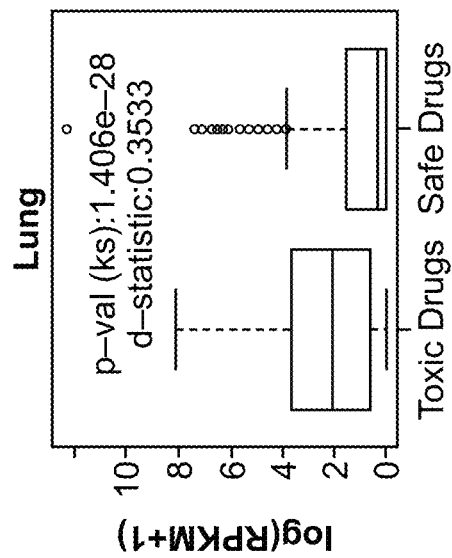
Figure 13A:
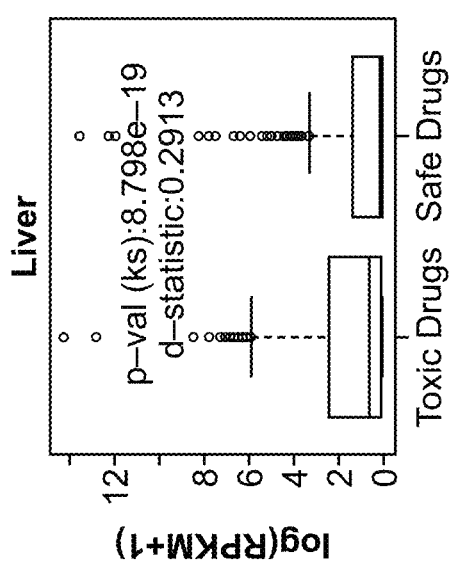
Figure 13E:
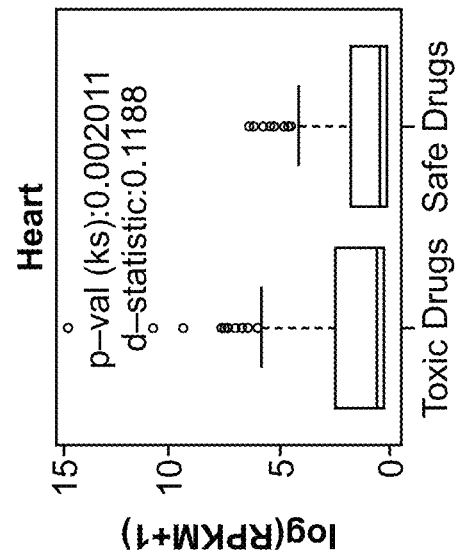
Figure 13D:
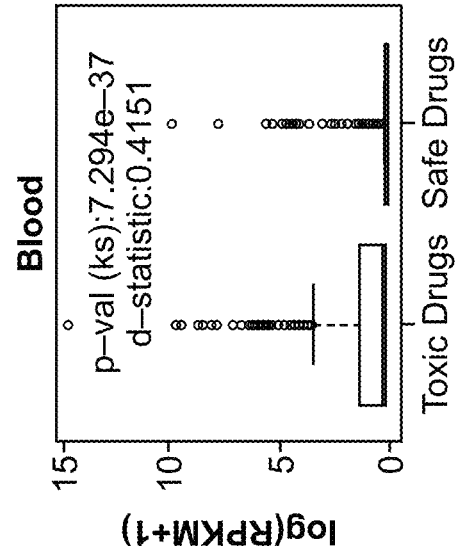
Figure 13H:
FIG. 13F-13H illustrate plots showing a degree of overlap between the toxic and safe gene sets across multiple tissues.
Figure 13G:
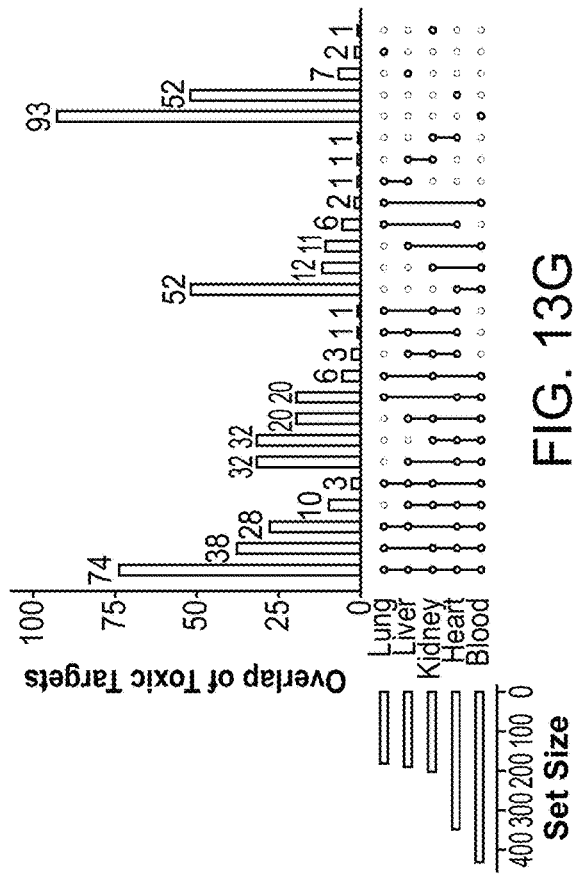
Figure 13F:
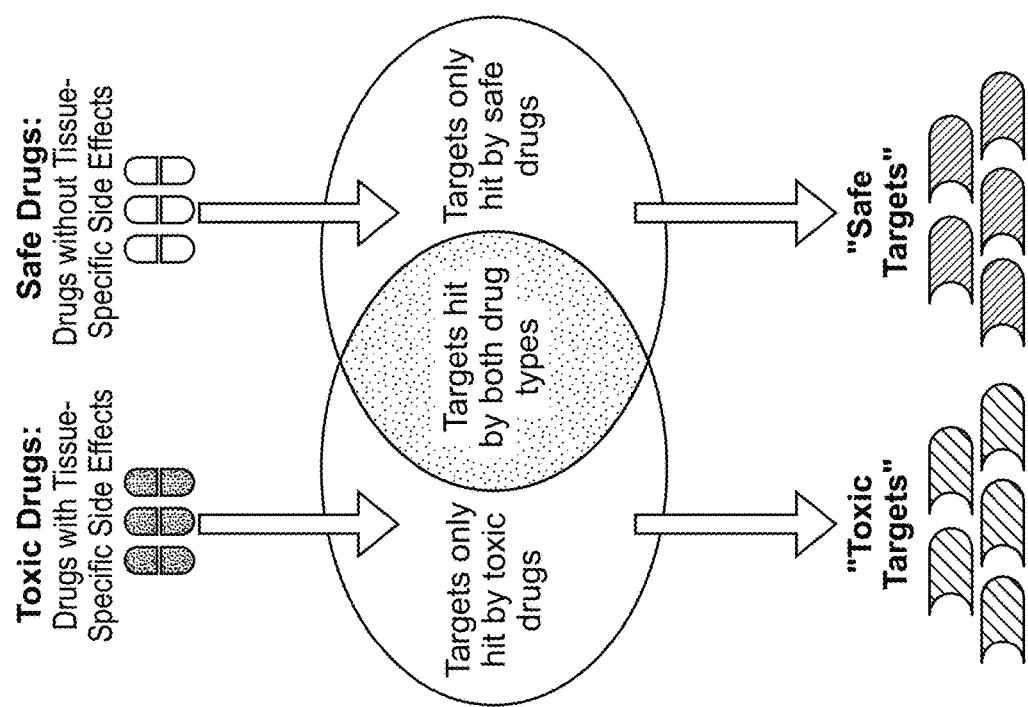

Referring to FIG. 11, the target feature generator 204, for the reference chemicals, can determine a set of tissue-specific "toxic targets" (proteins that are only targeted by drugs with known toxicity in that tissue) and "safe targets" (proteins only targeted by drugs with no related tissue toxicities) by identifying any target's exclusive subset of drugs. FIG. 13F illustrates a schematic of the target feature generator 204 selecting save and toxic targets. As illustrated in FIG. 13F-13H, there can be a degree of overlap between the toxic and safe gene sets across multiple tissues, and there were a number of proteins identified that were specifically associated with toxicity or non-toxicity in a single tissue.

In some implementations, each of the tissue specific classifiers 250 can generate a toxicity prediction score 220 that indicates the likelihood of the input chemical causing a predetermined adverse effect associated with the tissue associated with the specific tissue specific classifiers 250. For example, the tissue specific classifiers 250 can determine a toxicity prediction score 220 that indicates the likelihood of the input chemical causing at least one of drug-induced liver injury (DILI), nephrotoxicity, neutropenia, heart attack, pleural effusion, and pancreatitis.

In some implementations, when generating the structural vector and the target vector to generate tissue specific toxicity prediction scores 220, the structural feature generator 202, for an input chemical, can calculate a structural vector with 13 structural feature values. The target feature generator 204 can calculate a target vector with 35 gene target feature values and 8 drug-likeness feature values. For tissue-based features, the target feature generator 204 can considered the number of known drug targets that fall in the associated tissue-specific safe and toxic gene sets. The target feature generator 204 can also incorporate the above described tissue expression features from GTEx19, network properties (connectivity and degree), and loss of function mutation frequency. The drug likeness scores can include structural similarities, CMAP similarities, NCI60 similarities, and bio assay similarities. The first similarity metric can represent whether the drug is more similar to known safe or toxic molecules by using a signed Kolmogorov-Smirnov D-statistic. The second similarity metric is a count of the number of highly similar drugs with known TSAEs.

In one example, the classifier 206, using tissue specific classifiers 250, was evaluated using 10-fold cross validation. FIG. 14A illustrates the performance metrics of the tissue specific classifiers 250. All adverse events achieved significant predictive performances with an average accuracy of 72% and area-under-the-receiver-operator curve (AUC) of 0.81 (FIG. 14A). FIG. 14B illustrates a ROC for the kidney tissue specific classifier 250. Focusing specifically on neutropenia—a major cause of clinical trial failure and mortality in cancer and immunocompromised patients—the classifier 206 achieved an AUC, accuracy, specificity, and sensitivity of 0.8843, 0.7839, 0.7778, and 0.7891, respectively (FIG. 14B).

EXAMPLES

The systems described above, were tested using an independent validation test set. For liver toxicity, the FDA has curated the Liver Toxicity Knowledge Base (LTKB) that classifies a number of chemicals based on their risk of causing liver toxicity. The system was able to distinguish drugs that were of DILI-concern from those classified as no concern using this independent database (FIG. 14C) (p<2.2e-16, Mann-Whitney U test). For heart attacks, pleural effusion, and neutropenia the system was tested with the FDA drug's labeled with warnings as reported in openFDA. The system was able to correctly identified 76.3% of drugs with heart attack risk (p=0.04589, Binomial test), 75.0% with pleural effusion risk (p=0.01474, Binomial test), and 87.5% with neutropenia risk (p=0.0782, Binomial test) (FIG. 13D).

Figure 15A:
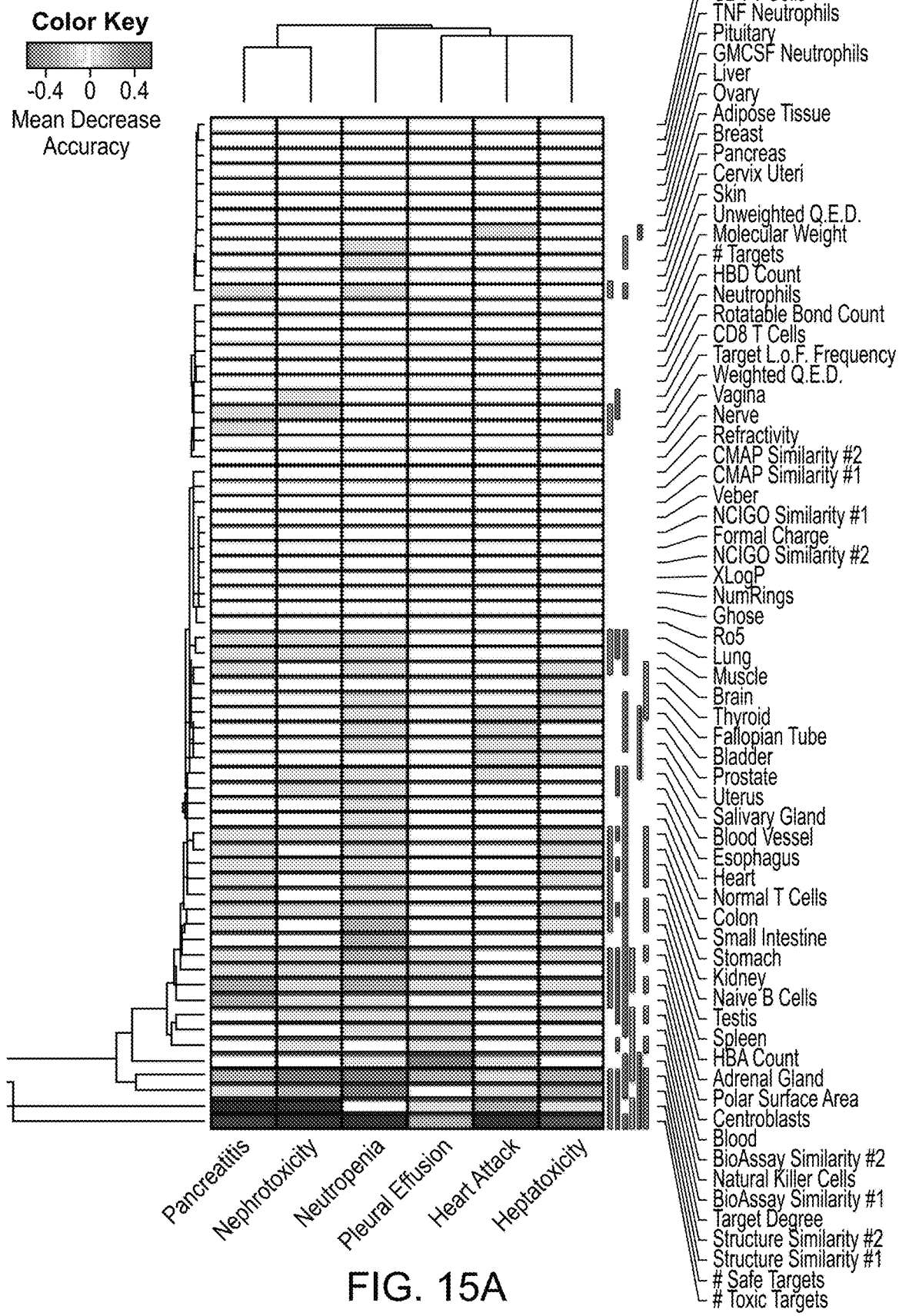
FIGS. 15A-15D illustrate plots of a feature analysis for the system.
Figure 15B:
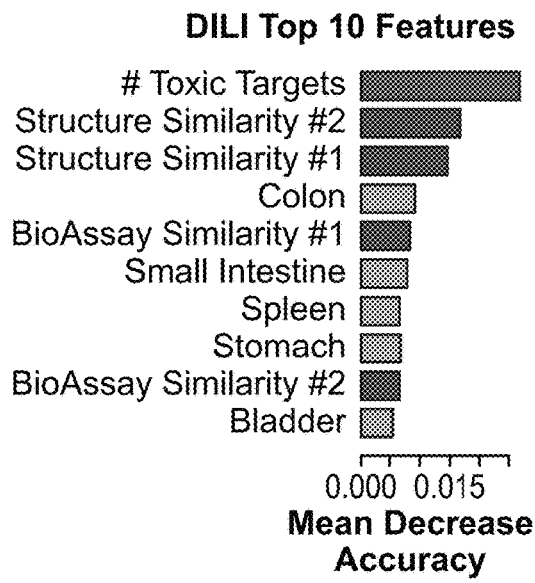
Figure 15C:
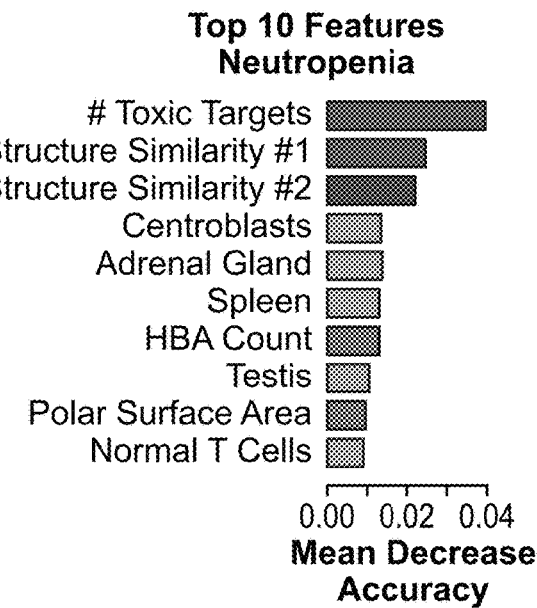
Figure 15D:
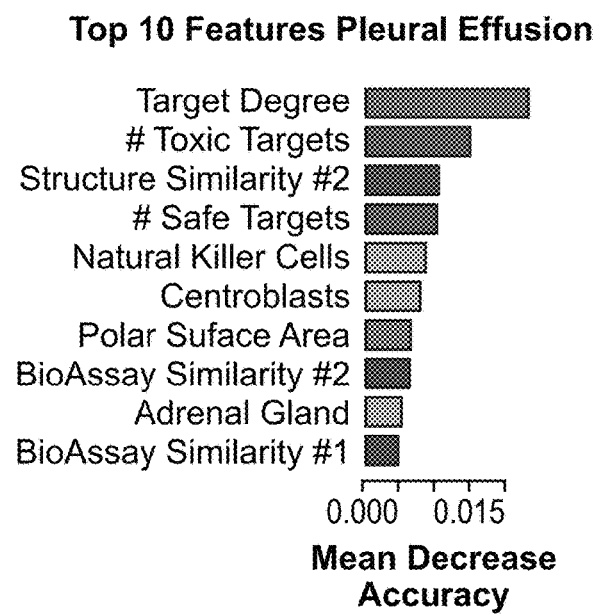

A feature importance analysis revealed that there is a subset of features that were consistently predictive across all of the system's adverse event models. FIG. 15A illustrates a feature importance analysis. The toxic and safe gene sets, structural and bioassay similarity features, polar surface area, and expression of the drug target in mature B cells are important in a majority of models. The analysis also revealed features that were helpful in generating accurate toxicity prediction scores 220. For example, target expression in digestive organs (e.g., colon, small intestine, stomach) were important in the prediction of DILI (FIG. 15B), expression in immune-related cells (centroblasts, T cells, spleen) were important for neutropenia prediction (FIG. 15C), and the network degree of the drug target was the most important feature in prediction of pleural effusion (FIG. 15D).

Figure 16A:
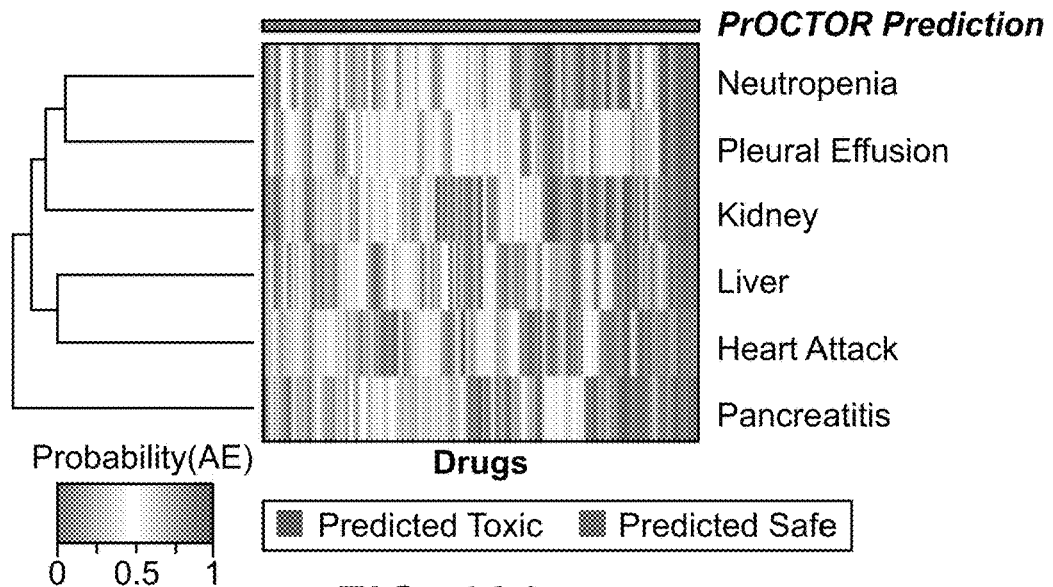
FIGS. 16A-16C illustrate plots of the system for different drug types.
Figure 16B:
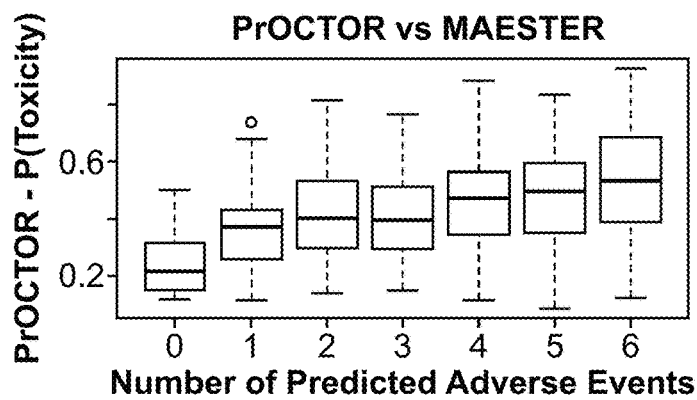
Figure 16C:
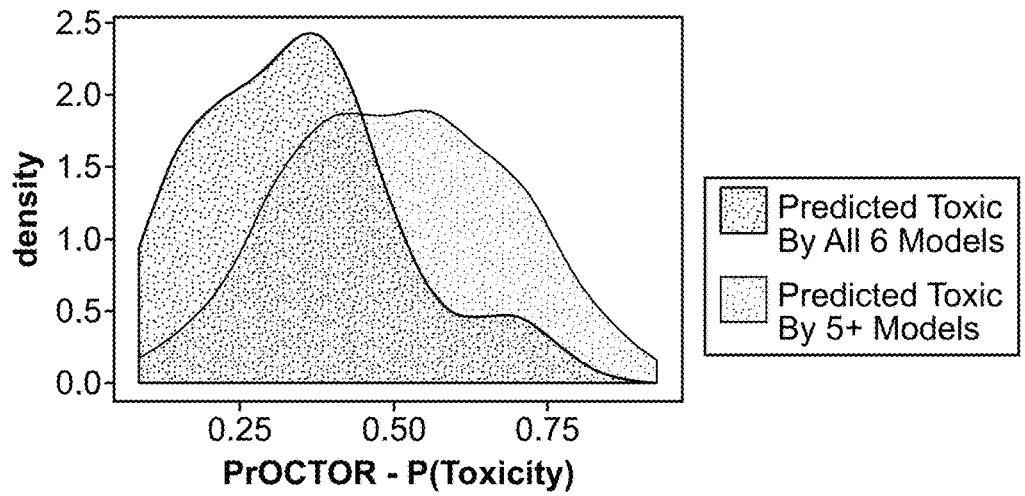

The system was then tested for drugs across all models (FIG. 16A). The results indicated that there were subsets of drugs that are predicted to be safe or toxic by most or all models. The system accurately determined that drugs with more side effects had higher predicted toxicity levels (FIG. 16B) than drugs that were predicted to have one or fewer side effects (FIG. 16C).

Figure 17A:
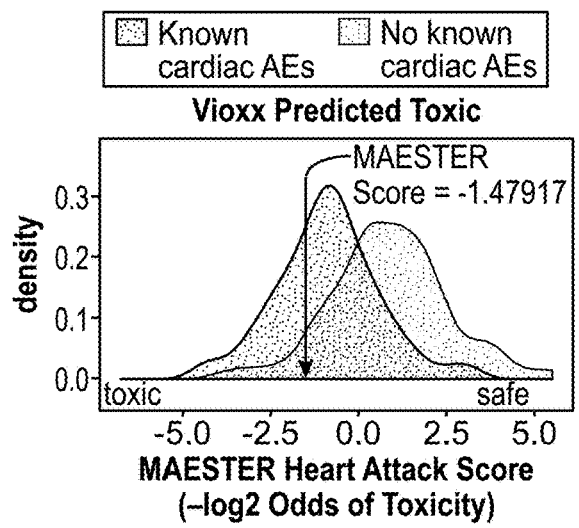
FIGS. 17A-17F illustrate plots of the system to predict specific side effects.
Figure 17B:
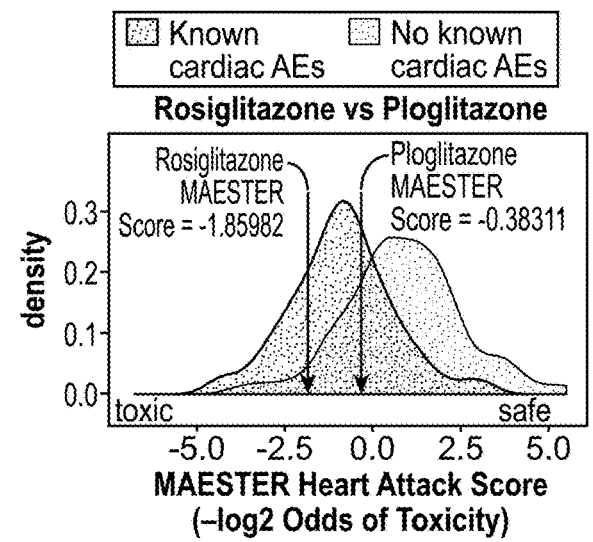
Figure 17C:
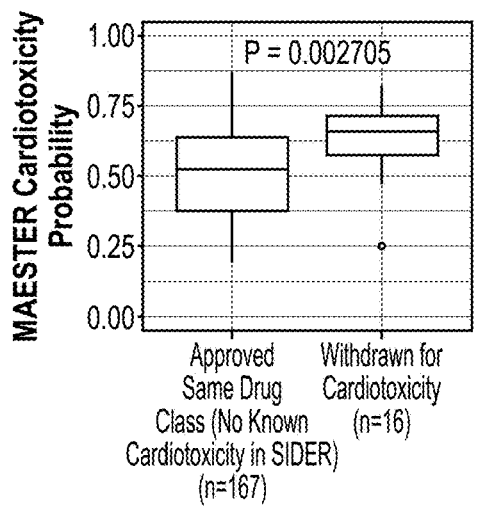
Figure 17D:
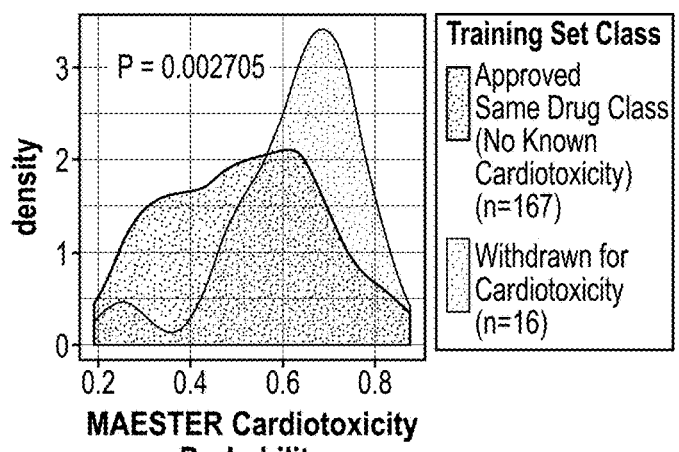
Figure 17E:
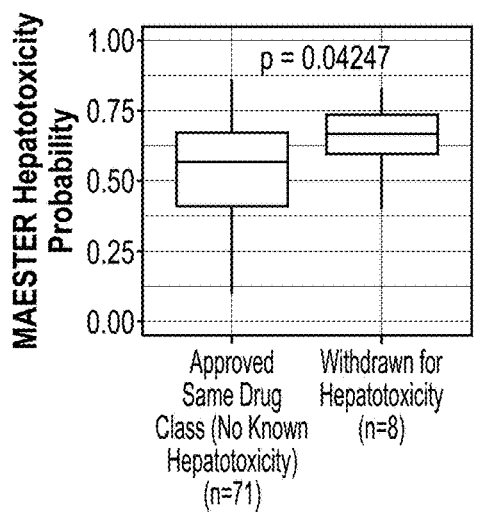
Figure 17F:
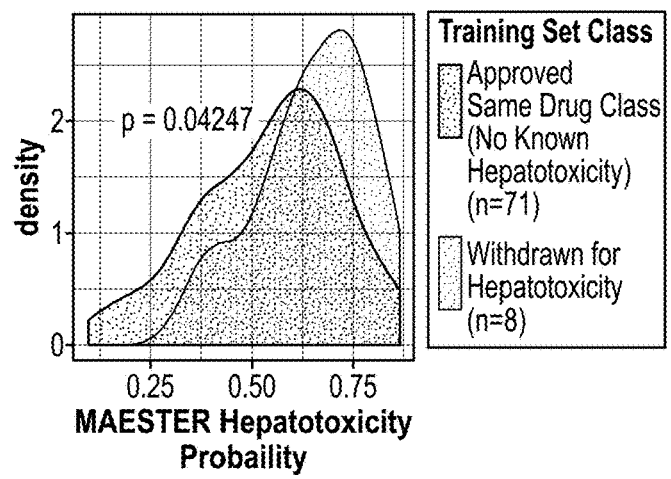

To test the system's ability to detect adverse events that may have been missed by traditional approaches, drugs that were approved but were later withdrawn due to toxicity concerns were analyzed with the system. This is especially relevant because cardiotoxicity and hepatotoxicity are the largest causes of toxicity related withdrawal. Vioxx and Avandia, both withdrawn for cardiac toxicity, were found by the system to each be predicted to be highly likely to cause cardiac toxicity (FIGS. 17A and 17B). Additionally, the system determined the less toxic Avandia (Rosiglitazone) to have a lower toxicity prediction score than the more toxic Pioglitazone.

For 87.5% of the withdrawn drugs, the system predicted that specific adverse event with a probability greater than 0.5. To further evaluate the system's ability to flag withdrawn drugs, the system calculated toxicity prediction scores for withdrawn drugs were compared against probabilities for drugs of similar indications that were never withdrawn and were not known to have the reported adverse event (FIG. 17C-17F). The system determined that the withdrawn drugs had significantly higher toxicity prediction scores 220 than approved drugs of the same indication (p=0.0027 and 0.0424, Fisher's exact test). Overall these results highlight the system's ability to specifically identify chemicals with adverse events that were missed by traditional approaches.

D. Systems and Methods for Computational Analysis to Predict Binding Targets of Chemicals In some implementations, the system can use computational analysis for predicting binding targets of chemicals. In some embodiments, the disclosure relates to systems and methods for computationally analyzing chemical data of one or more chemicals to predict binding targets of the one or more chemicals. In some embodiments, the disclosure relates to systems and methods for identifying one or more chemicals likely to bind with a given binding target.

The present disclosure discusses systems and methods to characterize a small molecule's mechanism. The system and method can integrate multiple, independent pieces of evidence corresponding to a plurality of data types into a cohesive prediction framework to improve target predictions. The system can integrate over 20,000,000 data points from a plurality of distinct data types, such as, but not limited to, drug efficacies, post-treatment transcriptional responses, drug structures, reported adverse effects, bioassay results, chemogenomic fitness signatures, and known targets, to predict drug-target interactions.

The method can include, for each data type, calculating a similarity score for each of the chemical pairs with known targets. In some implementations, there can be little overall correlation across different similarity scores. These results can suggest that each data type is measuring a different aspect of a chemical's activity and that individual features for a given chemical may not be extrapolated based on other data types.

The method can also include separating chemical pairs into two groups: (1) those that shared at least one known target and (2) those pairs with no known shared targets. The system can apply a Kolmogorov-Smirnov test to each similarity score and used the associated D statistic to calculate the degree to a given data type could separate out chemical pairs that shared targets. Any of the data types can be used, but in some implementations, the system uses structural similarity to separate the chemical pairs into two groups. In some implementations, a similarity across an unbiased set of bioassays and the relatively simple NCI-60 growth inhibition screen can be used by the system to differentiate shared target chemical pairs. In other implementations, a transcriptional responses and reported adverse effects can be used to differentiate shared target chemical pairs.

The method can also include, for every chemical pair, converting each individual similarity score into a distinct likelihood ratio. These individual likelihood ratios can then be combined within a Naïve Bayes framework to obtain a total likelihood ratio (TLR), which can be proportional to the odds of two chemicals sharing a target given all available evidence. The system can calculate TLRs for each possible chemical pairs with known targets and the system can evaluate the output using a 5-fold cross validation. In some implementations, an Area Under the Receiver Operating Curve (AUROC) can be used to identify chemicals that share targets. In some implementations, the system's calculated ratio of true to false positives increased as the cutoff value is raised, which can indicate that the system's TLR output is a dynamic value that estimates the strength and confidence level of a specific prediction and can specifically examine chemical-target predictions of the highest quality.

In some implementations, the system can replicate the results of experimental screens and predict other specific target interactions. In some implementations, the system can be used to potential kinases targets for orphan molecule. The implementation of this method is discussed further below.

In some implementations, the computational chemical analysis system can predict specific targets. In some implementations, the system can select proteins that appeared as a known target in a large number of shared target predictions for testing as a specific target for the tested orphan molecule. The system can use a "voting" method to predict specific targets for each orphan small molecule by identifying any recurring targets. In some implementations, the system used the voting method to a test set of chemicals and demonstrated that as the cutoff of what was considered a shared-target prediction was increased, the accuracy level—measured by the system could identify a known chemical target—steadily increased. The accuracy level reached approximately 90% at a cutoff of 500, demonstrating that the system can accurately identify specific targets for a set of small molecules.

In some implementations, the system can also be used to predict novel targets for small molecules with no known targets or mechanisms of action in the system's database. For example, the system analyzed about 14,168 orphan molecules with sufficient data and confidently predicted targets for 4,167 unique small molecules (30% of the original set), with predictions spanning over 560 distinct protein targets. By filtering based on a higher TLR cutoff and higher target-recurrences, the system narrowed this list to 720 high confidence orphan-target predictions. To date, this is the largest database of novel chemical-target predictions and this list can be exploited further to discover potential novel therapeutics and small molecules for a target of interest. In some implementations, the system can operate under two operating scenarios: 1) Using the system in combination with a library of chemicals, for instance, orphan small molecules to identify new ways to target a specific binding target, for instance, a protein and 2) to integrate the system directly into the drug development pipeline to predict targets and guide experiments for drugs currently in development.

In some implementations, the computational chemical analysis system can discover novel microtubule-targeting compounds capable of overcoming drug resistance. For example, beginning with the first operating scenario, the computational chemical analysis system can identify novel ways to target microtubules. Anti-microtubule drugs make up one of the largest and most widely used classes of chemotherapeutics, and tubulin is one of the most validated anticancer targets to date. However, patient response following treatment is variable, and adverse effects along with the development of drug resistance limits clinical applicability of current drugs. Hence, the discovery of additional anti-microtubule drugs could significantly improve cancer therapy by identifying compounds that could act on refractory tumors or have more tolerable side-effect profiles. The computational chemical analysis system can created a network of known and predicted anti-microtubule small molecules with edges representing a predicted shared target interaction. In some implementations, the known microtubule-targeting chemicals can tend to cluster together based on their mechanisms of action. For instance, Paclitaxel can cluster with Carbazitaxel and Docetaxel—all known microtubule-stabilizing drugs—while Colchicine can cluster with other known microtubule-destabilizing drugs such as Podophyllotoxin. In some implementations, the computational chemical analysis system is configured to understand and differentiate drug mechanisms as well as specific targets.

In one example, the human breast cancer MDA-MB-231 cells were chosen for validation experiments as microtubule-inhibitors (both stabilizing and destabilizing) are commonly used in the treatment of breast cancer patients. Cells were treated for 6 hours with 1 and 10 µM of each small molecule, and the effect on cellular microtubules was assessed by confocal microscopy following immunofluorescence with an anti-a-tubulin antibody, to visualize the integrity of the microtubule cytoskeleton. The results showed that 16 of the orphan small molecules exhibited significant effects on microtubules, a much higher success rate than one would expect by chance. A second biochemical assay quantifying the extent of tubulin polymerization or depolymerization that each small molecule exerted on the target corroborated the imaging results. The system determined that several small molecules had increased activity at the lowest dose (1M) while others exhibited a dose-dependent effect on microtubule depolymerization, further establishing microtubules as their bona-fide target. Taken together, these experiments confirmed the predicted targets and mechanism of action for the majority of the small molecules. These results demonstrate the system's target prediction accuracy and how the system can be used on compound libraries to identify small molecules acting on specific targets to further investigate.

One of the problems with current anti-microtubule therapies is a variable patient response and acquired drug resistance after prolonged treatment. In some implementations, the computational chemical analysis system can accurately identify a set of structurally diverse small molecules that all bind a common target (in this case microtubules). In some implementations, the newly identified microtubule-depolymerizing small molecules could successfully kill tumors resistant to other known anti-microtubule drugs. Using the 1A9 human ovarian carcinoma cell line—which have previously been used successfully in selecting microtubule treatment resistant clones—clones resistant to Eribulin mesylate were created, a microtubule depolymerizing agent that is known to promote apoptosis by binding microtubules and inhibiting their function. Recent clinical trials have shown that fewer than 50% of breast cancer patients showed any detectable response after treatment with Eribulin, further highlighting the importance of finding other methods to target these refractory tumors. The top 4 performing small molecules were tested on these 1A9 resistant lines and it was found that 3 out of 4 successfully depolymerized microtubule dimers in resistant cells with images revealing "fuzzy" microtubule bundles with lines no longer spanning individual cells. While deeper investigation into these compounds may help to fully understand their resistance breaking mechanisms, these results further demonstrate the computational chemical analysis system's utility. Even though the computational chemical analysis system is "trained" using a database of chemicals with known targets and mechanisms, the computational chemical analysis system can accurately identify chemicals with distinct mechanisms of action from chemicals in the training set. This can enable the system to be used to identify small molecules with truly novel mechanisms and specifically identify a subset of chemicals, for instance, small molecules from compound libraries with the potential to overcome drug resistance.

In some implementations, the computational chemical analysis system can uncover selective antagonism of DRD2 by anti-cancer small molecule ONC201. In another example, operating under the second operating scenario, the computational chemical analysis system can be configured to be integrated into the drug development pipeline to predict targets for a specific chemical, such as a small molecule. The computational chemical analysis system was used to analyze ONC201, a clinical-stage small molecule in oncology. ONC201 is a small molecule discovered in a phenotypic screen for p53-independent inducers of the pro-apoptotic TRAIL pathway and is currently in phase II clinical trials for select advanced cancers. Although the contribution of ONC201-induced ATF4/CHOP upregulation and inactivation of Akt/ERK signaling to its anti-cancer activity has been characterized, its molecular binding target has remained elusive.

To predict direct binding targets for ONC201, the computational chemical analysis system is configured to calculate the likelihood ratios between ONC201 and all chemicals with known targets in the computational chemical analysis system's database. The computational chemical analysis system's top shared target prediction was between ONC201 and Oxiperomide, a small molecules inhibitor of dopamine receptors that has previously been used in the treatment of dyskinesias. The computational chemical analysis system's voting analysis also indicated that the most likely targets of ONC201 are dopamine receptors—specifically DRD2—and adrenergic receptor alpha, both of which are members of the G-protein coupled receptor (GPCR) superfamily.

To test the target prediction, in vitro profiling of GPCR activity using a heterologous reporter assay for arrestin recruitment, a hallmark of GPCR activation was performed. Profiling results indicated that ONC201 selectively antagonizes the D2-like (DRD2/3/4), but not D1-like (DRD1/5), subfamily of dopamine receptors, with no observed antagonism of other GPCRs under the evaluated conditions. Among the DRD2 family, ONC201 antagonized both short and long isoforms of DRD2 and DRD3, with weaker potency for DRD4. Further characterization of ONC201-mediated antagonism of arrestin recruitment to DRD2L was assessed by a Gaddam/Schild EC50 shift analysis, which determined a dissociation constant of 2.9 uM for ONC201 that is equivalent to its effective dose in many human cancer cells. Confirmatory results were obtained for cAMP modulation in response to ONC201, which is another measure of DRD2L activation. The ability of dopamine to completely reverse the dose-dependent antagonism of up to 100 uM ONC201 suggests direct, competitive antagonism of DRD2L. In agreement with the specificity of ONC201 predicted by the system, no significant interactions were identified between ONC201 and nuclear hormone receptors, the kinome, or other drug targets of FDA-approved cancer therapies. Interestingly, a biologically inactive constitutional isomer of ONC201) did not inhibit DRD2L, suggesting that antagonism of this receptor could be linked to its biological activity. In summary, these studies further demonstrate the system's ability to act as a tool to advance drug development and establish that ONC201 selectively antagonizes the D2-like subfamily of dopamine receptors. Although, further study is required to evaluate the contribution of these molecular interactions to the efficacy and side effect profiles of ONC201, this target information is incredibly valuable to the future development of ONC201, and in fact led to the creation of a new clinical trial in pheochromocytomas—a type of cancer with particularly high expression of DRD2.

In some implementations, the computational chemical analysis system can determine drug mechanisms and can help understand the drug "universe." Following validation that the computational chemical analysis system could accurately determine the specific targets for small molecules, it was then examined how the computational chemical analysis system could also be used to understand a given drug's mechanisms of action (MoA). The computational chemical analysis system was configured to test all pairs of known microtubule-targeting drugs, and created a hierarchical cluster of drugs based on their TLR outputs. The computational chemical analysis system observed a clean separation between drugs known to destabilize microtubule polymers—depolymerizing agents—and those known to stabilize microtubule polymers—polymerizing drugs. A similar MoA-based division was observed when all known protein kinase inhibitors were clustered. Overall these results demonstrate that the system can be used to differentiate small molecules based on their MoAs without additional model training. Combined with the earlier voting method, this demonstrates an efficient pipeline for small molecule target and mechanism identification: by first using the computational chemical analysis system to predict targets and then clustering the chemical, for instance, orphan molecule with other chemicals known to act on the same target, the computational chemical analysis system can identify both the target and MoA for each chemical, for instance, orphan small molecule.

Expanding beyond chemicals known to target the same molecule, the computational chemical analysis system can be configured to provide an overview of how different types of drugs are related to one another. Based on the total likelihood ratio or value between each chemical pair, the computational chemical analysis system can construct a network representative of the drug "universe," or known drugs with at least one predicted shared target interaction. The computational chemical analysis system can classify each drug according to its 1st order ATC code—characteristic of the type and intended use of each drug. In addition to drugs of a similar ATC code clustering together, the system can detect many clusters indicative of drug mechanisms or effect. As expected, microtubule targeting agents clustered with other known chemotherapy drugs, particularly the analogues of camptothecin, for which a dual role as topoisomerase I and tubulin polymerization inhibitors has been previously reported. Conversely, the system unexpectedly found opioids closely interconnected with microtubule targeting agents; this unanticipated observation is in line with previous reports showing how exposure to microtubule targeting drugs can increase the levels of the opioid receptor in rat cerebellums and that treatment of cardiac myocytes with opioids induces microtubule alterations. This unexploited finding could potentially represent an example of drug repurposing, suggesting novel clinical indications of drugs already FDA-approved. As further proof of the robust clinical value of the broad universe clustering approach, further analysis also detected the close clustering of known beta-blockers with many anti-Parkinson's medications, which was especially interesting given that one of the most controversial clinical applications of beta-blockers is to reduce tremors in Parkinson's patients. Drug clustering was also strongly indicative of potential side effects, as suggested by the link between antiretroviral medications, which often cause metabolic side effects like hypercholesterolemia, and statins, FDA-approved cholesterol lowering drugs. Overall, this broad universe clustering approach could greatly advance future drug development and drug repositioning efforts. For example, the computational chemical analysis system's clustering can be used to observe how broad drug classes interact with one another, and also to find interesting connections between specific drug types that could be used for drug repositioning.

To get a better understanding of how orphan small molecules fit into this drug "universe" the system is configured to compute the distance between every pair of small molecules and used multi-dimensional scaling to visualize the overall structure. The system detected a definite structure with known drugs tightly clustering around each other, while orphan molecules had a more diffuse organization. One explanation for this structure is that drugs with known targets are more likely to be used to treat patients and thus may have similar effects due to safety precautions, whereas orphan molecules which have not gone through clinical trials and FDA approval are more likely to have a wide variety of effects and characteristics.

One of the strengths of the Bayesian framework that the system uses is that it can easily accommodate new features as they become available, and, as observed, there is an expectation that the addition of new data will improve the overall performance. In addition, as more information becomes available there are many aspects of the current implementation that can be improved. For instance, as more data become public the system can better understand the dependencies between distinct data types and model those within the Bayesian network. Furthermore, at this time, there was very little information available on binding kinetics, but as this changes the system's algorithm could be adapted to incorporate the binding degree and better predict on vs. off-target effects.

The system uses an integrative big-data approach that combines a set of individually weak features into a single reliable predictor of shared-target drug relationships. Not dependent on complex 3D models or large known target cohorts, the system can be used to predict shared target drugs and mechanisms of action for any drug or small molecule (over 52,000 in one database example) which differentiates it from other target prediction methods. By using the top shared-target predictions the system can predict specific targets for a given small molecule and demonstrate how the system can be used to both efficiently discover new drugs with novel mechanisms for specific targets and identify targets for small molecules in the development pipeline—all without tedious, labor-intensive, and inaccurate drug screening approaches.

The system's predictions identified shared-target relationships, individual drug-target relationships, and mechanisms of action. Additionally, the system can replicate the results of large-scale experimental screens with no added data. In some implementations, the system be used to on a broader scale to discern mechanisms and observe how the global drug universe is structured.

The system can greatly improve the drug development pipeline. By allowing researchers to quickly obtain target predictions, the system can streamline all subsequent drug development efforts and save both time and money. Furthermore, the system can be used to rapidly screen a large database of compounds and efficiently identify any promising therapeutics that could be further evaluated. The system is an effective screening and target prediction approach for novel drug development.

Figure 18A:
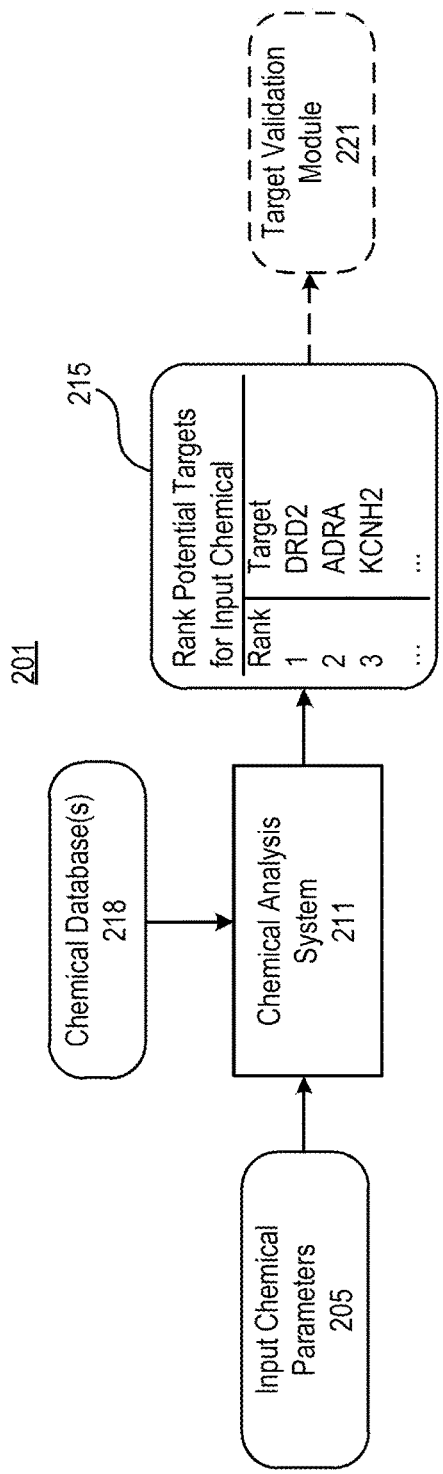
FIG. 18A is a block diagram illustrating the data flow in a system that can be used to predict targets for an input chemical.

Referring now to FIG. 18A, a block diagram illustrating the data flow in a environment 201 that can be used to predict targets for an input chemical is depicted. The environment 201 includes a computational chemical analysis system 211 configured to receive various chemical data, process the chemical, and predict at least one binding target for a given chemical based on the processed data. More particularly, the computational chemical analysis system 211 receives input chemical parameters 205 as well as information from one or more chemical databases 218. The input chemical parameters can include any known information relating to a chemical of interest (i.e., an input chemical). In some implementations, the chemical of interest can be an orphan small molecule, or any chemical for which binding targets are sought. In some implementations, the input chemical parameters 205 may include values for a plurality of datatypes related to the input chemical, including information related to chemical efficacy, post-treatment transcriptional responses, chemical structure, reported adverse effects, bioassay results, a chemogenomic fitness score, a known binding target, known drug indications, known drug interactions, drug dosing information, mass spectrometry images, fluorescence/microscopy images, electronic health record (EHR) data, gene expression and efficacy data in cells following genetic perturbation, or drug binding efficiencies, among others. In general, a datatype can be any characteristic of a chemical (e.g., its structure, etc.) or the effects of the chemical (e.g., side effects, known targets to which it binds, known interactions with other chemicals, etc.) Similarly, the information from the chemical databases 218 may include values for a plurality of datatypes related to any number of chemicals. In some implementations, the information from the chemical databases 218 may include information related to hundreds, thousands, or millions of chemicals, and may further include values for any number of datatypes for each chemical.

The computational chemical analysis system 211 can implement an algorithm that processes all of the information received from the chemical databases 218, as well as the input chemical parameters 205, to determine one or more potential binding targets for the input chemical. In some implementations, the computational chemical analysis system 211 can output a list 215 that ranks potential targets according to the likelihood that the input chemical will bind to the potential targets, based on the algorithm implemented by the computational chemical analysis system 211. In some implementations, the list 215 can be delivered to a target validation module 221 for further testing. The target validation module can include any systems and methods used to determine whether the input chemical binds to the potential targets included in the list 215, including chemical experiments, clinical trials, and the like. However, it should be understood that the target validation module 221 is shown for illustrative purposes only, and may not be a necessary component of the systems and methods described in this disclosure.

In general, target validation can be an expensive and time-consuming process in the drug development pipeline. Furthermore, expense and necessary time for successful target validation are typically driven by uncertainty regarding various targets that are likely to bind to the input chemical. For example, when very little information is known about the input chemical, including any targets that the input chemical may bind to, it may be necessary to attempt to validate whether the input chemical binds to a very large number of targets in order to find even a single target that actually binds to the input chemical. Thus, the list 215 produced by the computational chemical analysis system 211 can greatly reduce the time and expense of validating targets for the input chemical, because the list includes an indication of those targets that are most likely to bind with the input chemical. Researchers and other workers involved in the target validation process can therefore better focus their time and resources on validating whether the input chemical successfully binds with targets closer to the top of the list 215, which generally have a higher likelihood of binding with the input chemical than targets nearer to the bottom of the list 215 (or targets not included in the list 215).

Figure 18B:
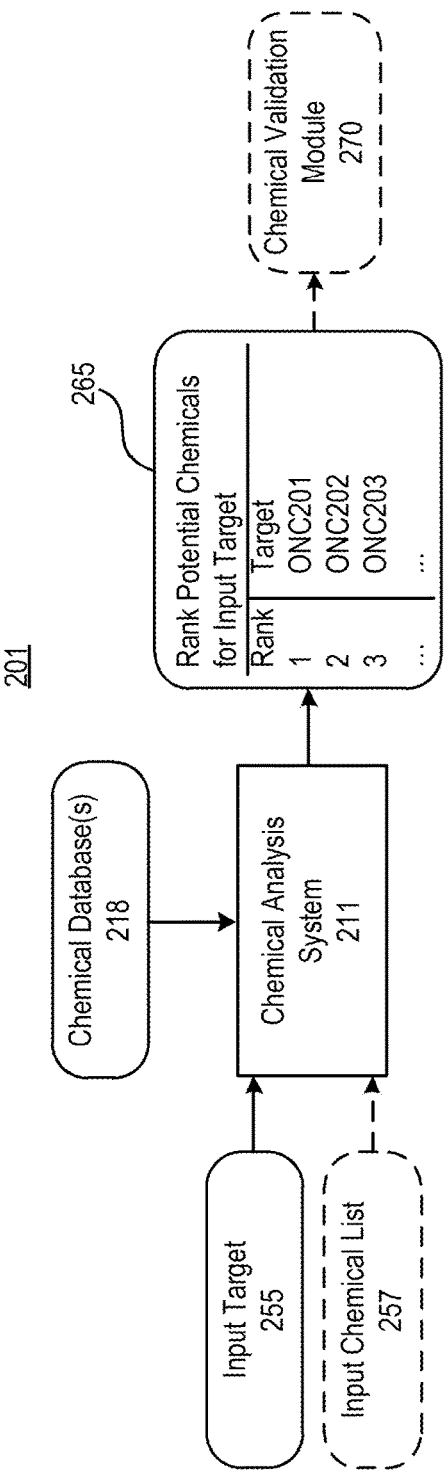
FIG. 18B is a block diagram illustrating the data flow in a system that can be used to predict one or more chemicals likely to bind to an input target.

FIG. 18B is a block diagram illustrating the data flow in an environment 202 that can be used to predict one or more chemicals likely to bind to an input target. Thus, the functionality of the environment 202 can be thought of as the inverse of the functionality provided by the environment 201 shown in FIG. 18A, in that the environment 201 receives a target of interest as an input and determines a set of chemicals likely to bind to the target of interest, rather than receiving a chemical of interest and determining a list of targets likely to bind to the chemical of interest. To that end, the computational chemical analysis system 211 receives an input target 255 in the environment 202. As in the environment 201, the computational chemical analysis system 211 in the environment 202 receives information from the one or more chemical databases 218. In addition, the computational chemical analysis system 211 also can optionally receive an input chemical list 257 in the environment 202. The input chemical list can be include a set of chemicals whose likelihood of binding with the input target 255 is sought. For example, in some implementations, the input chemical list 257 may include a list of chemicals in the early stages of drug development, which may be candidates for treating a disease modulated by the input target 255. In some other implementations, the input chemical list 257 may simply be omitted, and the computational chemical analysis system 211 can perform analysis to determine whether any chemicals included in the information received from the chemical databases 218 are likely to bind to the input target 255.

In the environment 202, the computational chemical analysis system 211 can implement an algorithm that processes the information received from the chemical databases 218, the input target 255, and optionally the input chemical list 257. The computational chemical analysis system 211 can then output a list 265 of potential chemicals likely to bind to the input target 255. The list 265 ranks potential chemicals according to the likelihood that they will bind to the input target 255. In some implementations, the list 265 can be delivered to a chemical validation module 270, which can include any systems and methods used to validate whether any of the chemicals included in the list 265 actually binds with the input target 255. However, it should be understood that the chemical validation module 270 is shown for illustrative purposes only, and may not be a necessary component of the systems and methods described in this disclosure. As described above, the validation process can be expensive and time consuming. Therefore, the computational chemical analysis system 211, which generates a ranked list 265 of potential chemicals that are likely to bind with the input target 255, can be used to substantially reduce the amount of time and resources necessary for successful validation in the drug development process. Further implementation details of the computational chemical analysis system 211 of FIGS. 18A and 18B are described below in connection with FIG. 19.

Figure 19:
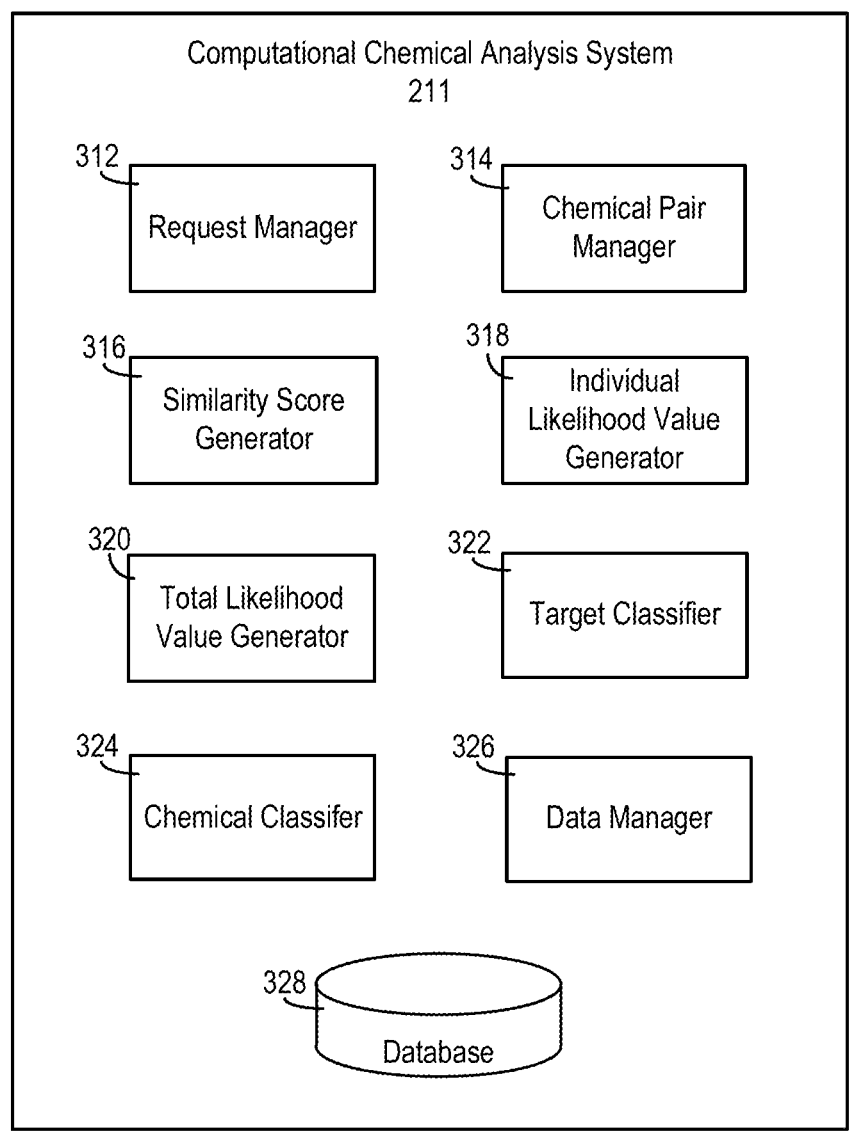
FIG. 19 depicts some of the architecture of an implementation of a system configured to computationally analyze chemical data.

FIG. 19 depicts some of the architecture of an implementation of the system 211, which is configured to computationally analyze chemical data. As described above, the system 211 can be configured to receive information from various chemical databases, as well as information related to particular chemicals or targets of interest, and can further be configured to determine one or more chemicals that are likely to bind to a given target or one or more targets that are likely to bind to a given chemical. In some implementations, the components of the system 211 shown in FIG. 19 can include or can be implemented using the systems and devices described above in connection with FIGS. 1A-1D. For example, the computational chemical analysis system 211 and any of its components may be implemented using computing devices similar to those shown in FIGS. 1C and 1D and may include any of the features of those devices, such as the CPU 121, the memory 122, the I/O devices 130a-130n, the network interface 118, etc.

Referring again to FIG. 19, the computational chemical analysis system 211 includes a request manager 312, a chemical pair manager 314, a similarity score generator 316, an individual likelihood value generator 318, a total likelihood value generator 320, a target classifier 322, a chemical classifier 324, a data manager 326, and a database 328. Together, the components of the computational chemical analysis system can be configured to implement the algorithms referred to above in connection with FIGS. 18A and 18B. In some implementations, the request manager 312, the chemical pair manager 314, the similarity score generator 316, the individual likelihood value generator 318, the total likelihood value generator 320, the target classifier 322, the chemical classifier 324, and the data manager 326 can each be implemented as a set of software instructions, computer code, or logic that performs the functionality of each of these components described further below. In some implementations, these components may instead by implemented by hardware, for example using a field programmable gate array (FPGA) or an application-specific integrated circuit (ASIC). In some implementations, these components can be implemented as a combination of hardware and software.

For example, the request manager 312 can be configured to receive a request for the system to perform a computational analysis of chemical data. As described above, in some implementations the request can be a request to predict one or more targets that are likely to bind to a given chemical. In such implementations, the request manager 312 also can receive information related to any number of datatypes for the chemical. For example, such a request can include any of the information included in the input chemical parameters 205 shown in FIG. 18A. In other examples, the request can be a request to predict one or more chemicals that are likely to bind to a given target. In such implementations, the request manager 312 also can receive information related to the input target 255, as well as the optional input chemical list 257 as shown in FIG. 18B. In either case, the computational chemical analysis system 211 also can receive information corresponding to a plurality of other chemicals (for example, the information from the chemical databases 218 shown in FIGS. 18A and 18B), and can store this information in one or more data structures within the database 328.

Generally, the computational chemical analysis system 211 analyzes the input information received by the request manager 312, as well as any information relating to other chemicals that may be stored in the database 328, by forming sets of chemical pairs and performing analysis on the chemical pairs according to a Bayesian framework. More particularly, the computational chemical analysis system 211 can serve as a naïve Bayesian classifier that can classify each chemical in a set of chemicals as either likely or unlikely to bind to a an input target. The computational chemical analysis system 211 also can perform Bayesian analysis to classify each target in a set of targets and either likely or unlikely to bind to an input chemical. For example, to determine potential binding targets for an input chemical, the chemical pair manager 314 can establish a set of chemical pairs each including the input chemical and a respective one of the plurality of other chemicals whose information is stored in the database 328. In some implementations, the data manager 326 can be configured to extract information from the database 328, and the chemical pair manager 314 can receive the extracted information from the data manager 326. Thus, in this example, if the database 328 includes information relating to 1,000 different chemicals, the chemical pair manager 314 can establish 1,000 chemical pairs, each including the input chemical and a respective one of the 1,000 chemicals whose information is stored in the database 328.

The similarity score generator 316 can be configured to generate a plurality of similarity scores for each chemical pair established by the chemical pair manager 328. More particularly, for each chemical pair, the similarity score generator 316 can calculate a similarity score for each datatype about which information for the two chemicals in the chemical pair is known. Stated in another way, the similarity score generator 316 can calculate, for a given chemical pair, a similarity score for only those datatypes for which there is information stored or otherwise known for both the chemicals in the chemical pair. Generally, the similarity score can be any indication of a degree of similarity between the values of a particular datatype for the two chemicals in a chemical pair. For example, the similarity score generator 316 can generate a similarity score relating to a growth inhibition datatype by calculating a Pearson correlation value across two or more growth inhibition data points for the two chemicals in a chemical pair. In some implementations, the Pearson correlation can be calculated across 20, 40, 60, or more data points for the two chemicals. Similarly, the similarity score generator 316 can generate a similarity score relating to gene expression and/or chemogenomic fitness score datatypes by calculating a Pearson correlation measuring a degree of similarity of the two chemicals in a chemical pair. In some implementations, the similarity score generator 316 can determine a measure of the linear correlation between two chemicals for each datatype for which the chemicals have associated datatype information that is accessible by the computational chemical analysis system 211.

In some implementations, the data manager 326 can be configured to format the data stored in the database 328 in a similar format across all of the chemicals for which data is known. As the systems and methods of this disclosure rely on computational analysis of data, consistent formatting of the values for datatypes across all chemicals for which information is known can help to ensure that the data can be used effectively to predict chemicals likely to bind to input targets, or targets likely to bind to an input chemical. Thus, the data manager 326 can facilitate the calculation of similarity scores by the similarity score generator 316 as described above (as well as the functionality of additional components of the computational chemical analysis system 211 described further below) by ensuring that data is formatted consistently in the database 328.

In some implementations, the chemicals of a chemical pair may include one or more datatypes relating to bioassay results. For example, bioassays may be classified as either positive or negative. The similarity score generator 316 can calculate a Jaccard index to be used as the similarity score, based on the number of shared positive assays between the two chemicals of a chemical pair. The Jaccard index is also known as Intersection over Union and the Jaccard similarity coefficient/index is a statistic used for comparing the similarity and diversity of sample sets. The Jaccard coefficient measures similarity between finite sample sets. Generally, the similarity score generator 316 may only calculate a similarity score related to bioassay results for chemical pairs in which both chemicals have been tested in at least one similar assay.

In some implementations, the similarity score generator 316 can be configured to generate a similarity score for a chemical structure datatype of each chemical pair. For example, for each chemical in a chemical pair, the similarity score generator 316 can use the atom-pair method to calculate a structural similarity between the two chemicals of the pair, and the result of the calculation can be used as the similarity score.

In some implementations, the similarity score generator 316 can be configured to generate a similarity score relating to an adverse effects (or "side effects") datatype for each chemical pair. For example, the similarity score generator 316 can receive "preferred term" side effects for each chemical of a chemical pair, and can calculate a Jaccard index to be used as the similarity score, based on the shared adverse effects for each chemical in the chemical pair.

It should be understood that, in many instances, the similarity scores generated by the similarity score generator 316 for a given chemical pair may be relatively uncorrelated from one another. This can indicate that each similarity score for a given chemical pair can be modeled as independent of the other similarity scores for that chemical pair.

After the chemical pair manager 314 has calculated one or more similarity scores across various datatypes for each chemical pair, the individual likelihood value generator 318 can be configured to convert each similarity score to a likelihood value. The likelihood value can indicate a likelihood that the two chemicals of a given chemical pair share a binding target based on a particular datatype. Some datatypes may be more discriminative than others with respect to their ability to predict a likelihood that a given chemical pair shares a binding target. The individual likelihood value generator 318 can take this information into account when determining individual likelihood values for each chemical pair. In some implementations, the individual likelihood value generator 318 can precompute the predictive ability of each datatype, for example based on the information relating to chemicals whose binding targets are known, which may be stored in the database 328. For a given datatype, the individual likelihood value generator 318 can be configured to analyze the pairs of known chemicals having similarity scores within predetermined ranges that together encompass the full range of possible similarity scores. For example, each similarity score may be a number between zero and one, and the individual likelihood value generator 318 can examine the pairs of known chemicals having similarity scores within a first range of 0.0 to 0.1, a second range of 0.1 to 0.2, a third range of 0.2 to 0.3, and so on. For each range, the individual likelihood value generator can determine the percentage of pairs of known chemicals who share a target. In general, for a datatype to be considered highly predictive, its corresponding similarity scores across a wide range of chemical pairs should indicate that the proportion of chemical pairs sharing a binding target within a higher range of similarity scores (e.g., 0.9 to 1.0) is significantly higher than the proportion of chemical pairs sharing a binding target within a higher range of similarity scores (e.g., 0.1 to 0.2). The individual likelihood value generator 318 can be configured to precompute this information, which can be used to convert a similarity score to an individual likelihood value. In some implementations, the individual likelihood value generator 318 can generate a likelihood value $L(s_n)$ defined as the fraction of chemical pairs with a shared target (ST pairs) having a similarity score $s_n$, divided by the fraction of the non-ST pairs with the same similarity score using the following equation:

$$L(s_n) = \frac{P_r(s_n \mid ST)}{P_r(s_n \mid non - ST)} \qquad \text{Eq. 1}$$

The total likelihood value generator 320 can then be configured to determine a total likelihood value for each chemical pair based on the individual likelihood values for each of the datatypes of the chemical pair. In some implementations, the total likelihood value generator 320 is configured to make the total likelihood value calculation within a naïve Bayes framework. For example, the total likelihood value generator 320 can calculate a total likelihood value TLR using the following equation:

$$TLR = L(s) = \Pi_n L(s_n) = L(s_1)(s_2) \ldots (s_n) \qquad \text{Eq. 2}$$

where "n" is equal to the number of datasets used in the calculation. In some implementations, the total likelihood value generated by the total likelihood value generator 320 for a given chemical pair can be proportional to the odds of the two chemicals in the given chemical pair sharing a given target, based on all available information. It should be understood that the equations shown above is illustrative only. In other implementations, the total likelihood value generator 320 may calculate the total likelihood value differently. For example, rather than simply multiplying the individual likelihood values together, the total likelihood value generator 320 could apply a weighting factor to each likelihood value prior to combining or multiplying them to generate the total likelihood value.

The target classifier 322 can be configured to classify targets as either likely or unlikely to bind to a given chemical, in order to identify at least one target predicted to bind to a given chemical. Thus, the target classifier 322 can be employed in implementations in which the request manager 312 has received a request to predict one or more targets that are likely to bind to an input chemical. To achieve this, the target classifier 322 can first identify all of the chemical pairs that include the input chemical. From among those pairs, the target classifier 322 can determine a subset of chemical pairs having a total likelihood value that exceeds a minimum likelihood threshold. The minimum likelihood threshold can be arbitrarily selected by the target classifier 322, and can represent a confidence level that each chemical of the chemical pair shares a binding target. In general, if a lower minimum likelihood threshold is selected, a larger number of chemical pairs can be expected to be included in the subset of chemical pairs that meet or exceed the threshold. In some implementations, the target classifier 322 can be configured to compile all known targets for the chemicals represented in the subset of chemical pairs that exceed the minimum likelihood threshold, and to classify these targets as either likely or unlikely to bind to the input chemical. The target classifier 322 can classify each such target, for example, based on the relative number of times it appears in the identified subset of chemical pairs. For example, the target classifier 322 can classify targets appearing a large number of times as likely to bind to the input chemical, and can classify targets appearing fewer times as unlikely to bind to the input chemical. The target classifier 322 can thus predict a set of targets that are most likely to bind to the input chemical. In some implementations, the target classifier 322 can be configured to rank these targets according to the number of times they appear among the identified subset of chemical pairs, with targets represented more frequently being assigned a higher rank. The target classifier 322 can generate a list of such a ranking, similar to the list 215 shown in FIG. 18A.

The chemical classifier 324 can be configured to classify chemicals as either likely or unlikely to bind to a given target, in order to identify at least one chemical predicted to bind to a given target. Thus, the chemical classifier 324 can be employed in implementations in which the request manager 312 has received a request to predict one or more chemicals that are likely to bind to an input target. To achieve this, the chemical classifier 324 can perform steps similar to those described above in connection with the target classifier 322. For example, the chemical classifier 324 can first identify all of the chemical pairs having at least one chemical that binds to the input target. From among those pairs, the chemical classifier 324 can determine a subset of chemical pairs having a total likelihood value that exceeds a minimum likelihood threshold. The minimum likelihood threshold can be arbitrarily selected by the target classifier 324, as described above. In some implementations, the chemical classifier 324 can be configured to identify all chemicals belonging to a chemical pair of the identified subset for which one of the chemicals is known to bind with the input chemical. The chemical classifier 324 can then classify chemicals appearing in this subset as likely to bind to the input target, based on their similarity to the chemicals that are known to bind to the input target. The chemical classifier 324 can be configured to classify other chemicals as unlikely to bind the input target. In some implementations, the chemical classifier 324 can rank these chemicals according to the number of chemical pairs they appear in within the subset, with chemicals represented a greater number of times receiving a higher ranking. Thus, the chemical classifier 324 can generate a ranked list of candidate chemicals likely to bind to an input chemical, similar to the list 265 shown in FIG. 18B.

FIG. 20 is an example representation of a data structure 400 for chemical data that can be used in the computational chemical analysis system 211 of FIG. 19. As described above, the systems and methods of this disclosure can use a large number of data points to predict candidate chemicals for binding to an input target, or candidate targets predicted to bind to an input chemical. In some implementations, these data points may be stored in the form of a data structure such as the data structure 400. The data structure 400 can be represented, for example, indexed by an identification of a chemical. In this particular example, the chemical is labeled "Chemical 1." A plurality of values each representing a respective datatype for the chemical can also be stored in the data structure 400. For example, the data structure 400 includes values corresponding to a chemical efficacy datatype 410, a post-treatment transcriptional responses datatype 415, a chemical structure datatype 420, a reported adverse effects datatype 425, a bioassay results datatype 430, a chemogenomic fitness score datatype 435, and a known binding targets datatype 440. In general, the values for each datatype can be formatted in similarly across all of the chemicals for which data is known. As the systems and methods of this disclosure rely on computational analysis of data, consistent formatting of the values for datatypes across all chemicals for which information is known can help to ensure that the data can be used effectively to predict chemicals likely to bind to input targets, or targets likely to bind to an input chemical.

It should be understood that the data structure 400 is illustrative only, and that other data structures are contemplated within the scope of this disclosure. The data structure 400 may include more or fewer datatypes than are shown, and may be stored in memory in various formats, including as an array, a linked list, a vector, or any other type of data structure. For example, in some implementations the data structure 400 may store information relating to additional datatypes such as known drug indications, known drug interactions, drug dosing information, mass spectrometry images, fluorescence/microscopy images, EHR data, gene expression and efficacy data in cells following genetic perturbation, or drug binding efficiencies, among others. In addition, it should be understood that many such data structures each representing the known information for a respective chemical (or a single data structure including the known information for many chemicals) may also be stored in memory and accessed by the systems and methods of this disclosure, such as the computational chemical analysis system 211 shown in FIG. 19.

Figure 21:
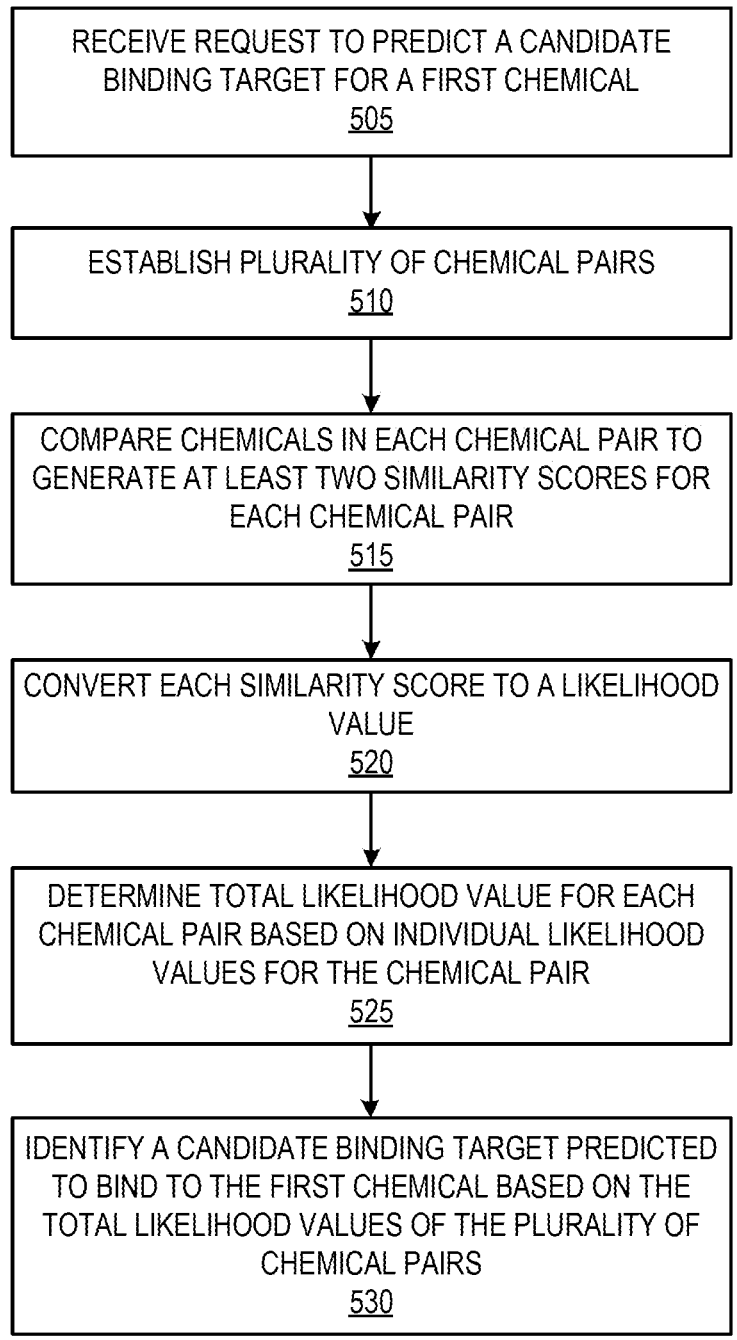
FIG. 21 is a flow chart for an example method of predicting targets for an input chemical.

FIG. 21 is a flow chart for an example method 500 of predicting targets for an input chemical. In brief overview the method 500 includes receiving a request to predict a candidate binding target for a first chemical (step 505), establishing a plurality of chemical pairs (step 510), comparing chemicals in each chemical pair to generate at least two similarity scores for each chemical pair (515), converting each similarity score to a likelihood value (step 520), determining a total likelihood value for each chemical pair based on the individual likelihood values for the chemical pair (step 525), and identifying a candidate binding target predicted to bind to the first chemical based on the total likelihood values of the plurality of chemical pairs (step 530).

Referring again to FIG. 21, and in greater detail, the method 500 includes receiving a request to predict a candidate binding target for a first chemical (step 505). In some implementations, this step can be performed by a request manager such as the request manager 312 shown in FIG. 19. In general, the request can include an indication of the first chemical (sometimes also referred to as an input chemical). The request also can include any information known about the first chemical, such as values for any datatypes that have been determined for the first chemical.

The method 500 also includes establishing a plurality of chemical pairs (step 510). In some implementations, this step can be performed by a chemical pair manager such as the chemical pair manager 314 shown in FIG. 19. The chemical pair manager can establish the plurality of chemical pairs such that each chemical pair includes the first chemical and a respective one of the plurality of second chemicals whose information is available. For example, in some implementations at least one binding target may be known for each of the plurality of second chemicals.

The method 500 also includes comparing chemicals in each chemical pair to generate at least two similarity scores for each chemical pair (515). In some implementations, this step can be performed by a similarity score generator such as the similarity score generator 316 shown in FIG. 19. Each chemical in a chemical pair can include information corresponding to values for a plurality of datatypes. For each chemical pair, the similarity score generator can calculate a similarity score for each datatype about which information for the two chemicals in the chemical pair is known. Generally, each similarity score can be an indication of a degree of similarity between the values of a particular datatype for the two chemicals in a chemical pair. For example, the similarity score generator 316 can generate a similarity score relating to each datatype using a Pearson correlation calculation, a Jaccard index calculation, an atom-pair calculation, a Tanimoto calculation, or any other type of calculation measuring a degree of similarity between the values of a given datatype for the two chemicals in a chemical pair, including any method for calculating the similarity between two chemical structures.

The method 500 also includes converting each similarity score to a likelihood value (step 520). In some implementations, this step can be performed by an individual likelihood value generator such as the individual likelihood value generator 318 shown in FIG. 19. The likelihood values can indicate a likelihood that the first chemical and the respective second chemical of a given chemical pair share a binding target, based on the values of a particular datatype for each of the first chemical and the second chemical. In some implementations, the individual likelihood value generator can generate a likelihood value $L(s_n)$ defined as the fraction of chemical pairs with a shared target (ST pairs) having a similarity score $s_n$, divided by the fraction of the non-ST pairs with the same similarity score, using Eq. 1 shown above in connection with the description of FIG. 19.

The method 500 also includes determining a total likelihood value for each chemical pair based on the individual likelihood values for the chemical pair (step 525). In some implementations, this step can be performed by a total likelihood value generator such as the total likelihood value generator 320 shown in FIG. 19. In some implementations, the total likelihood value generator is configured to make the total likelihood value calculation within a naïve Bayes framework. For example, the total likelihood value generator can calculate a total likelihood value using the following Eq. 2 described above in connection with the description of FIG. 19. The total likelihood value generated by the total likelihood value generator for a given chemical pair can be proportional to the odds of the two chemicals in the given chemical pair sharing a given target, based on all available information.

The method 500 also includes identifying a candidate binding target predicted to bind to the first chemical based on the total likelihood values of the plurality of chemical pairs (step 530). In some implementations, this step can be performed by a target classifier such as the target classifier 322 shown in FIG. 19. The target classifier can determine a subset of chemical pairs having a total likelihood value that exceeds a minimum likelihood threshold, which may be selected arbitrarily. In some implementations, the target classifier can be configured to compile all known targets for the chemicals represented in the subset of chemical pairs that exceed the minimum likelihood threshold, and to identify the targets that appear the most among these chemical pairs. The target classifier can then predict that these targets are most likely to bind to the first chemical.

Figure 22:
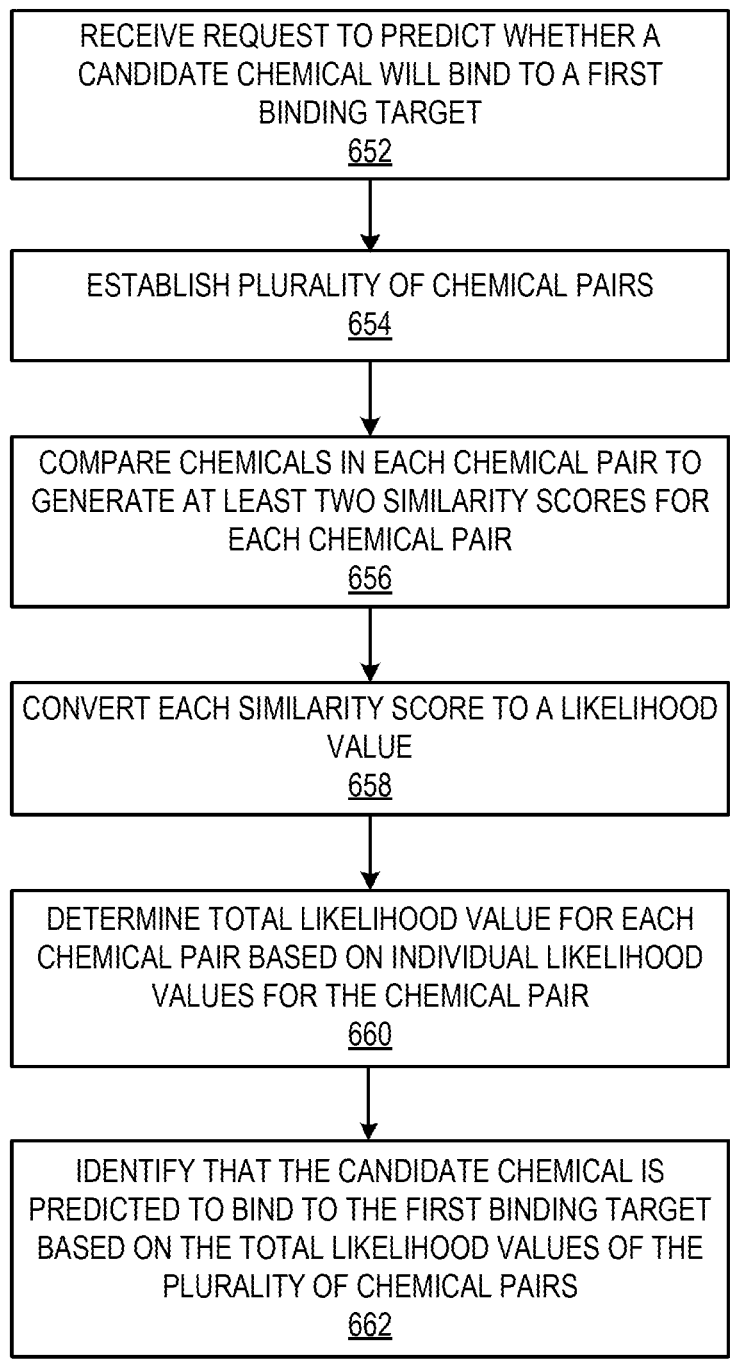
FIG. 22 is a flow chart for an example method of predicting one or more chemicals likely to bind to an input target.

FIG. 22 is a flow chart for an example method 650 of predicting one or more chemicals likely to bind to an input target. In brief overview the method 650 includes receiving a request to predict a whether a candidate chemical will bind to a first binding target (step 652), establishing a plurality of chemical pairs (step 654), comparing chemicals in each chemical pair to generate at least two similarity scores for each chemical pair (step 656), converting each similarity score to a likelihood value (step 658), determining a total likelihood value for each chemical pair based on the individual likelihood values for the chemical pair (step 660), and identifying that the candidate chemical is predicted to bind to the first binding target based on the total likelihood values of the plurality of chemical pairs (step 662).

Referring again to FIG. 22, and in greater detail, the method 650 includes receiving a request to predict a whether a candidate chemical will bind to a first target (step 652). In some implementations, this step can be performed by a request manager such as the request manager 312 shown in FIG. 19. In general, the request can include an indication of the first target (sometimes also referred to as an input target). The request also can optionally include a list of input chemicals that are to be tested to predict whether they are likely to bind with the input target.

The method 650 also includes establishing a plurality of chemical pairs (step 654). In some implementations, this step can be performed by a chemical pair manager such as the chemical pair manager 314 shown in FIG. 19. The chemical pair manager can establish the plurality of chemical pairs such that each chemical pair includes the candidate chemical and a respective one of the plurality of control chemicals whose information is available. For example, in some implementations each of the control chemicals may be known to bind with the first target.

The method 650 also includes comparing chemicals in each chemical pair to generate at least two similarity scores for each chemical pair (step 656). In some implementations, this step can be performed by a similarity score generator such as the similarity score generator 316 shown in FIG. 19. Each chemical in a chemical pair can include information corresponding to values for a plurality of datatypes. For each chemical pair, the similarity score generator can calculate a similarity score for each datatype about which information for the two chemicals in the chemical pair is known. Generally, each similarity score can be an indication of a degree of similarity between the values of a particular datatype for the two chemicals in a chemical pair. For example, the similarity score generator can generate a similarity score relating to each datatype using a Pearson correlation calculation, a Jaccard index calculation, an atom-pair calculation, a Tanimoto calculation, or any other type of calculation measuring a degree of similarity between the values of a given datatype for the two chemicals in a chemical pair, including any method for calculating the similarity between two chemical structures.

The method 650 also includes converting each similarity score to a likelihood value (step 658). In some implementations, this step can be performed by an individual likelihood value generator such as the individual likelihood value generator 318 shown in FIG. 19. The likelihood values can indicate a likelihood that the candidate chemical and the respective control chemical of a given chemical pair share a binding target, based on the values of a particular datatype for each of the candidate chemical and the control chemical. In some implementations, the individual likelihood value generator can generate a likelihood value $L(s_n)$ defined as the fraction of chemical pairs with a shared target (ST pairs) having a similarity score $s_n$ divided by the fraction of the non-ST pairs with the same similarity score, using Eq. 1 shown above in connection with the description of FIG. 19.

The method 650 also includes determining a total likelihood value for each chemical pair based on the individual likelihood values for the chemical pair (step 660). In some implementations, this step can be performed by a total likelihood value generator such as the total likelihood value generator 320 shown in FIG. 19. In some implementations, the total likelihood value generator is configured to make the total likelihood value calculation within a naïve Bayes framework. For example, the total likelihood value generator can calculate a total likelihood value using the following Eq. 2 described above in connection with the description of FIG. 19. The total likelihood value generated by the total likelihood value generator for a given chemical pair can be proportional to the odds of the two chemicals in the given chemical pair sharing a given target, based on all available information.

The method 650 also includes identifying that the candidate chemical is predicted to bind to the first binding target based on the total likelihood values of the plurality of chemical pairs (step 662). In some implementations, this step can be performed by a chemical classifier such as the chemical classifier 324 shown in FIG. 19. The chemical classifier can determine a subset of chemical pairs having a total likelihood value that exceeds a minimum likelihood threshold. The minimum likelihood threshold can be arbitrarily selected by the target classifier, as described above. In some implementations, the chemical classifier can identify the candidate chemical as likely to bind to the first target, based on its similarity to one or more of the control chemicals that are known to bind to the first target.

Figure 23A:
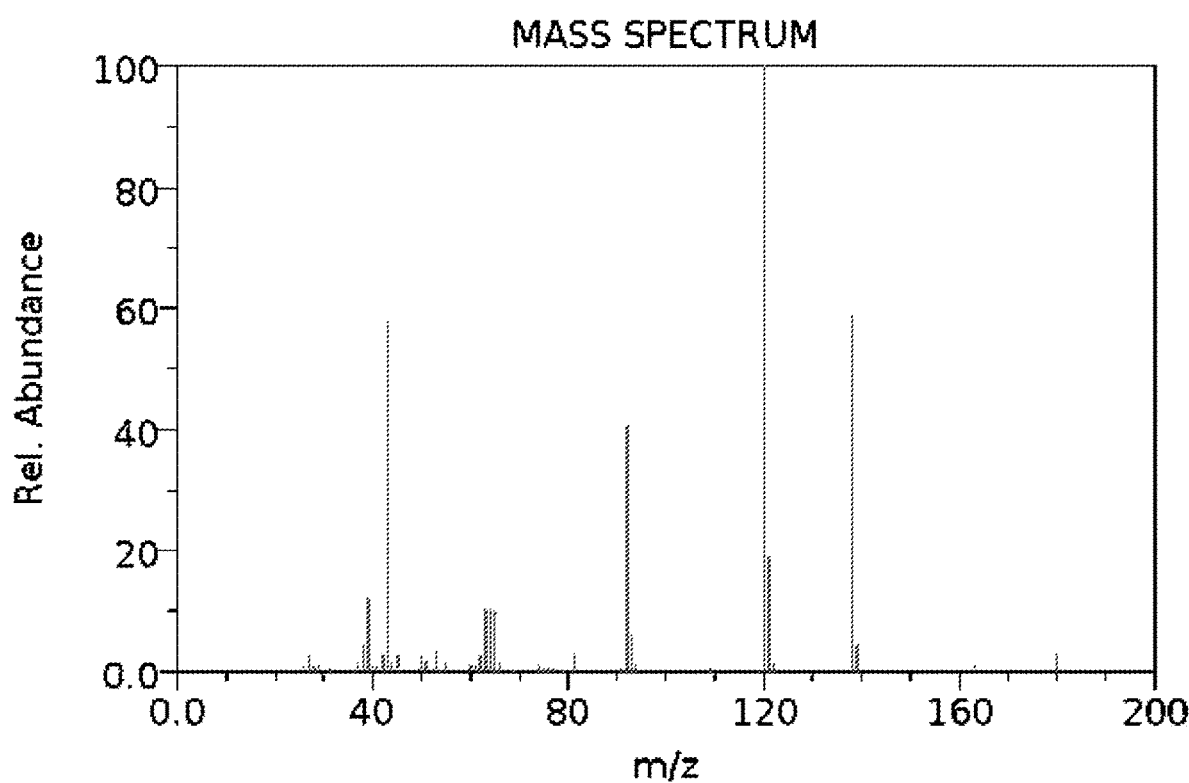
FIGS. 23A-23C are graphical representations of information relating to various chemical datatypes that may be used in the systems and methods of this disclosure.
Figure 23B:
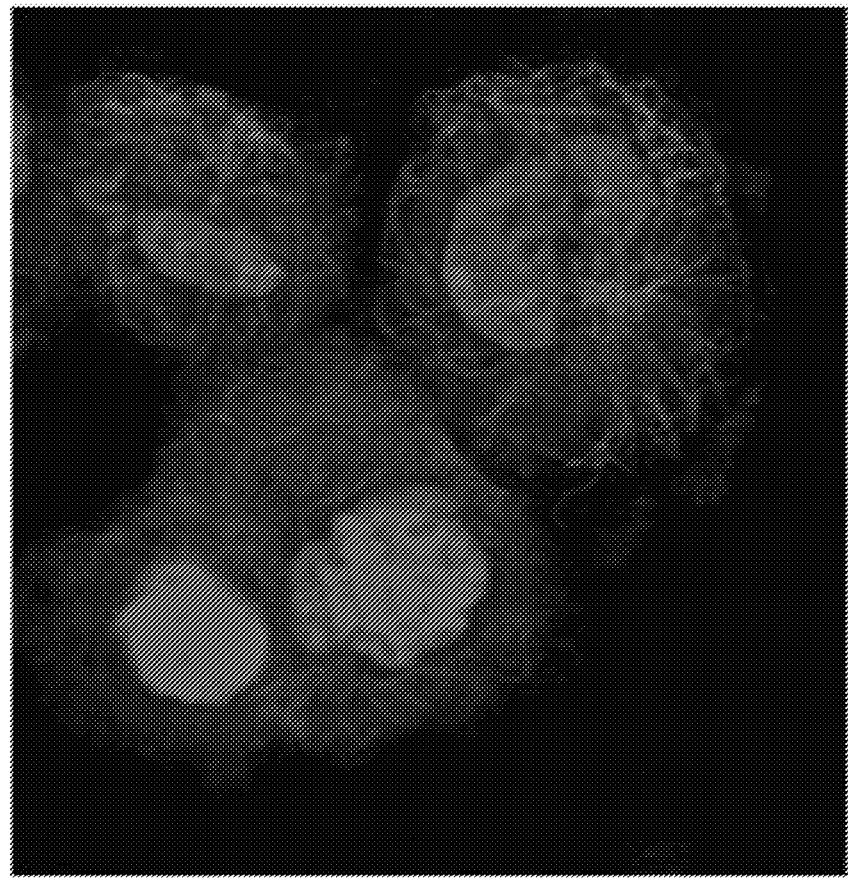
Figure 23C:
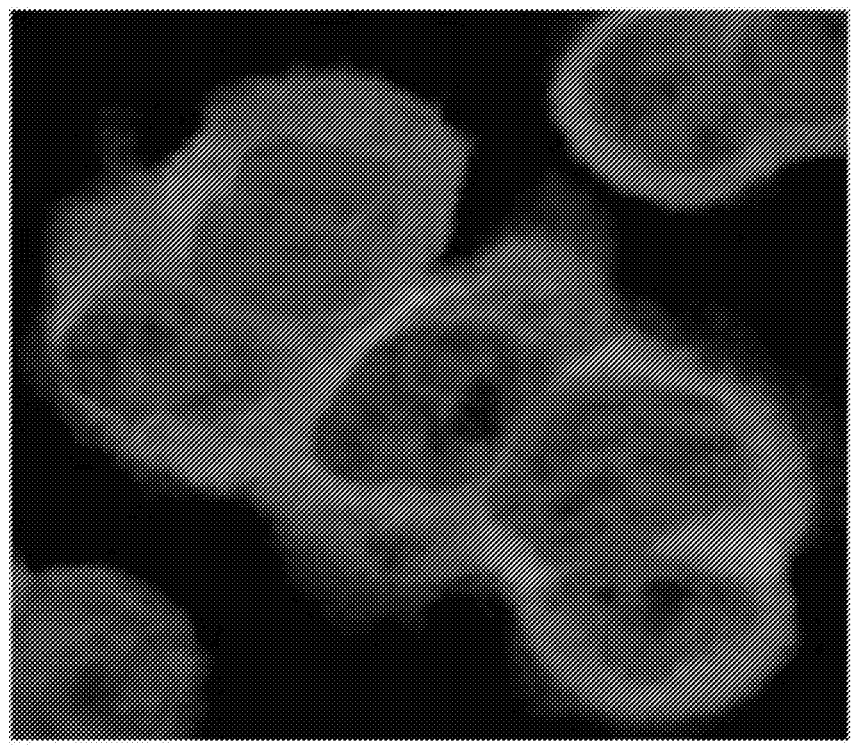

FIGS. 23A-23C are graphical representations of information relating to various chemical datatypes that may be used in the systems and methods of this disclosure. FIG. 23A is a graph 710 of mass spectrometry data for an example chemical. As shown, mass spectrometry data can be presented graphically in the bar graph 710 in which each bar represents an ion having a specific mass-to-charge ratio (labeled along the x-asix as "m/z"). The length of each bar indicates the relative abundance of each ion, as labeled along the y-axis. In some implementations, mass spectrometry data may be stored for a plurality of chemicals and compared to the mass spectrometry data of an input chemical to determine a similarity score, for example by the similarity score generator 316 shown in FIG. 19.

FIGS. 7B and 7C show microscopy images 720 and 730, respectively. The microscopy images 720 and 730 can be fluorescent images of cells following treatment by respective chemicals. For example, FIG. 23B shows a microscopy image 720 for a "control" chemical vinblastine, and FIG. 23C shows a microscopy image 730 for an input chemical labeled NSC406042. In some implementations, these images (or another form of data representing the graphical content of these images) can be compared to one another to generate a similarity score for a fluorescence/microscopy datatype for a chemical pair.

As described above, various other datatypes also can be used in connection with the systems and methods of this disclosure. For example, in some implementations, a datatype may relate to known drug indications for a given chemical. This can be formatted, for example, as a list of diseases that the given chemical is known to treat (e.g., breast cancer, diabetes, etc.). In some implementations, a datatype may relate to known drug interactions. This can be formatted as a list of other chemicals for which there is a known positive or negative interaction with a given chemical. For instance, a chemical may interact with another chemical to cause an increased risk of kidney failure.

In some implementations, a datatype may relate to drug dosing information. For example, drug dosing information can include any information relating to the doses of approved chemicals that are given to patients, and may be stored, for example, as numerical concentration values for a given chemical. In some implementations, a datatype may relate to EHR data. EHR data can include any information in health records recorded by a doctor for patients who are administered a given chemical.

In some implementations, a datatype may relate to gene expression and efficacy data in cells following genetic perturbation. This data can be formatted in a manner similar to that of data relating to growth inhibition/efficacy and gene expression data, with the addition of the genetic status of cells (i.e., perturbations prior to treatment with a given chemical) that are being measured. In some implementations, a datatype may relate to drug binding efficiencies. As described above, a datatype relating to binding targets may be stored in a binary format, indicating that a given chemical either does or does not bind with a given target. A drug binding efficiency datatype can include similar information, supplemented with information related to a degree of binding that occurs between the given chemical and the given target. For example, this information can include rate constants such as $K_{on}$ and $K_{off}$, as well as the equilibrium dissociation constant $K_D$.

CONCLUSION

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A system to improve the accuracy of a drug toxicity predictor, comprising:
   a data processing system having one or more processors coupled to a memory and configured to:
   determine a first structural vector of a first chemical based on a chemical structure of the first chemical, the first structural vector including values corresponding to one or more features derived from the chemical structure of the first chemical;
   determine a first target vector of the first chemical based on at least one gene target for the first chemical, the first target vector including values corresponding to one or more features derived from the at least one gene target and the first chemical;
   generate, by applying a machine learning classifier to the first structural vector and the first target vector, a toxicity predictor score for the first chemical, wherein:
   the machine learning classifier comprises a random forest classifier;

the machine learning classifier is trained, using a first plurality of reference chemicals and a second plurality of reference chemicals, to provide toxicity predictor scores based on structural and target vectors;

each first reference chemical of the first plurality of reference chemicals demonstrates adverse effects below an adverse effects threshold and has a respective structural vector including values corresponding to one or more features derived from the chemical structure of the respective first reference chemical and a respective target vector including values corresponding to one or more features derived from one or more gene targets and the respective first reference chemical; and each second reference chemical of the second plurality of reference chemicals demonstrates adverse effects above the adverse effects threshold and has a respective structural vector including values corresponding to one or more features derived from the chemical structure of the respective second reference chemical and a respective target vector including values corresponding to one or more features derived from one or more gene targets and the respective second reference chemical;

compare the toxicity predictor score for the first chemical to the adverse effects threshold; and provide, responsive to determining that the toxicity predictor score for the first chemical is below the adverse effects threshold, a prediction that the first chemical will demonstrate adverse effects below the adverse effects threshold.

2. The system of claim 1, wherein the first structural vector is based on atleast one chemical property feature and at least one drug-likeness feature, wherein the at least one chemical property feature includes a polar surface area, a molecular weight, a hydrogen bond donor count, a hydrogen bond acceptor count, a charge number, or a number of rotatable bonds and the at least one drug-likeness feature includes a quantitative estimate of drug-likeness (QED), a rule of five measure, a Veber rule measure, or a Ghose rule measure.

3. The system of claim 1, wherein the first target vector is based on at least one of a gene expression feature or a target feature, wherein the gene expression feature indicates a level of gene expression in a target tissue based on an exposure to the first chemical and the target tissue is at least one of liver tissue, heart tissue, kidney tissue, or brain tissue.

4. The system of claim 3, wherein the target feature includes at least one of a network connectivity feature, a network betweeness feature, a network degree feature, or a loss of function mutation frequency feature.

5. The system of claim 1, wherein the machine learning classifier is a random forest classifier.

6. The system of claim 1, wherein the random forest classifier includes between about 25 and 5000 decision trees.

7. The system of claim 6, wherein the data processing system is further configured to:
provide a random portion of a first plurality of values from the first structural vector to a first portion of the decision trees; and
provide a random portion of a second plurality of values from the first target vector to a second portion of the decision trees.

8. The system of claim 7, wherein the data processing system is further configured to:
determine, for each of the decision trees, a score indicating a relationship to the adverse effects threshold; and
generate the toxicity predictor score based on the score from each of the decision trees.

9. The system of claim 1, wherein the first plurality of reference chemicals includes a plurality of drugs that passed clinical trials and the second plurality of reference chemicals includes a plurality of drugs that failed clinical trials.

10. The system of claim 1, wherein the data processing system is further configured to determine the at least one gene target for the first chemical based on the chemical structure of the first chemical.

11. A method to improve the accuracy of a drug toxicity predictor, comprising:
determining a first structural vector of a first chemical based on a chemical structure of the first chemical, the first structural vector including values corresponding to one or more features derived from the chemical structure of the first chemical;
determining a first target vector of the first chemical based on at least one gene target for the first chemical, the first target vector including values corresponding to oneor more features derived from the at least one gene target and the first chemical;
generating, by applying a machine learning classifier to the first structural vector and the first target vector, a toxicity predictor score for the first chemical, wherein:
the machine learning classifier comprises a random forest classifier;
the machine learning classifier is configured to receive structural vectors and target vectors as inputs and provide toxicity predictor scores as outputs, the machine learning classifier having been trained using a first plurality of reference chemicals and a second plurality of reference chemicals;
each first reference chemical of the first plurality of reference chemicals demonstrates adverse effects below an adverse effects threshold and has a respective structural vector including values corresponding to one or more features derived from thechemical structure of the respective first reference chemical and a respective target vector including values corresponding to one or more features derived from one or more gene targets and the respective first reference chemical; and
each second reference chemical of the second plurality of reference chemicals demonstrates adverse effects above the adverse effects threshold and has a respective structural vector including values corresponding to one or more features derived from the chemical structure of the respective second reference chemical and a respective target vector including values corresponding to one or more features derived from one or more gene targets and the respective second reference chemical;
comparing the toxicity predictor score for the first chemical to the adverse effects threshold; and
providing, responsive to determining that the toxicity predictor score for the first chemical is below the adverse effects threshold, a prediction that the first chemical will demonstrate adverse effects below the adverse effects threshold.

12. The method of claim 11, wherein the structural vector comprises at least one chemical property feature and at least one drug-likeness feature, wherein the at least one chemical property feature includes a polar surface area, a molecular weight, a hydrogen bond donor count, a hydrogen bond acceptor count, a charge number, or a number of rotatable bonds and the at least one drug-likeness feature includes a quantitative estimate of drug-likeness (QED), a rule of five measure, a Veber rulemeasure, or a Ghose rule measure.

13. The method of claim 11, wherein the target vector comprises at least one of a tissue expression feature or a target feature, wherein a gene expression feature indicates a level of gene expression in a target tissue based on an exposure to the first chemical and the target tissue is at least one of liver tissue, heart tissue, kidney tissue, or brain tissue.

14. The method of claim 13, wherein the target feature includes at least one of a network connectivity feature, a network betweeness feature, a network degree feature, or a loss of function mutation frequency feature.

15. The method of claim 11, wherein the machine learning classifier is a random forest classifier.

16. The method of claim 11, wherein the random forest classifier includes betweenabout 25 and 5000 decision trees.

17. The method of claim 16, further comprising:
providing a random portion of a first plurality of values from the first structural vector to a first portion of the decision trees; and
providing a random portion of a second plurality of values from the first target vector to a second portion of the decision trees.

18. The method of claim 17, further comprising:
determining, for each of the decision trees, a score indicating a relationship to the adverse effects threshold; and
generating the toxicity predictor score based on the score from each of the decision trees.

19. The method of claim 11, wherein the first plurality of reference chemicals includes a plurality of drugs that passed clinical trials and the second plurality of reference chemicals includes a plurality of drugs that failed clinical trials.

20. The method of claim 11, further comprising:
determining the at least one gene target for the first chemical based on the chemical structure of the first chemical.

* * * * *